United States Patent
Leal et al.

(10) Patent No.: US 10,934,569 B1
(45) Date of Patent: Mar. 2, 2021

(54) ENZYMATIC PROCESSES FOR SYNTHESIZING RNA CONTAINING CERTAIN NON-STANDARD NUCLEOTIDES

(71) Applicants: Nicole A Leal, Gainesville, FL (US); Steven A Benner, Gainesville, FL (US)

(72) Inventors: Nicole A Leal, Gainesville, FL (US); Steven A Benner, Gainesville, FL (US)

( * ) Notice: Subject to any disclaimer, the term of this patent is extended or adjusted under 35 U.S.C. 154(b) by 48 days.

(21) Appl. No.: 16/226,963

(22) Filed: Dec. 20, 2018

(51) Int. Cl.
*C12P 19/34* (2006.01)

(52) U.S. Cl.
CPC .................................. *C12P 19/34* (2013.01)

(58) Field of Classification Search
None
See application file for complete search history.

(56) References Cited

U.S. PATENT DOCUMENTS

| | | | | |
|---|---|---|---|---|
| 5,432,272 A * | 7/1995 | Benner | .................. | C07H 21/00 435/91.1 |
| 6,617,106 B1 * | 9/2003 | Benner | .................. | C07H 21/00 435/6.1 |
| 8,101,385 B2 * | 1/2012 | Cload | .................... | C12P 19/34 435/6.12 |
| 9,637,783 B1 * | 5/2017 | Benner | .................. | C12P 19/34 |
| 2009/0081679 A1 * | 3/2009 | Keefe | ................ | C12N 15/1048 435/6.11 |

OTHER PUBLICATIONS

Kimoto et. al. Genetic alphabet expansion transcription generating functional RNA molecules containing a five-letter alphabet including modified unnatural and natural base nucleotides by thermostable T7. Chemical Communication. 2017, 53, 12309-12312 (Year: 2017).*

Kim et. al. Ribonucleosides for an Artificially Expanded Genetic Information System. The Journal of Organic Chemistry. 2014, 79, 3194-3199 (Year: 2014).*

Kimoto, M., Cox 3rd , R. S., Hirao, I. (2011). Unnatural base pair systems for sensing and diagnostic applications. Expert Review of Molecular Diagnostics 11, 321-331 (Year: 2011).*

Morales, J. C., Kool, E.T. (1999). Minor groove interactions between polymerase and DNA: More essential to replication than Watson-Crick hydrogen bonds? J. Am. Chem. Soc. 121, 2323-2324 (Year: 1999).*

Leconte, A.M., Hwang, G. T. Matsuda, S, Capek, P, Hari, Y, Romesberg, F. E. et al. (2008) Discovery, characterization, and optimization of an unnatural base pair for expansion of the genetic alphabet. J. Am. Chem. Soc. 130, 2336-2343 (Year: 2008).*

Hendrickson, C., Devine, K., Benner, S. A. (2004) Probing minor groove recognition contacts by DNA polymerases and reverse transcriptases using 3-deaza-2'-deoxyadenosine. Nucl. Acids Res. 32, 2241-2250 (Year: 2004).*

Switzer, C. Y., Moroney, S. E., Benner, S. A. (1989) Enzymatic incorporation of a new base pair into DNA and RNA. J. Am. Chem. Soc. 111, 8322-8323 (Year: 1989).*

Piccirilli, J. A., Krauch, T., Moroney, S. E., Benner, S. A. (1990) Extending the genetic alphabet. Enzymatic incorporation of a new base pair into DNA and RNA. Nature 343, 33-37 (Year: 1990).*

Switzer, C. Y., Moroney, S. E., Benner, S. A. (1993) Enzymatic recognition of the base pair between iso-cytidine and iso-guanosine. Biochemistry 32, 10489-10496 (Year: 1993).*

Hoshika et. al. (2019) Hachimoji DNA and RNA. A genetic system with eight building blocks. Science 363, 884-887] (Year: 2019).*

* cited by examiner

*Primary Examiner* — Neil P Hammell
*Assistant Examiner* — Tiffany Nicole Grooms

(57) ABSTRACT

This invention relates to processes that transcribe DNA molecules containing non-standard nucleotides using variants of T7 RNA polymerase to give RNA transcripts that contain their complementary non-standard nucleotides. Non-standard nucleotides pair during transcription using patterns of hydrogen bonding that are different from patterns that join the thymine-adenine and guanine-cytosine nucleobase pairs.

6 Claims, 43 Drawing Sheets

Specification includes a Sequence Listing.

ENZYMATIC PROCESSES FOR SYNTHESIZING RNA CONTAINING CERTAIN NON-STANDARD NUCLEOTIDES

STATEMENT OF RIGHTS TO INVENTIONS MADE UNDER FEDERALLY-SPONSORED RESEARCH

This invention was made with government support under grants from the National Institutes of Health (R01GM128186). The government has certain rights in the invention.

CROSS REFERENCE TO RELATED APPLICATIONS

None

THE NAMES OF PARTIES TO A JOINT RESEARCH AGREEMENT

Not applicable

INCORPORATION BY REFERENCE OF MATERIAL SUBMITTED ON A COMPACT DISK

None

BACKGROUND OF THE INVENTION

1. Field of the Invention

This invention relates to nucleotide analogs and their derivatives (termed non-standard nucleotides) that, when incorporated into DNA and RNA, expand the number of nucleotides beyond the four found in standard DNA and RNA. The invention further relates to enzymatic processes that incorporate those non-standard nucleotide analogs into oligonucleotide products using the corresponding triphosphate derivatives. The RNA polymerases of the instant invention transcribe DNA containing nonstandard nucleotides to give RNA containing nonstandard nucleotides, where certain of those nucleotides have nucleobases that do not present electron density to the minor groove.

2. Description of the Related Art

Natural oligonucleotides bind to complementary oligonucleotides according to rules of nucleobase pairing first elaborated by Watson and Crick in 1953, where adenine (A) pairs with thymine (T) (or uracil, U, in RNA), and guanine (G) pairs with cytosine (C), with the complementary strands anti-parallel to each other. These rules arise from two principles of complementarity, size-complementarity (large purines pair with small pyrimidines) and hydrogen bonding complementarity (hydrogen bond donors pair with hydrogen bond acceptors).

It is now well established in the art that the number of independently replicable nucleotides in DNA can be increased, where the size- and hydrogen binding complementarities are retained, but where different heterocycles (nucleobases or, as appropriate, nucleobase analogs) attached to the sugar-phosphate backbone implement different hydrogen bonding patterns. As many as eight different hydrogen bonding patterns forming four additional nucleobase pairs are conceivable (see, for example, [Benner, S. A. (1995) *Non-standard Base Pairs with Novel Hydrogen Bonding Patterns*. U.S. Pat. No. 5,432,272 (Jul. 11, 1995)]). This has led to an "artificially expanded genetic information system" (AEGIS). As illustrated in FIG. 1, different nucleobases/nucleobase analogs/heterocycles can implement the same hydrogen bonding pattern, standard or non-standard.

Additional nucleobase pairs have had substantial use in diagnostics, in part because the alternative hydrogen bonding patterns support orthogonal pairing. There and in this disclosure, "DNA" includes oligonucleotides containing nucleic acids and their analogs carrying tags (e.g., fluorescent, functionalized, or binding) to the ends, sugars, or nucleobases.

It would also be useful to transcribe DNA oligonucleotides containing non-standard components to give RNA containing complementary non-standard components. For example, messenger RNA containing non-standard components and transfer RNA containing the complementary non-standard components, may be used in ribosome-mediated translation to incorporate non-standard amino acids into a peptide [Bain, J. D., Chamberlin, A. R., Switzer, C. Y., Benner, S. A. (1992) Ribosome-mediated incorporation of non-standard amino acids into a peptide through expansion of the genetic code. *Nature* 356, 537-539].

Indeed, the art contains descriptions of procedures that do transcribe DNA oligonucleotides containing AEGIS components to give RNA containing complementary non-standard components [Leal, N. A., Kim, H.-J., Hoshika, S., Kim, M.-J., Carrigan, M. A., Benner, S. A. (2015) Transcription, reverse transcription, and analysis of RNA containing artificial genetic components. *ACS Synthetic Biol.* 4, 407-413]. However, without wishing to be bound by theory, for transcription to be successful, it appears that the non-standard components must not differ from standard nucleotide components in one critical way: They must present electron density into the minor groove, either from the nitrogen at position 3 analogous to N3 of standard purines, or from the exocyclic oxygen from the C=O group at position 2 analogous to the 2-position C=O of cytosine and thymine/uracil.

Theory notwithstanding, the art reports examples where a nonstandard ribonucleoside triphosphate that is an analog of a pyrimidine that presents, instead of a C=O group and its electron density, an —$NH_2$ group at the position analogous to the 2-position, fails to be incorporated into RNA by enzymatic transcription of a DNA template containing the corresponding nonstandard templating nucleotide [C. Y. Switzer, S. E. Moroney, S. A. Benner, Enzymatic recognition of the base pair between iso-cytidine and iso-guanosine. *Biochemistry* 32, 10489-10496 (1993)]. For this reason, the art does not enable this kind of transcription, especially when the pyrimidine analog is isocytidine or its analogs (e.g. pseudocytidine), diaminopyrimidine, 2,4-diaminopyridine or its derivatives (e.g., the 5-nitro derivative), 2-aminopyridin-4-ones and their derivatives (e.g., the 5 nitro derivative), and purine derivatives such as xanthosine and 7-deazaxanthosine that have an NH at the 3-position in the purine numbering scheme (FIG. 1). Processes that perform this transcription are the goal of this invention.

BRIEF SUMMARY OF THE INVENTION

This invention covers processes for transcribing DNA oligonucleotides to give RNA transcripts that incorporate non-standard nucleotides that do not present electron density to the minor groove. Those processes depend on variants of RNA polymerases that accept nonstandard nucleotides that do not present electron density to the minor groove. Further described for the first time is a DNA-like system that has eight different nucleotide-like building blocks with predictable pairing. Inventive parameters are provided that allow useful prediction of the pairing of duplexes containing certain standard and non-standard nucleobase pairs.

GGG ΔGU GUU GUA UUU GGS CAA UUU SEQ ID NO 1 with one S relative to 5 {A+C}, 8 G, and 10 U. Using the extinction coefficients above, 1.2±0.4 S nucleotides were incorporated into the transcript by the FAL variant of T7 RNA polymerase.

Figure 15:
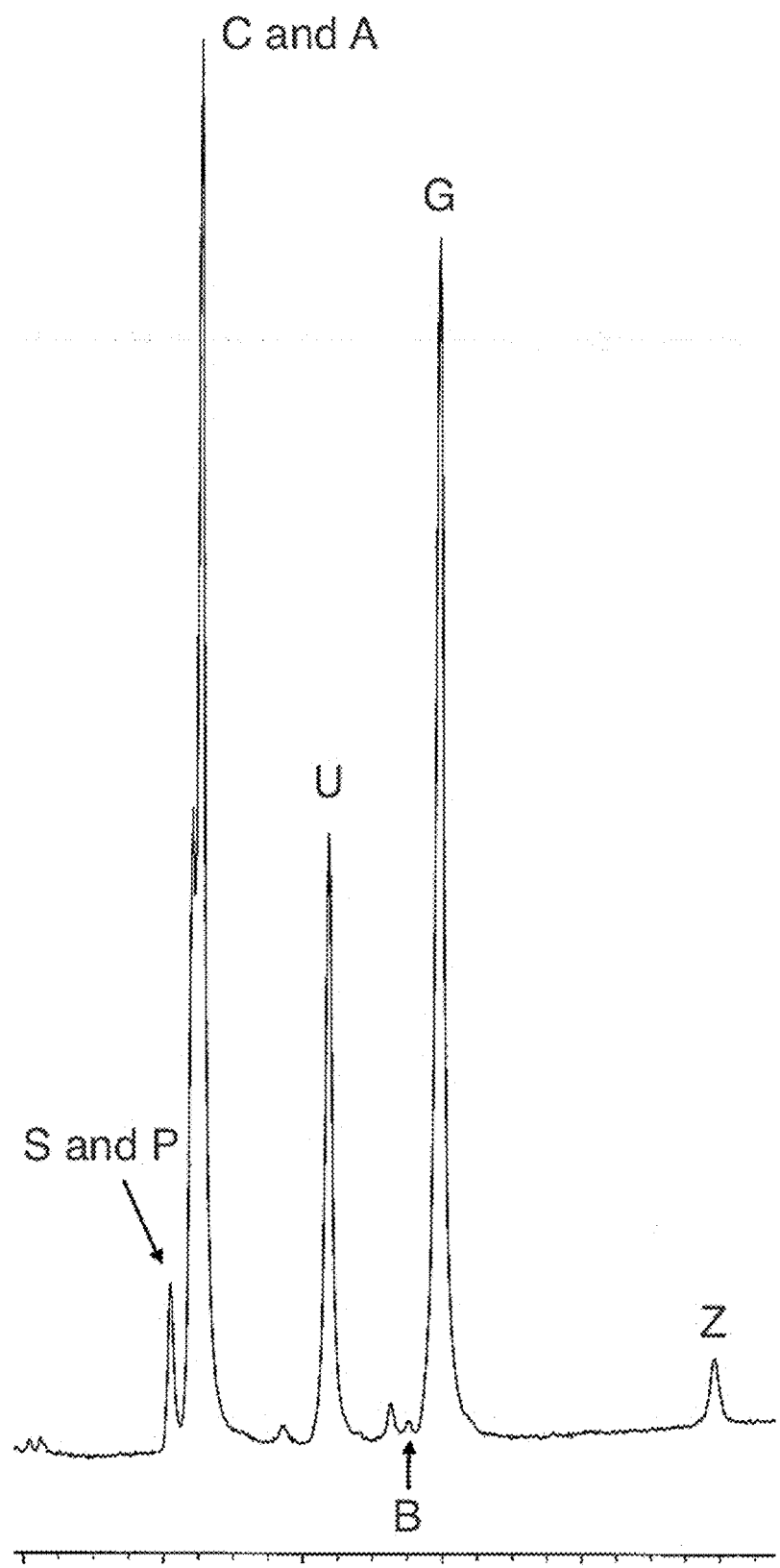
Figure 15:
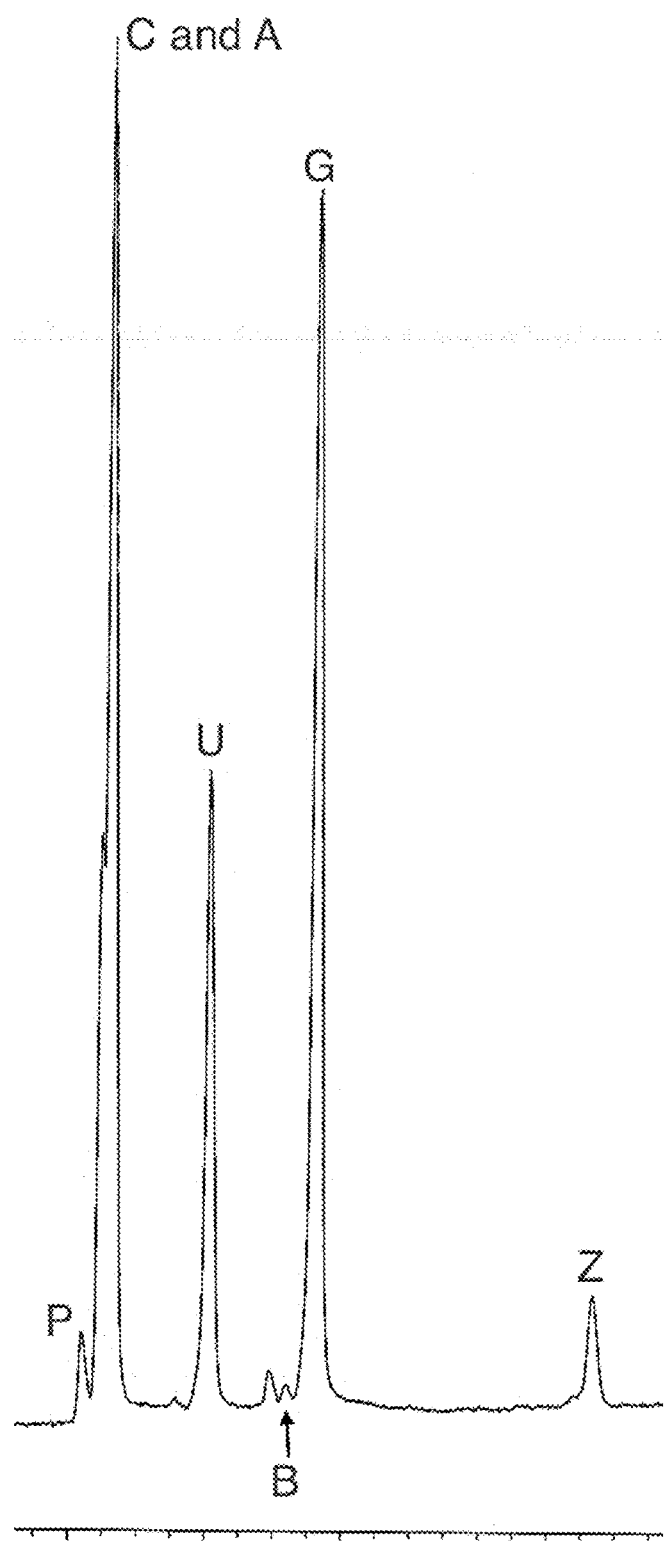
Figure 15:
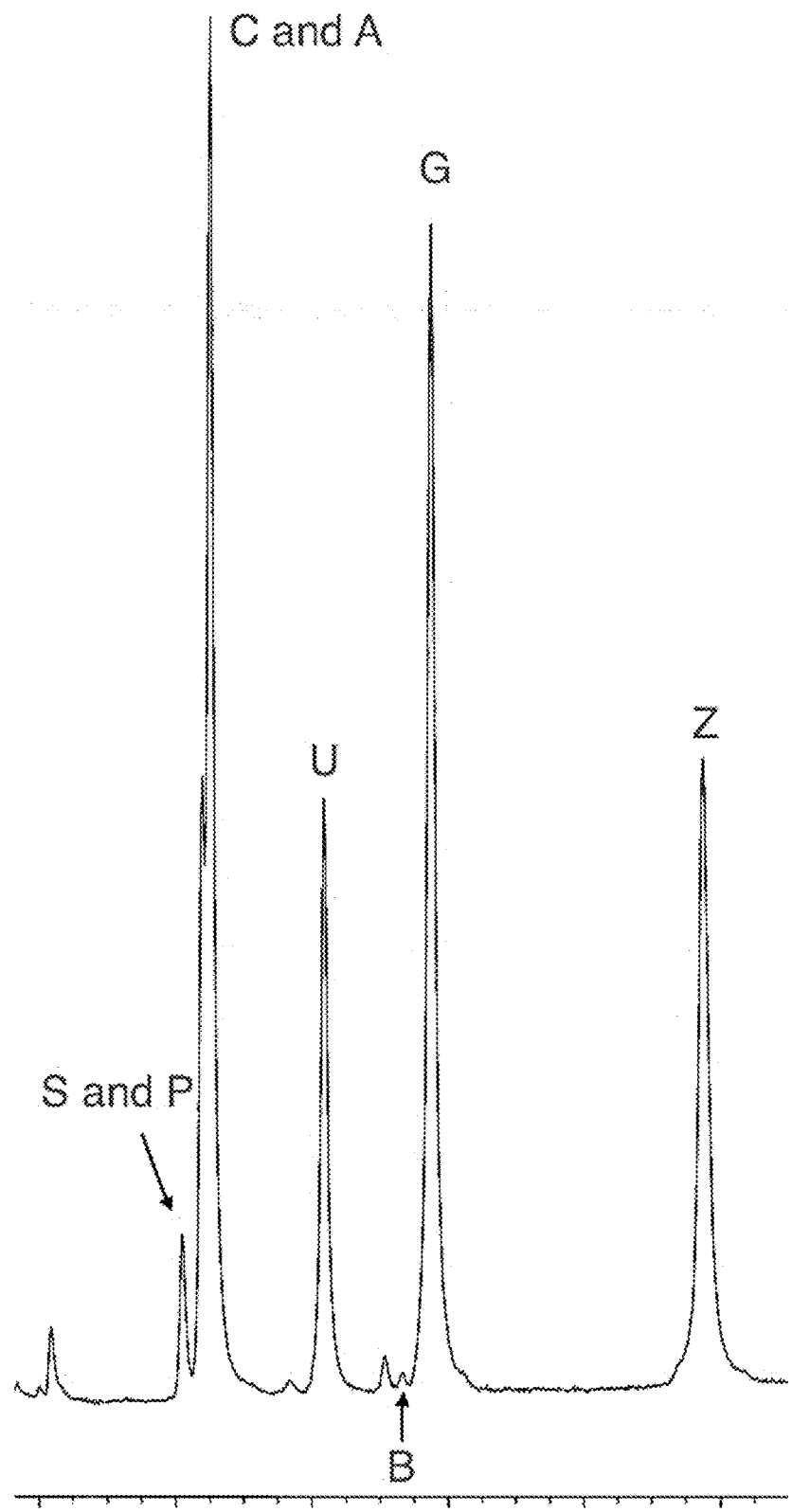

FIG. 15 A-FIG. 15 C. HPLC trace (ammonium bicarbonate, 0 to 200 mM) of rN-3'-monophosphates recovered by RNase T2 digestion of the spinach aptamer made by transcription of a 8-letter template. (A) Products from the aptamer made by wild-type T7 RNA polymerase; it does not contain S-3'-P, as confirmed by TLC. (B) Products from the aptamer made by the FAL variant of T7 RNA polymerase containing all eight components (G, A, C, T, Z, P, S, and B). (C) Products from the aptamer made by the FAL variant of T7 RNA polymerase with co-injection of the authentic rZ-3'-monophosphate made by chemical synthesis.

Figure 16:
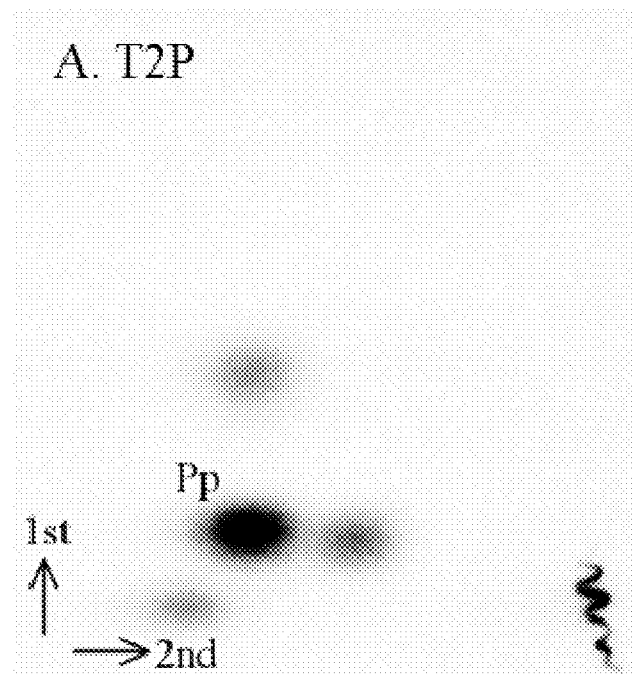
Figure 16:
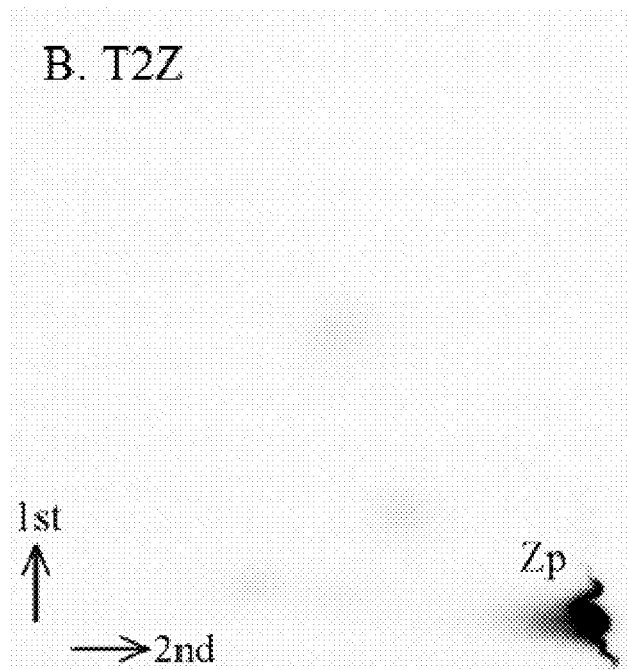
Figure 16:
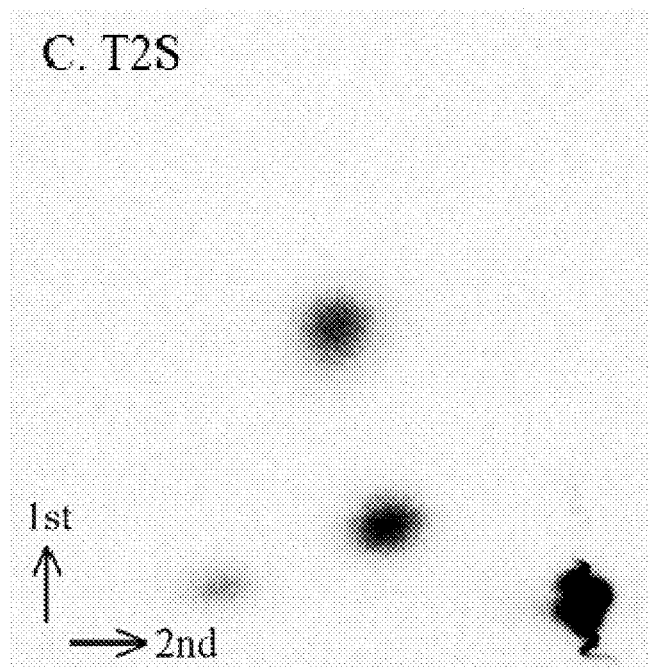
Figure 16:
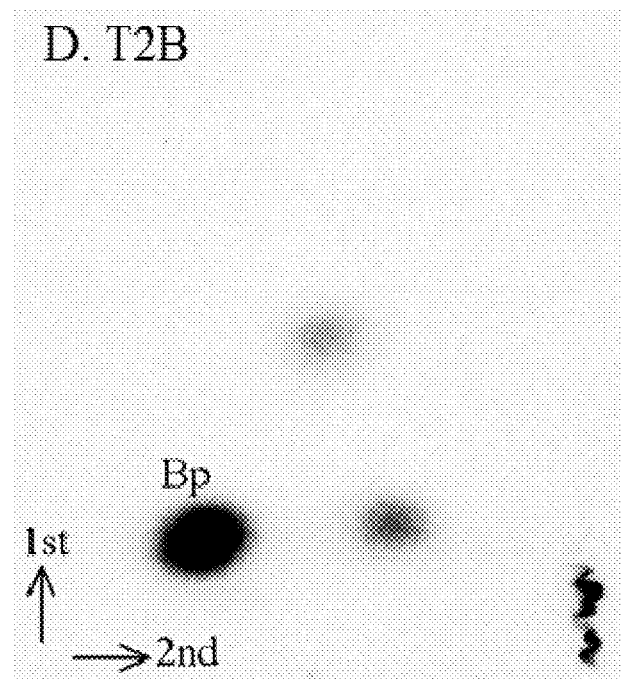
Figure 16:
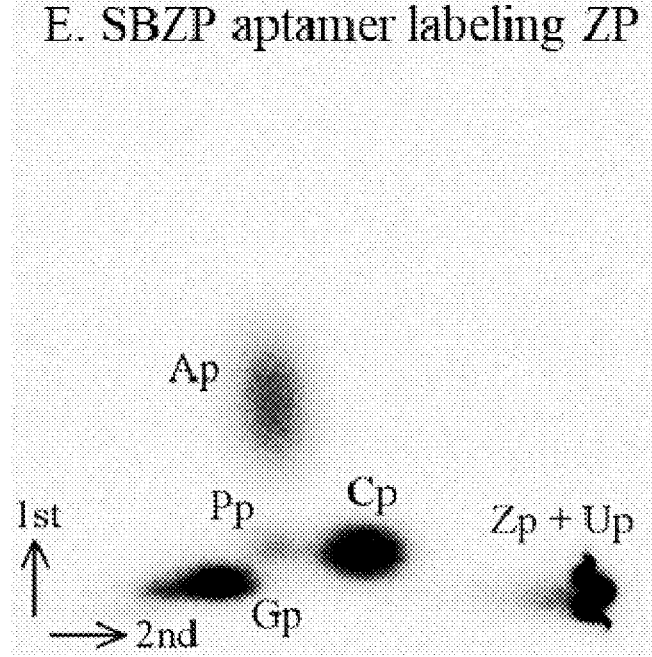
Figure 16:
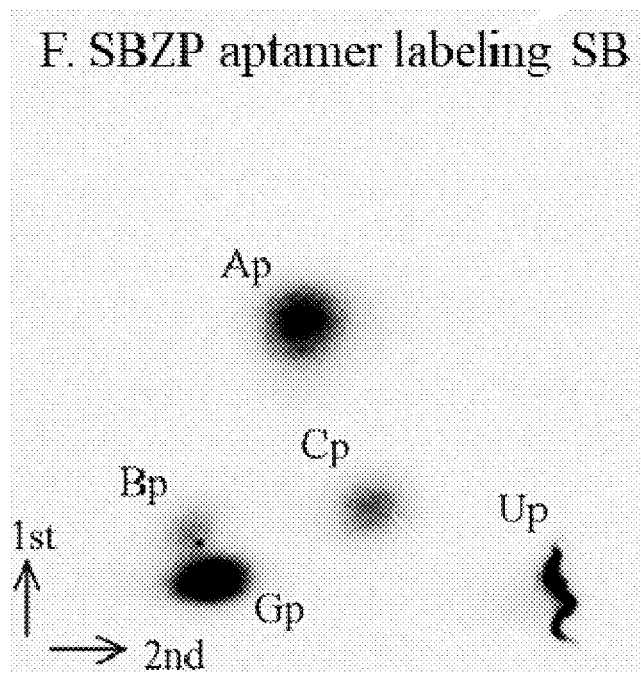

FIG. 16 A-FIG. 16 F. 2D-TLC of RNase T2 digests of labeled test sequences (panels A-D) and spinach (panels E and F) made with wild-type T7 RNA polymerase in primary solvent system. (A) With template giving a product containing P as the only 8-letter non-standard nucleotide, generates P-3'-$^{32}$P (Pp) after digestion. (B) With template giving a product containing Z as the only 8-letter non-standard nucleotide, generates Z-3'-$^{32}$P (Zp) after digestion, which runs with U-3'-P. (C) With template that produces a product containing S as the only 8-letter non-standard nucleotide, wild-type T7 RNA polymerase apparently does not incorporate STP (absence of S-3'-$^{32}$P which would run to the right of C-3'-P in this solvent system, shown below). (D) With template giving a product containing B as the only 8-letter non-standard nucleotide, generates B-3'-$^{32}$P (Bp) after digestion. (E) Transcript of the spinach aptamer using alpha-$^{32}$P-GTP, which nearest neighbor labels all four standard nucleotides, as well as Z and P. After digestion, evidence of incorporation comes from the appearance of the corresponding Z-3'-$^{32}$P (Zp) and P-3'-$^{32}$P (Pp). Since Z-3'-P does not separate convincingly in this system, its presence in the spinach aptamer was confirmed by HPLC (Figure E10), and in a second buffer system (shown below). (F) Transcript of the spinach aptamer using alpha-$^{32}$P-CTP, which nearest neighbor labels all four standard nucleotides, as well as S and B. After digestion, evidence of incorporation of BTP comes from the appearance of the corresponding B-3'-$^{32}$P (Bp). However, essentially no amount of radioactivity is attributable to S-3'-$^{32}$P. This suggests the need to use a variant of T7 RNA polymerase to allow the preparation of 8-letter RNA from 8-letter DNA by transcription. In addition, a secondary TLC system was required to resolve all eight 3'-phosphates arising from all eight components of the 8-letter system.

Figure 17:
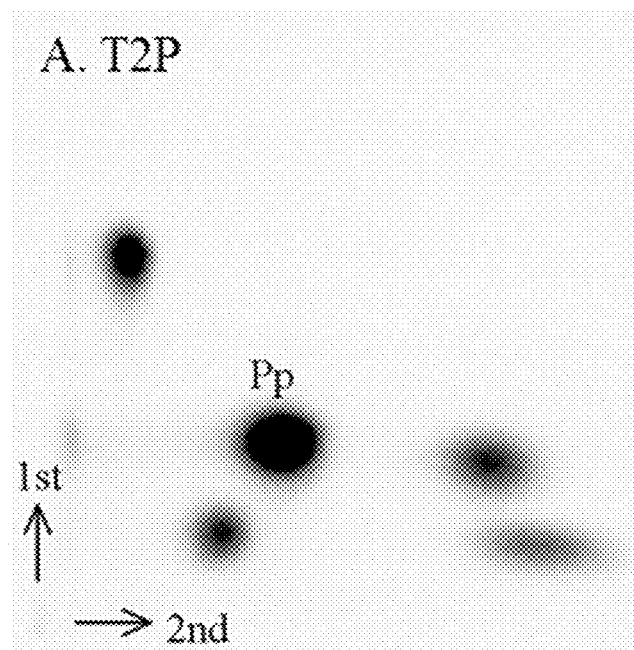
Figure 17:
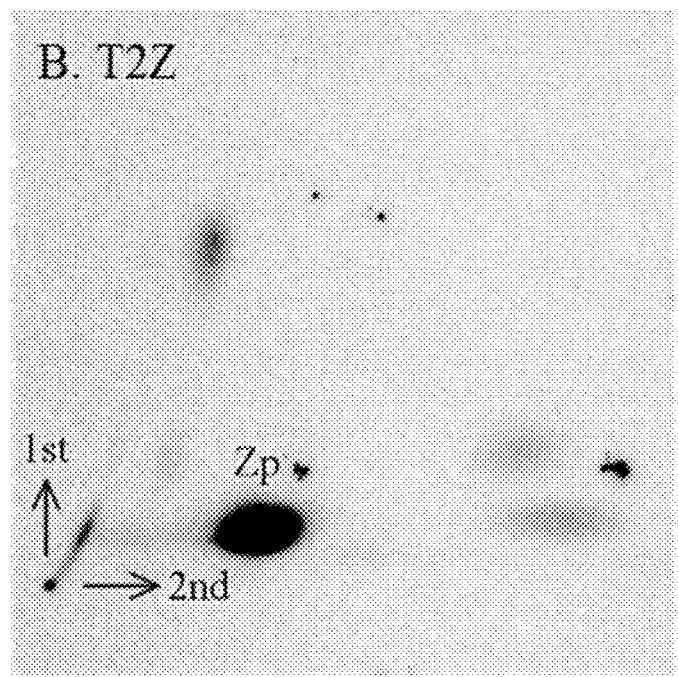
Figure 17:
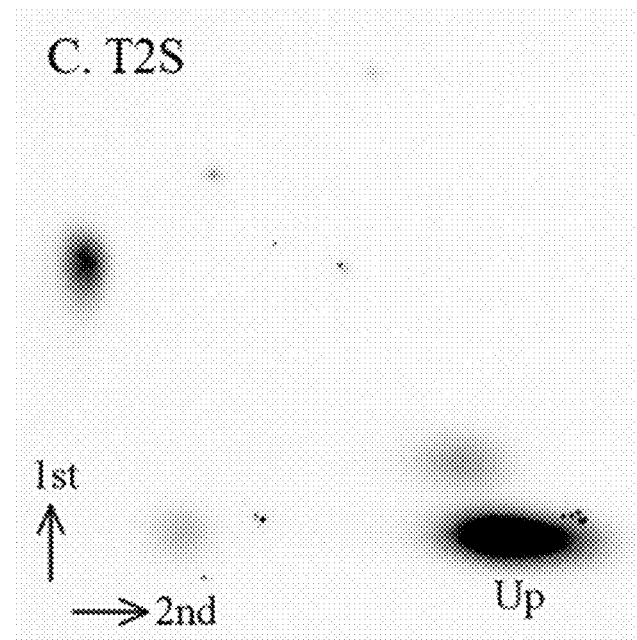
Figure 17:
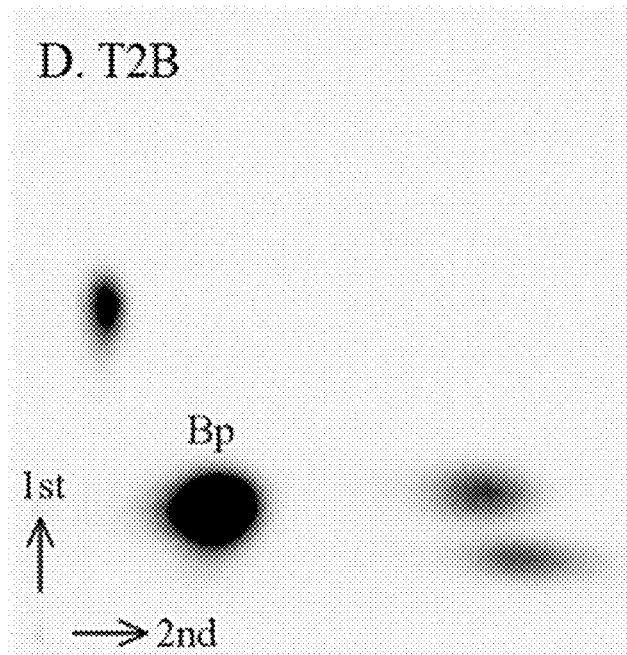
Figure 17:
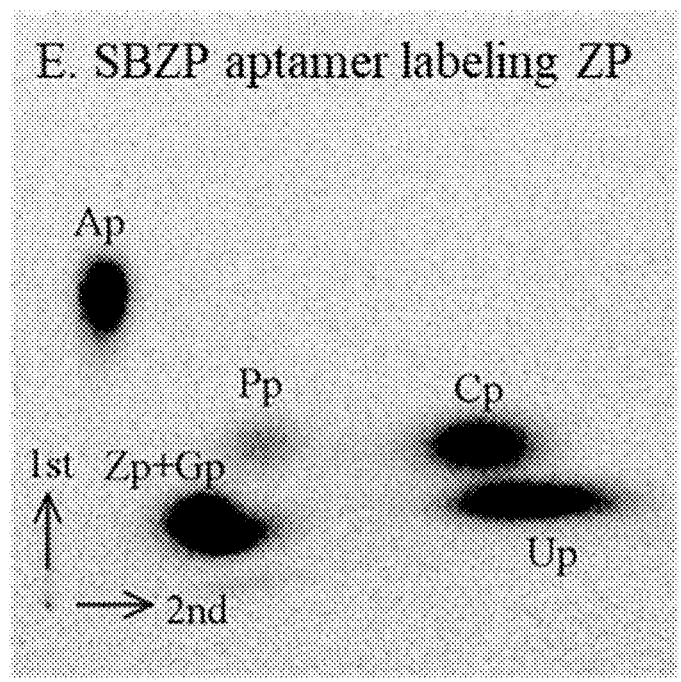
Figure 17:
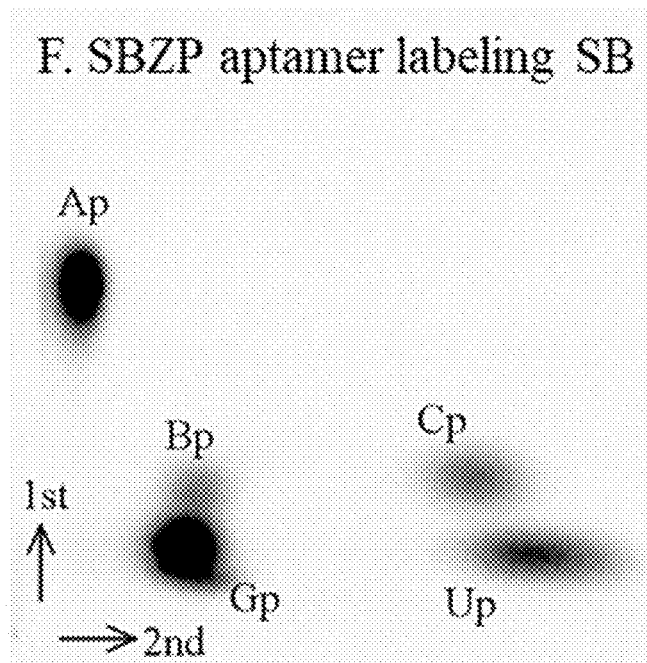

FIG. 17 A-FIG. 17 F. 2D-TLC of RNase T2 digests of labeled test sequences (panels A-D) and spinach (panels E and F) made with wild-type T7 RNA polymerase in secondary solvent system. (A) With template giving a product containing P as the only 8-letter non-standard nucleotide, generates P-3'-$^{32}$P (Pp) after digestion. (B) With template giving a product containing Z as the only 8-letter non-standard nucleotide, generates Z-3'-$^{32}$P (Zp) after digestion, which now runs much slower, separate from U-3'P. (C) With template that produces a product containing S as the only 8-letter non-standard nucleotide, essentially no amount of radioactivity is attributable to 5-3'-$^{32}$P. (D) With template giving a product containing B as the only 8-letter non-standard nucleotide, generates B-3'-$^{32}$P (Bp) after digestion. (E) Transcript of the spinach aptamer using alpha-$^{32}$P-GTP, which nearest neighbor labels all four standard nucleotides, as well as Z and P. After digestion, evidence of incorporation comes from the appearance of the corresponding Z-3'-$^{32}$P (Zp) and P-3'-$^{32}$P (Pp). (F) Transcript of the spinach aptamer using alpha-$^{32}$P-CTP, which nearest neighbor labels all four standard nucleotides, as well as S and B. After digestion, evidence of incorporation of BTP comes from the appearance of the corresponding B-3'-$^{32}$P (Bp). However, essentially no radioactivity are attributable to S-3'-$^{32}$P. This again suggests the need to use a variant of T7 RNA polymerase to allow the preparation of 8-letter RNA from 8-letter DNA by transcription.

Figure 18:
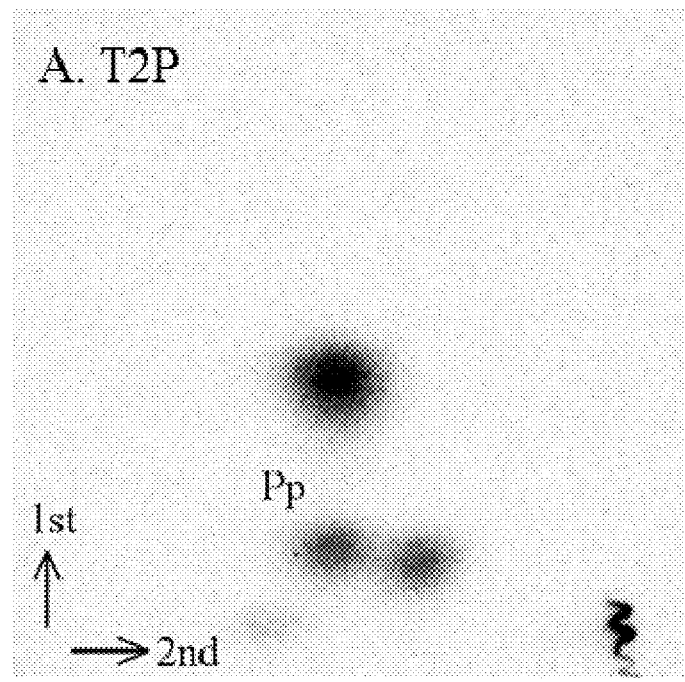
Figure 18:
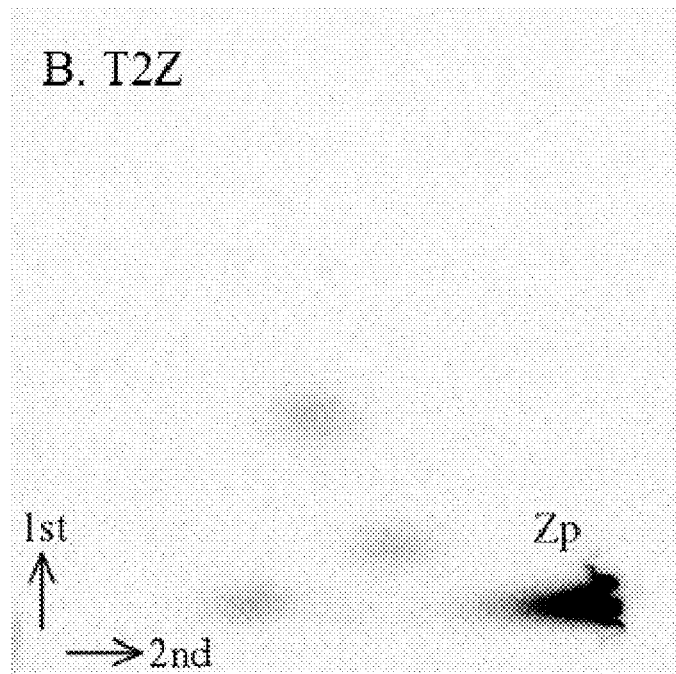
Figure 18:
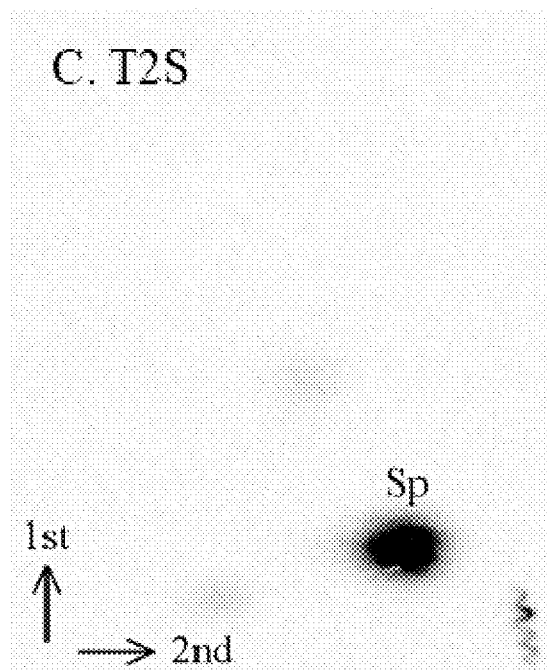
Figure 18:
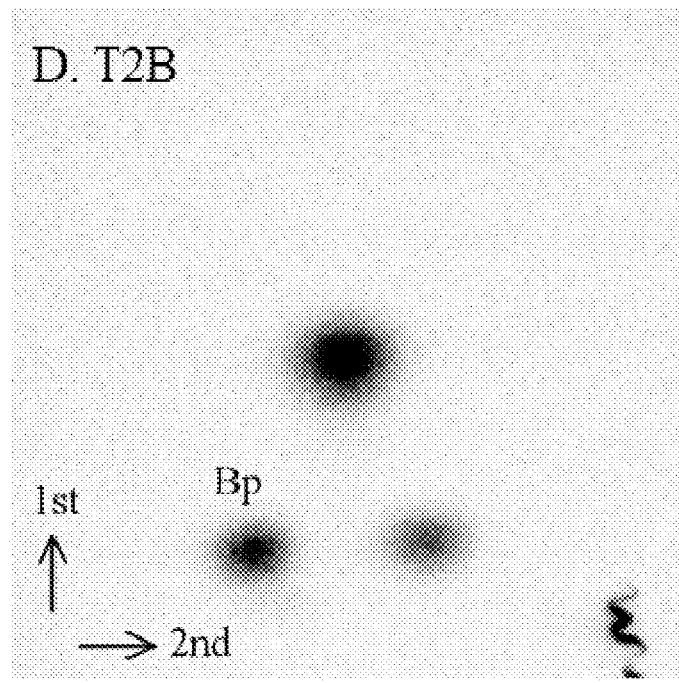
Figure 18:
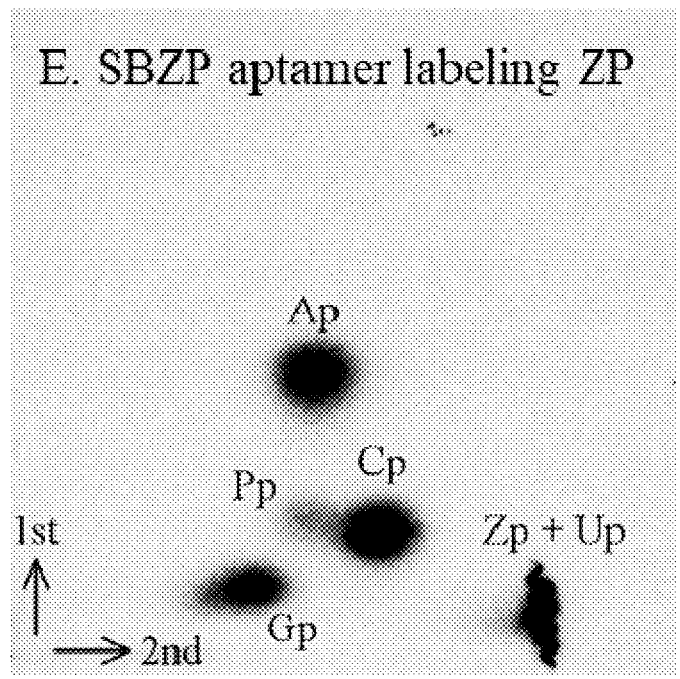
Figure 18:
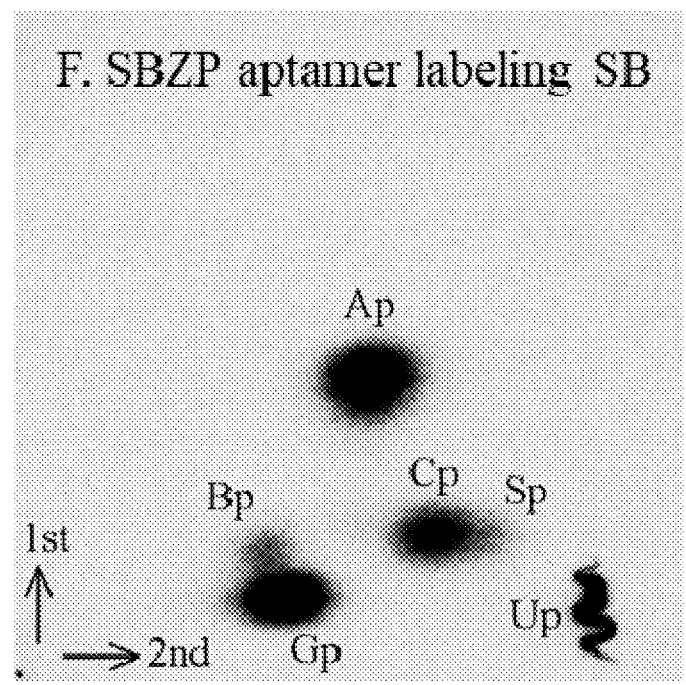

FIG. 18 A-FIG. 18 F. 2D-TLC of RNase T2 digests of labeled test sequences (panels A-D) and spinach (panels E and F) made with FAL variant of T7 RNA polymerase in primary solvent system. (A) With template giving a product containing P as the only 8-letter non-standard nucleotide, generates P-3'-$^{32}$P (Pp) after digestion. (B) With template giving a product containing Z as the only 8-letter non-standard nucleotide, generates Z-3'-$^{32}$P (Zp) after digestion, which runs with U-3'-P. (C) With template that produces a product containing S as the only 8-letter non-standard nucleotide, S-3'-$^{32}$P is now clearly present. (D) With template giving a product containing B as the only 8-letter non-standard nucleotide, generates B-3'-$^{32}$P (Bp) after digestion. (E) Transcript of the spinach aptamer using alpha-$^{32}$P-GTP, which nearest neighbor labels all four standard nucleotides, as well as Z and P. After digestion, evidence of incorporation comes from the appearance of the corresponding Z-3'-$^{32}$P (Zp) and P-3'-$^{32}$P (Pp). Since Z-3'-P does not separate convincingly in this system, its presence in the spinach aptamer was confirmed by HPLC (Figure E10). (F) With the spinach aptamer labeled with C-alpha-$^{32}$P-triphosphate, label of G, A, C, U, S, and B is expected. All six spots are seen in the amounts approximately as expected.

Figure 19:
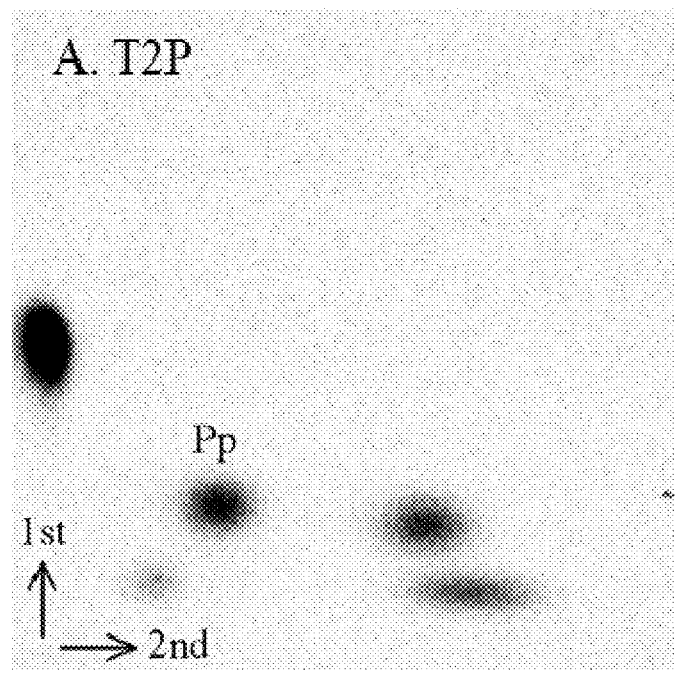
Figure 19:
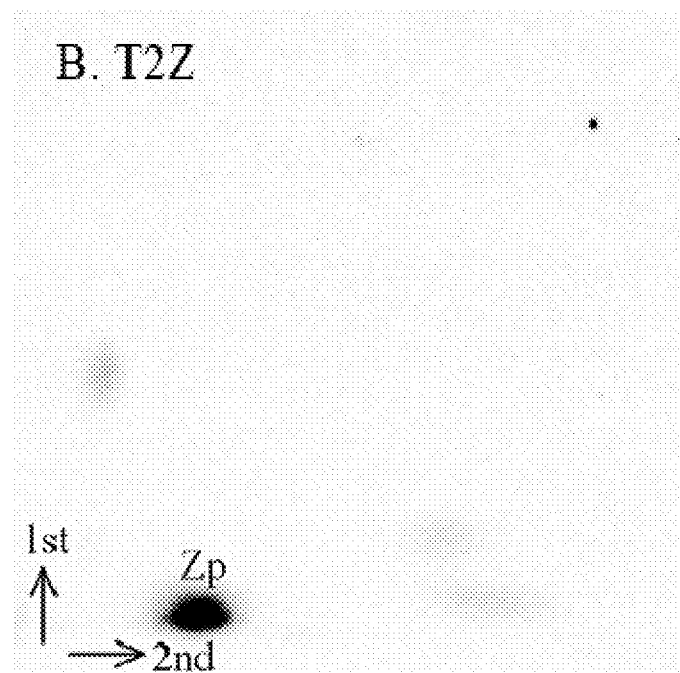
Figure 19:
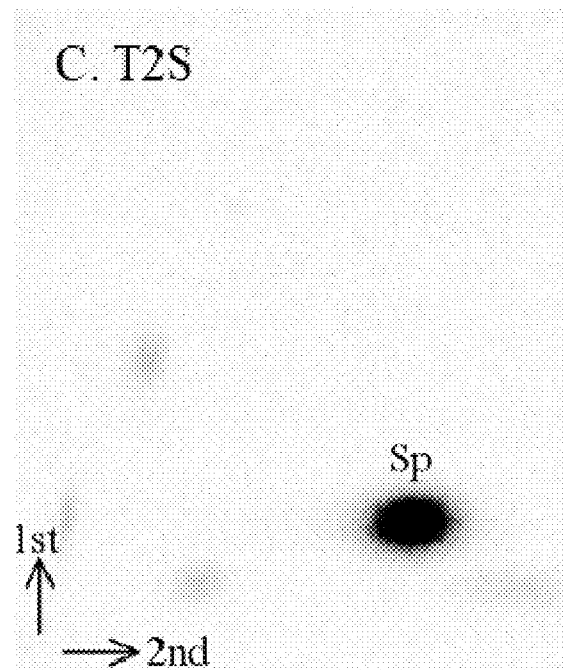
Figure 19:
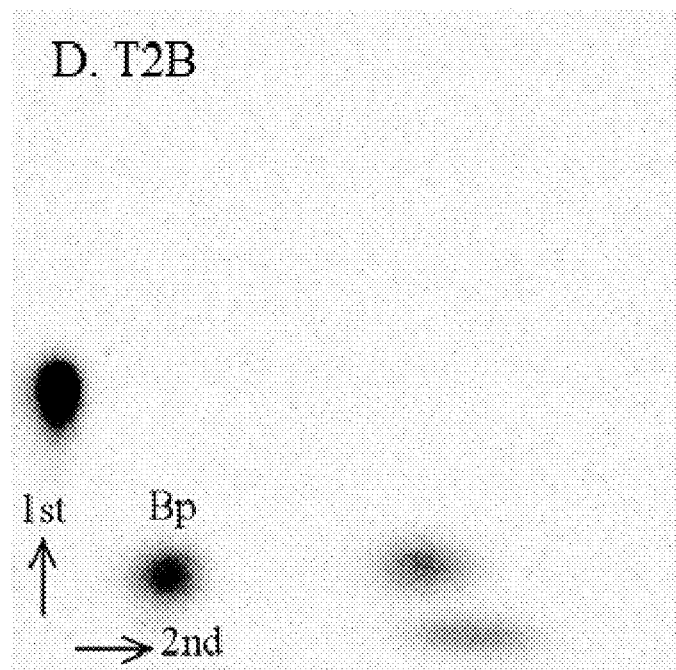
Figure 19:
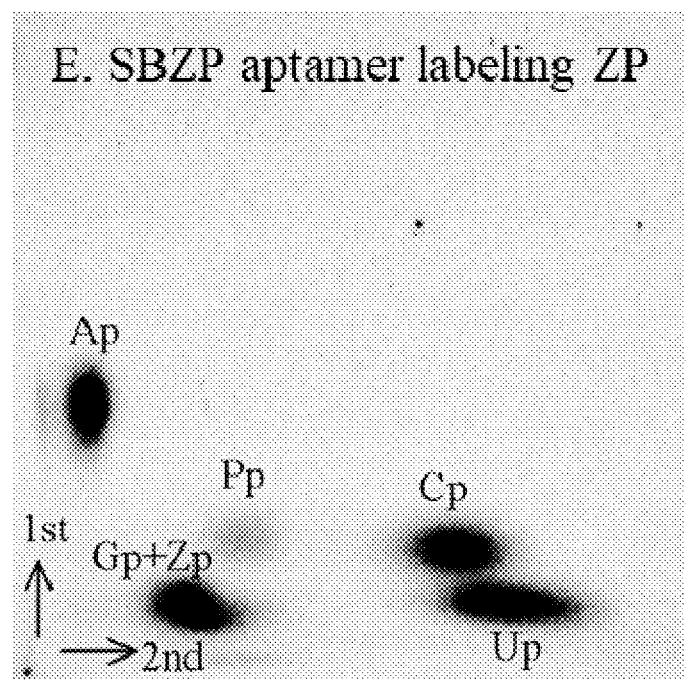
Figure 19:
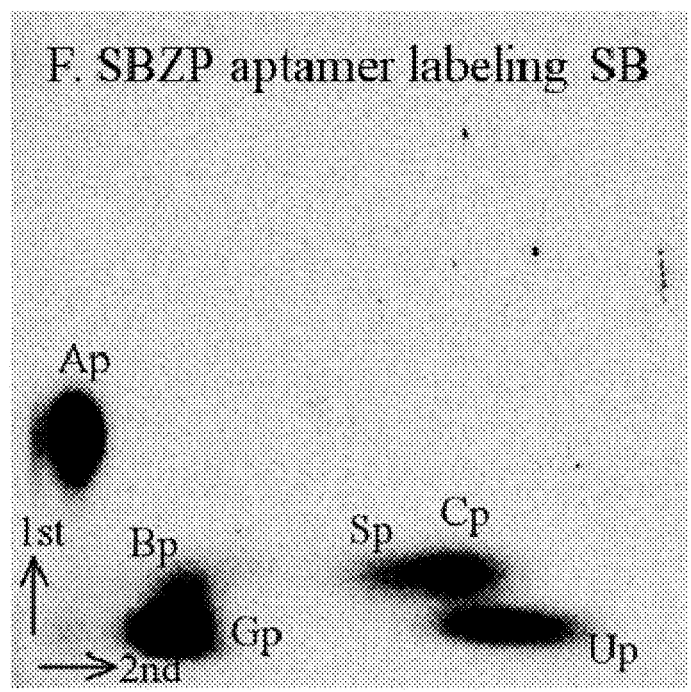

FIG. 19 A-FIG. 19 F. 2D-TLC of RNase T2 digests of labeled test sequences (panels A-D) and spinach (panels E and F) made with FAL variant of T7 RNA polymerase in secondary solvent system. (A) With template giving a product containing P as the only 8-letter non-standard nucleotide, generates P-3'-$^{32}$P (Pp) after digestion. (B) With template giving a product containing Z as the only 8-letter non-standard nucleotide, generates Z-3'-$^{32}$P (Zp) after digestion. (C) With template that produces a product containing S as the only 8-letter non-standard nucleotide, S-$^{32}$P-phosphate is again clearly present. (D) With template giving a product containing B as the only 8-letter non-standard nucleotide, generates B-3'-$^{32}$P (Bp) after digestion. (E) Transcript of the spinach aptamer using alpha-$^{32}$P-GTP, which nearest neighbor labels all four standard nucleotides, as well as Z and P. After digestion, evidence of incorporation comes from the appearance of the corresponding P-3'-$^{32}$P (Pp). Z-3'-$^{32}$P (Zp) running near G-3'-P; its incorporation was confirmed by HPLC (Figure E10). (F) With the spinach aptamer labeled with alpha-$^{32}$P-CTP, label of G, A, C, U, S, and B is expected. All six spots are seen with B-3'-$^{32}$P (Bp) running above G-3'-P and S-3'-P running to the left of C-3'-P.

DETAILED DESCRIPTION OF THE INVENTION

Figure 2:
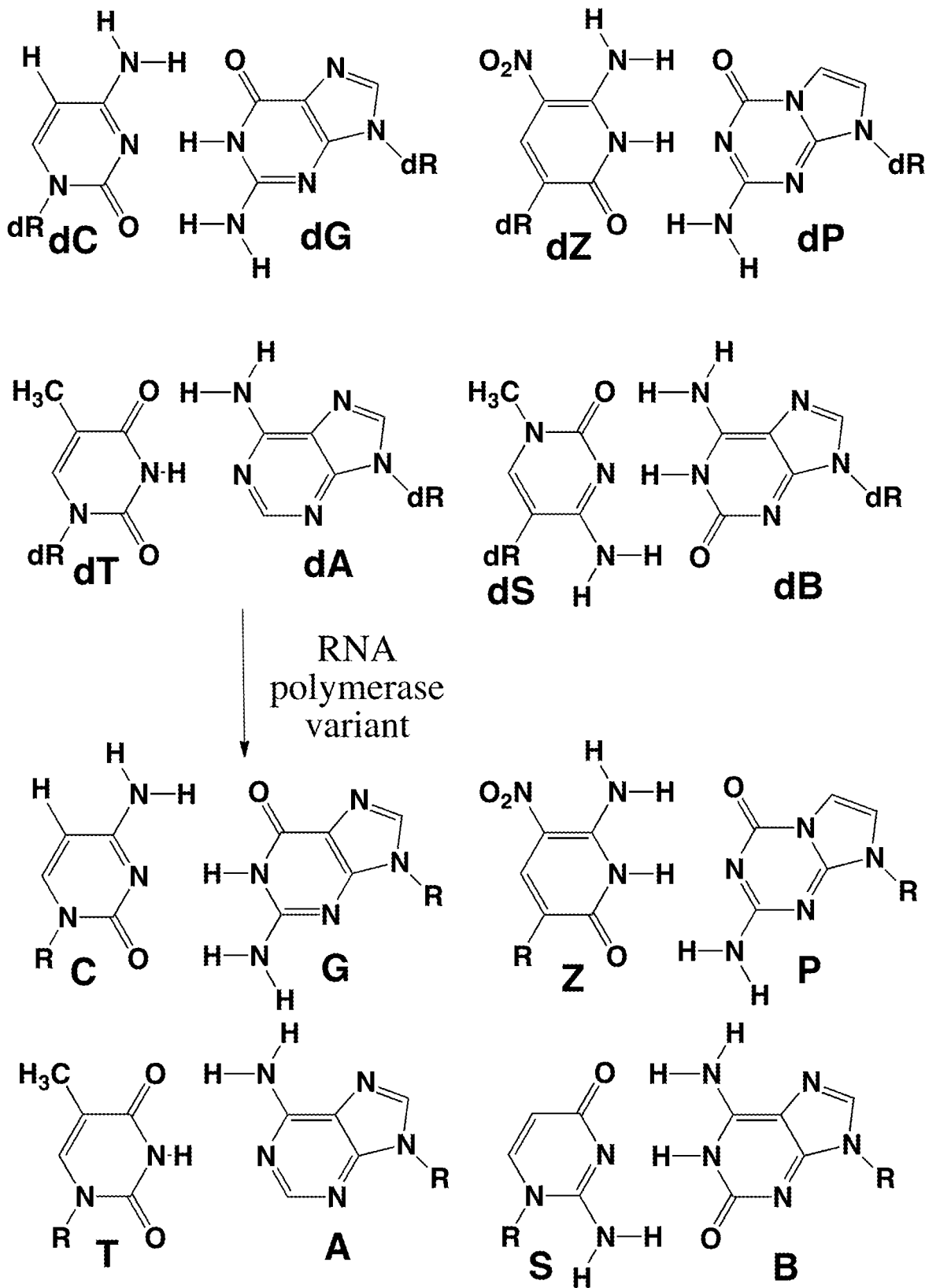
FIG. 2. The presently preferred nucleotides of the instant invention.

FIG. 2 shows the nucleotide nucleobases that are presently preferred in an 8-letter DNA-like system, and the nucleotide nucleobases that are presently preferred in an RNA system. To show that these eight letter systems can have utility as an information storage system, as with DNA and RNA, it must be shown that DNA analogs built from an arbitrarily large set of sequences form duplexes having predictable thermodynamic stability. This, in turn, requires determining the thermodynamic stability of an arbitrarily large number of duplexes, extracting thermodynamic binding parameters for individual pairs from them, and determining whether these yield a predictive model for the stability of duplexes. This was done following the procedure disclosed in Example 1.

With an eight-letter molecular recognition system, the number of possible dinucleotides is much larger than with just four. Considering duplex sequence symmetry, natural 4-letter DNA has ten unique base-pair dinucleotides, each with its own parameter [J. SantaLucia, Proc. Natl Acad. Sci. USA 95, 1460-1465 (1998)]. We represent these base-pair dinucleotides with a slash symbol (e.g. 5'-AC-3' paired with 3'-TG-5' is represented by AC/TG). These 10 dinucleotides are: AA/TT, AT/TA, TA/AT, AC/TG, AG/TC, CA/GT, GA/CT, CC/GG, GC/CG, and CG/GC J. [SantaLucia, Jr, Determination of nucleic acid thermodynamics by UV absorbance melting curves, in spectrophotometry and spectrofluorimetry: A practical approach (M. G. Gore, Ed.), Oxford U. Press (2000)]. Six other dinucleotides can be written (TT/AA, GT/CA, CT/GA, TG/AC, TC/ΔG, GG/CC), but due to duplex symmetry each of these is identical to one of the unique dinucleotides (e.g. AC/TG is equivalent to GT/CA). Two additional parameters improve predictions in 4-letter DNA. The first, a duplex initiation parameter, accounts for the decrease in translational degrees of freedom (an entropy penalty) when two strands become one duplex. The second parameter treats A:T pairs at the ends of duplexes specially.

A 6-letter DNA alphabet with S:B, T:A and C:G pairs adds to these 11 more NN dinucleotides, each with its own thermodynamic parameter, specifically (again considering symmetry) AS/TB, AB/TS, TS/AB, TB/AS, GS/CB, GB/CS, CS/GB, CB/GS, SS/BB, SB/BS, BS/SB. For 6-letter DNA having Z and P, 11 more NN dimers are again added, each with its own thermodynamic parameter (analogous to the SB dinucleotides given). Combining S:B and Z:P pairs in the same duplex adds four more NN dinucleotides, each with its own parameter: ZS/PB, ZB/PS, SZ/BP, and BZ/SP. Last, to get the same predictive power for 8-letter DNA as for standard DNA, 2 extra parameters are needed for S:B and Z:P pairs at the ends of duplexes. Thus, a total of 28 new parameters (i.e. unknowns) are needed; the 4-letter natural DNA code requires 12 parameters (for ten dinucleotides plus two for initiation and terminal A-T) whereas the 8-letter 8-letter DNA requires 40 parameters (for 36 dinucleotides plus four for initiation with terminal G:C and terminal effects for A:T, S:B, and Z:P).

As described in Example 1, protected phosphoramidites of two additional purine nucleoside analogs "P" and "B" and two additional pyrimidine analogs "Z" and "S" (Table 1, FIG. 1) were synthesized and used in solid-phase synthesis to create 94 short oligonucleotide duplexes. These were predicted to support P:Z and B:S pairing (FIG. 1) in addition to standard G:C and A:T pairing. Thermodynamic data for these 94 duplexes were collected by measuring UV absorbance (260 nm) as a function of temperature at six different DNA concentrations in saline buffer. These conditions, often used to study standard DNA, allow direct comparison between 8-letter parameters and parameters for 4-letter DNA. Data were processed using Meltwin v. 3.5 to obtain a parameter set using both the (Tm-1 vs. Ln(Ct)) method [J. SantaLucia Jr, D. H. Turner, Biopolymers 44, 309-319 (1997)] and the Marquardt non-linear curve fit method [J. SantaLucia, Jr, Determination of nucleic acid thermodynamics by UV absorbance melting curves, in spectrophotometry and spectrofluorimetry: A practical approach (M. G. Gore, Ed.), Oxford U. Press (2000)]. The error-weighted average of the values from the two methods yielded the thermodynamic values for the 94 duplexes that were used to determine the 28 new NN parameters and validate the quality of predictions [J. SantaLucia Jr, D. H. Turner, Biopolymers 44, 309-319 (1997); J. SantaLucia, Jr, Determination of nucleic acid thermodynamics by UV absorbance melting curves, in spectrophotometry and spectrofluorimetry: A practical approach (M. G. Gore, Ed.), Oxford U. Press (2000); H. T. Allawi, J. SantaLucia Jr, Biochemistry 36, 10581-10594 (1997)].

Figure 7:
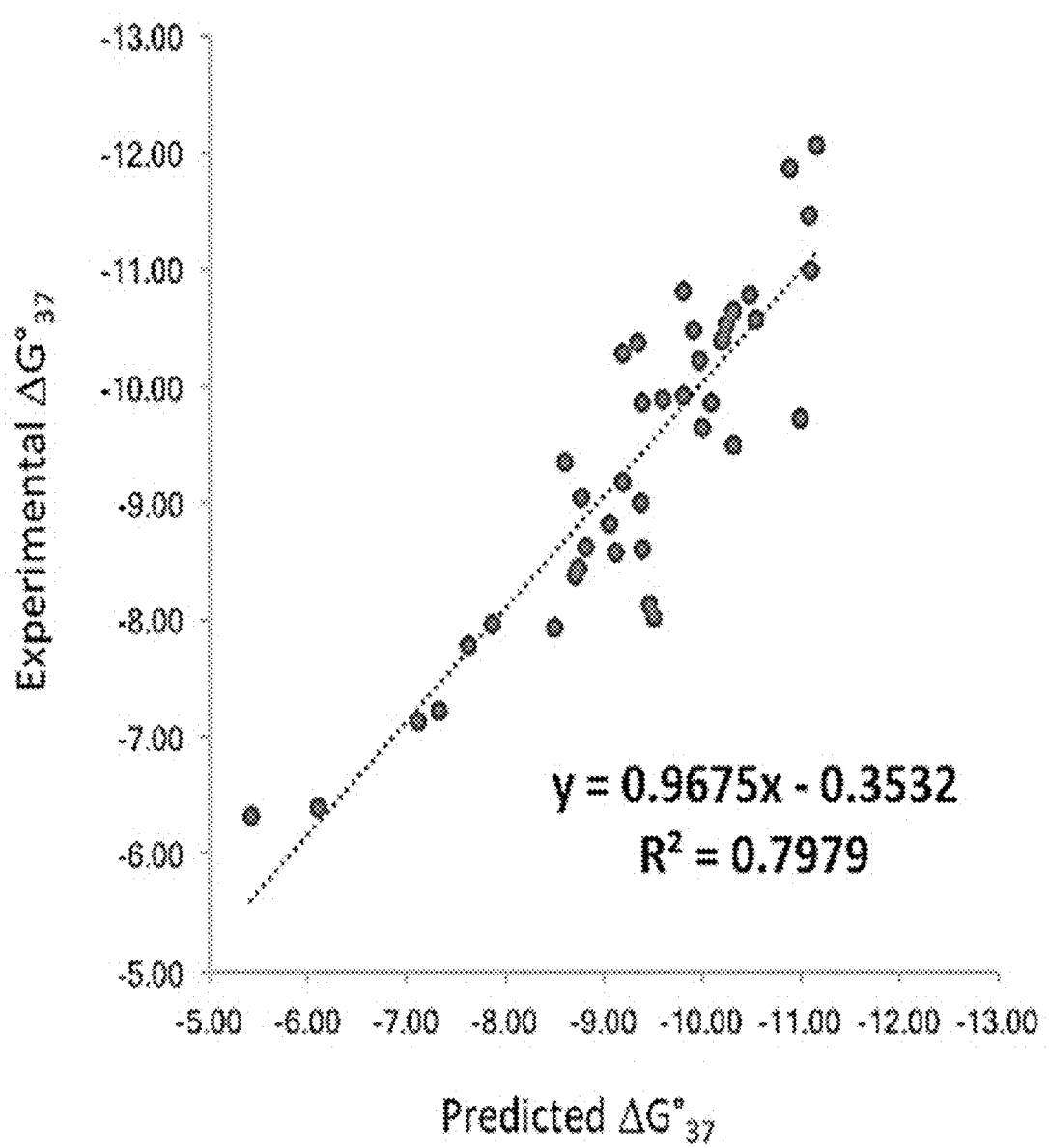
FIG. 7. Plot comparing the experimental free energy changes, $\Delta G°_{37}$, with the free energy changes predicted from the parameters determined here for the eight-letter DNA analog of the instant invention. These were generated for duplexes in this study (data in Table 3 and 4). NN parameters and standard errors, sigma, for Z-P containing NN dimers were derived by SVD and standard error propagation.

To determine the 12 new parameters involving combinations of G:C, A:T and Z:P pairs for the 6-letter GACTZP system, the duplex $\Delta G°$ 37 and $\Delta H°$ were measured for 41 duplexes (Table 4 and FIG. 7). The 12 new parameters involving combinations of G:C, A:T and B:S pairs for the 6-letter GACTBS system, the duplex $\Delta G°$ 37 and $\Delta H°$ were measured for 37 duplexes (Table 7 and FIG. 9). To determine the final 4 parameters for NN dimers with tandem B:S and Z:P pairs (i.e. ZS/PB, ZB/PS, SZ/BP, and BZ/SP) thermodynamics were measured for 15 duplexes (Table 9). FIG. 2 shows the agreement between experiments and predictions for the 8-letter system.

Figure 3:
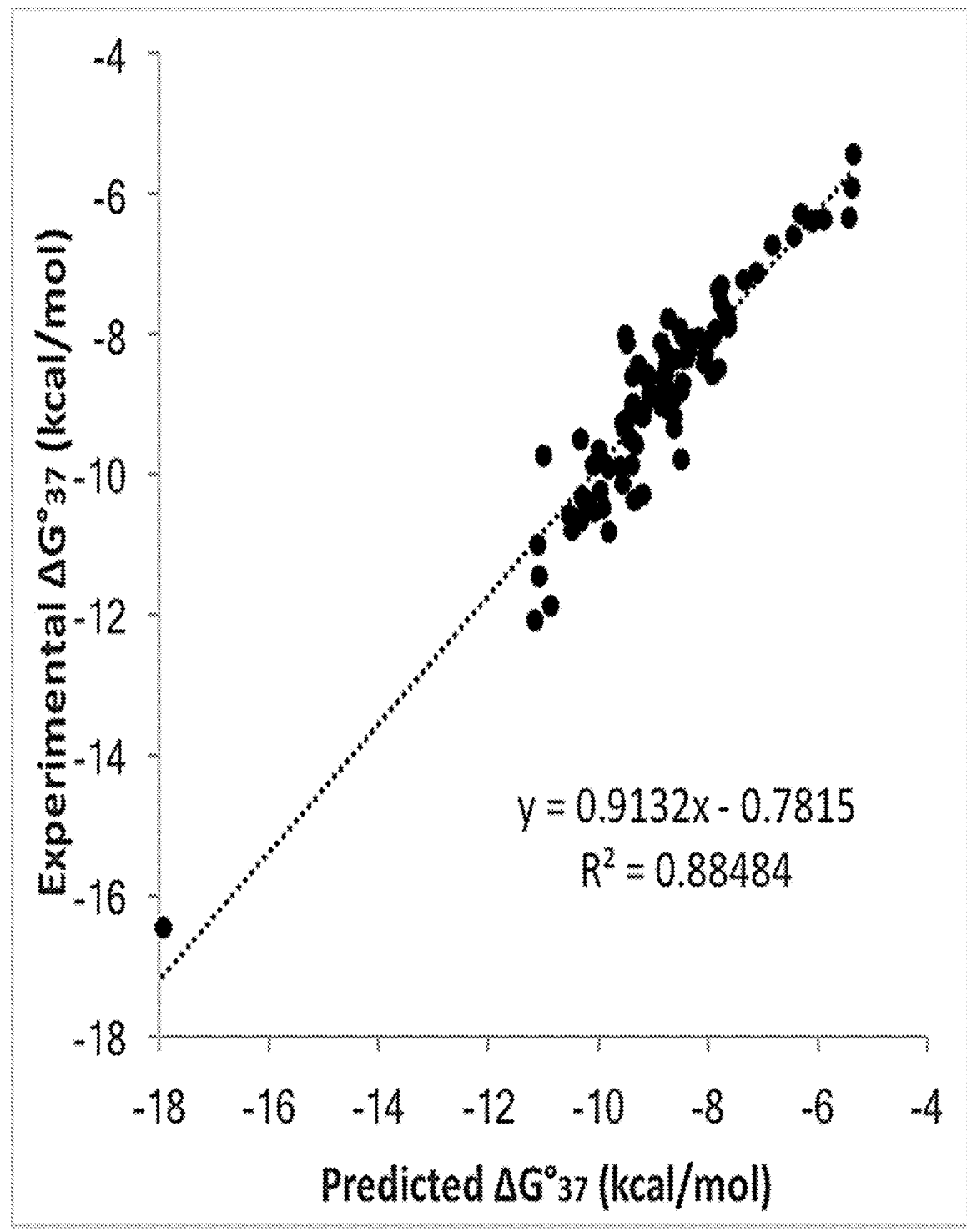
FIG. 3. A plot showing experiments and predictions for the 8-letter system of the instant invention. Plot of experimental vs. predicted free energy changes ($\Delta G°_{37}$) for 94 SBZP-containing 8-letter DNA duplexes.
Figure 4:
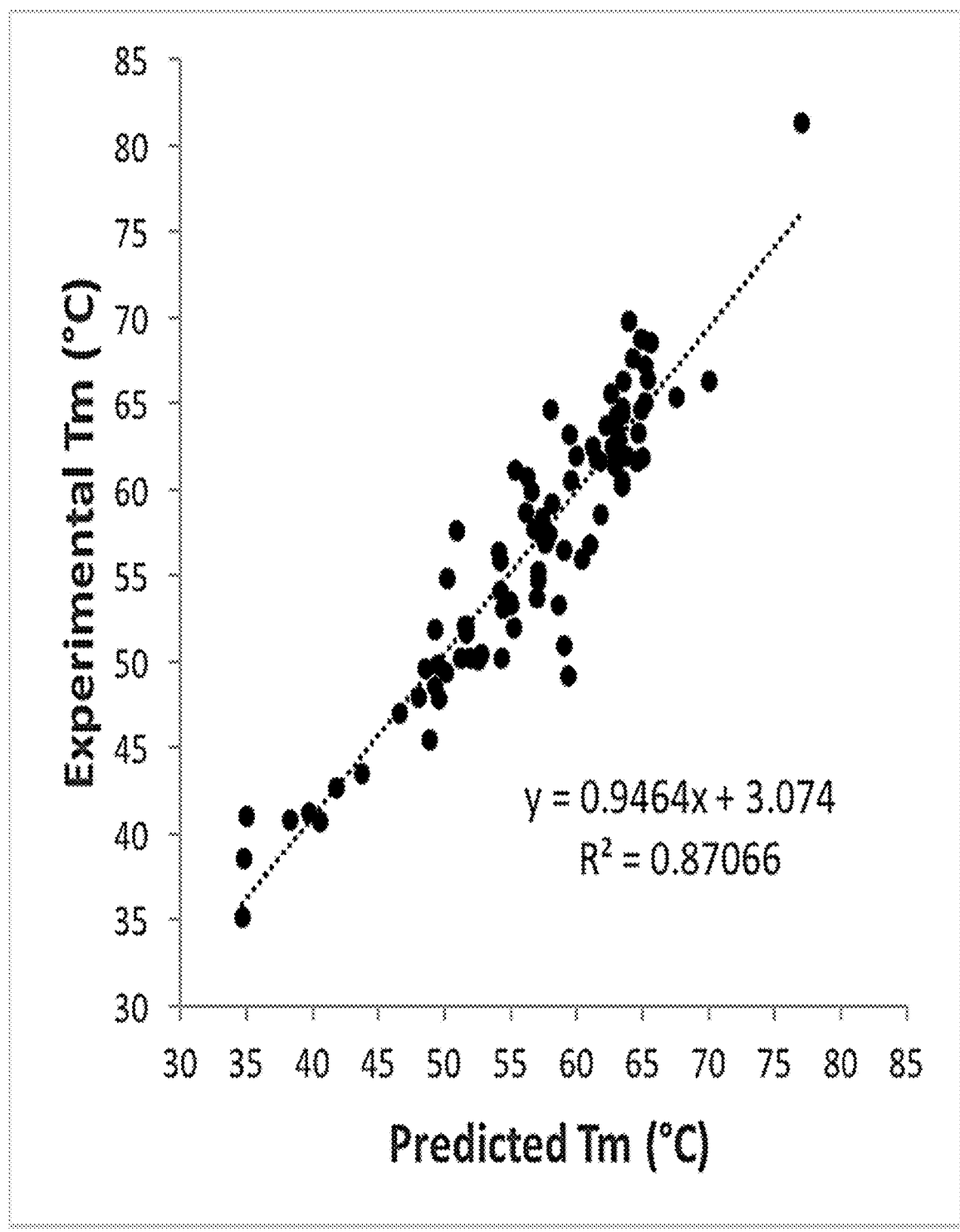
FIG. 4. Plot of experimental vs. predicted melting temperatures of 94 SBZP-containing 8-letter DNA duplexes in this study (data in Tables 3, 6, and 8).
Figure 8:
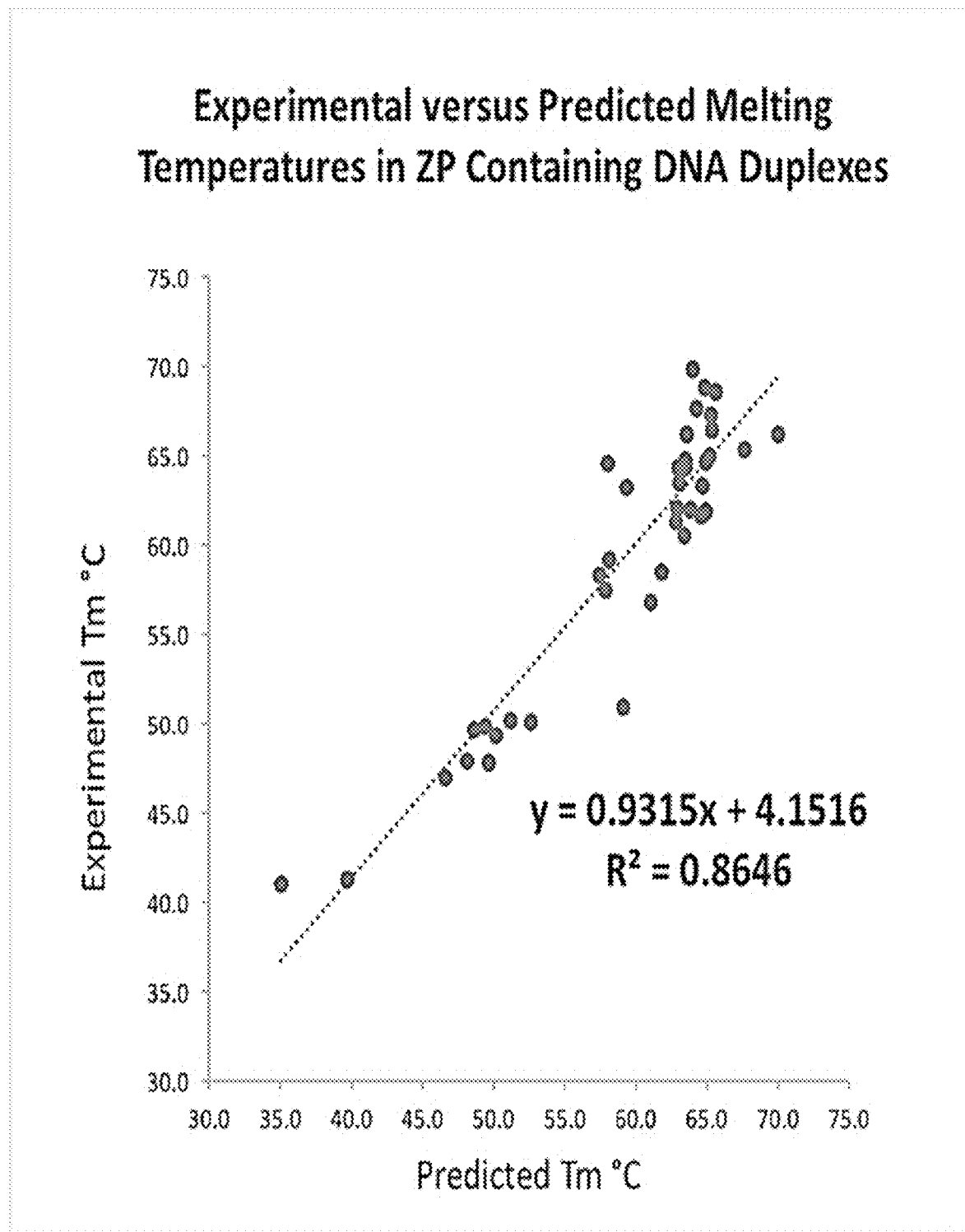
FIG. 8. Plot comparing the experimental melting temperatures vs. the predicted $T_m$'s for 41 Z-P containing DNA duplexes (data in Table 3 and 4). All $T_m$'s were calculated using a total oligonucleotide concentration of $1 \times 10^{-4}$ M.
Figure 10:
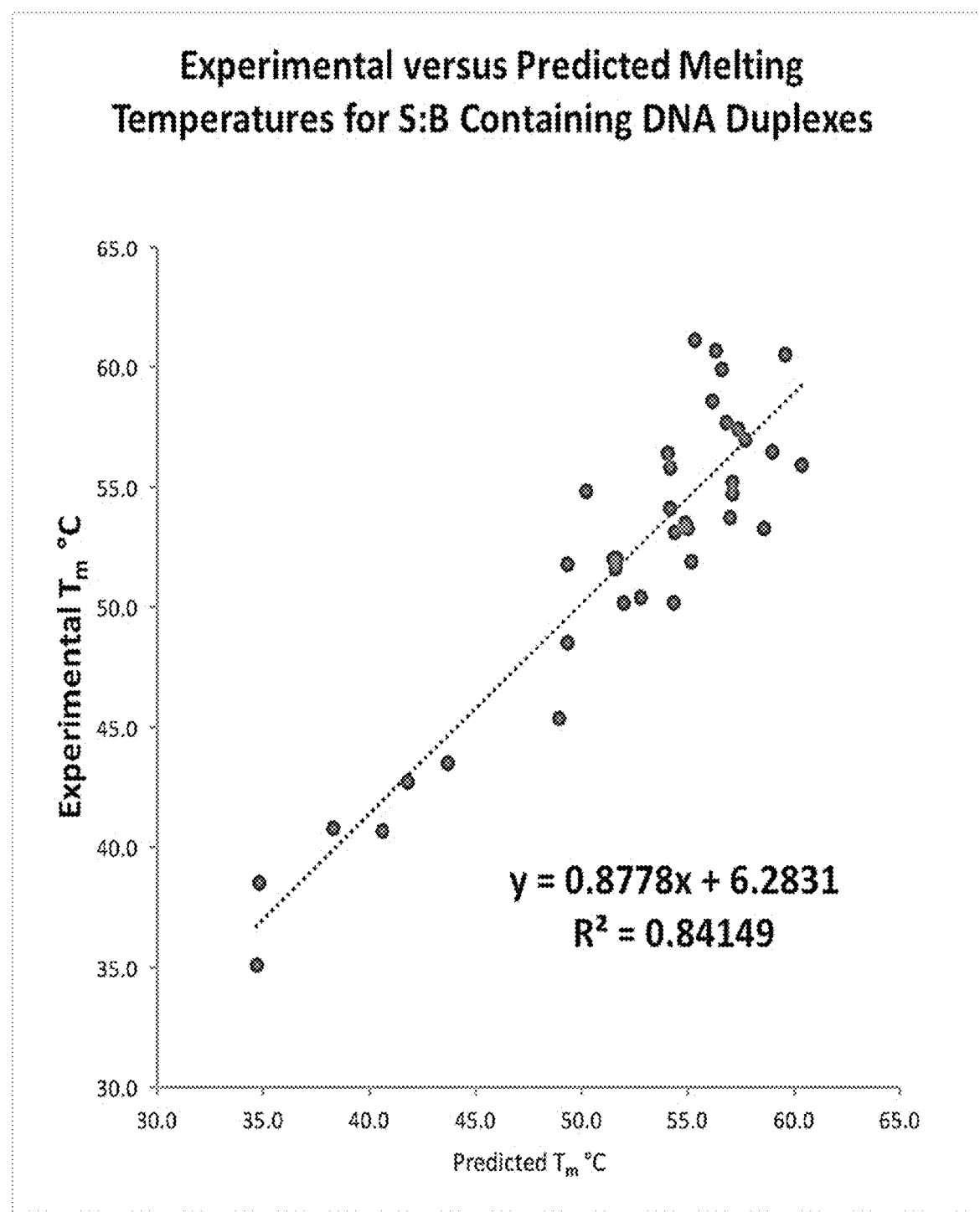
FIG. 10. Plot of the experimental melting temperatures vs. the predicted melting temperatures for all 37 S-B containing DNA duplexes (data in Table 6 and 7). All $T_m$'s were calculated using a total oligonucleotide concentration of $1 \times 10^{-4}$ M.
Figure 12:
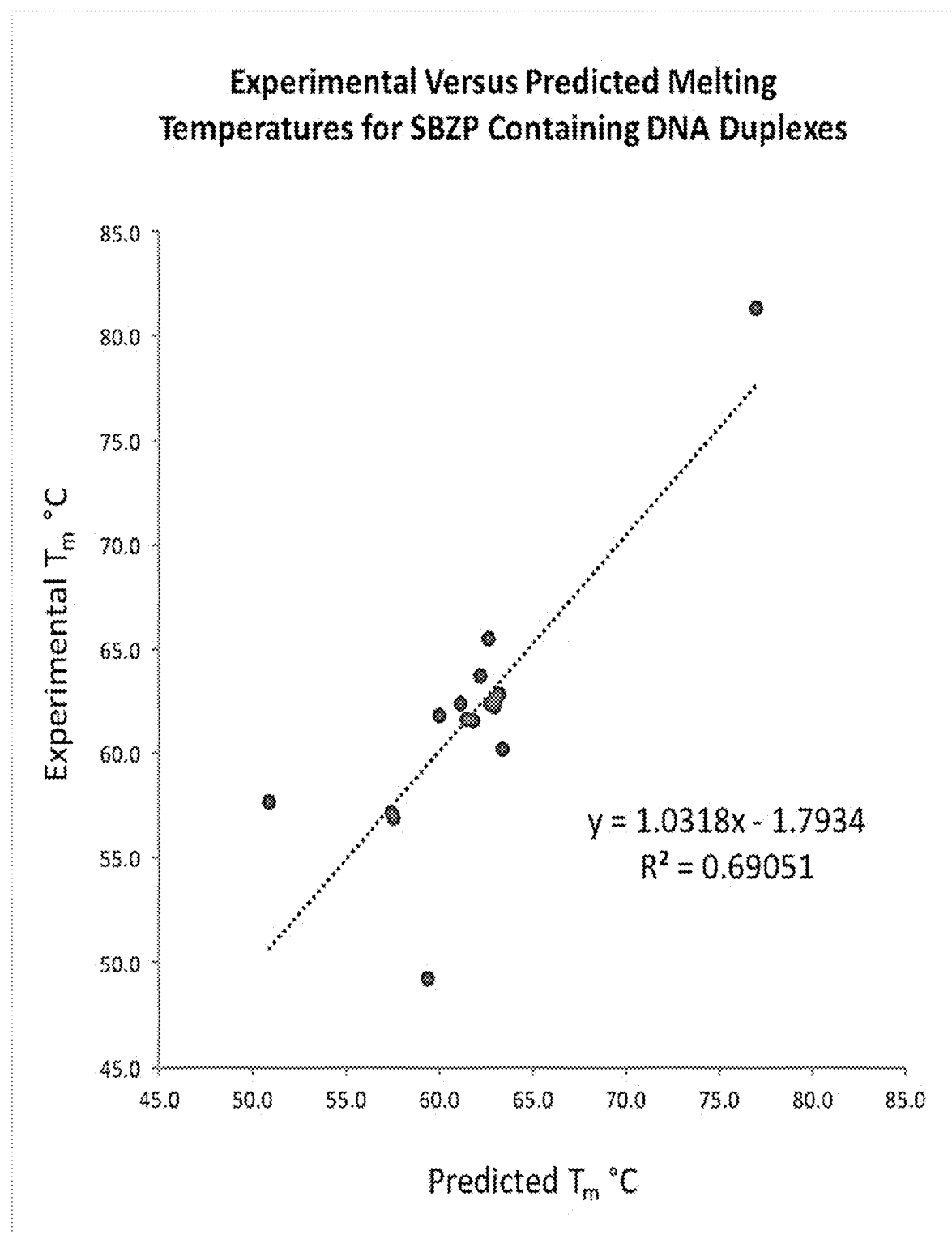
FIG. 12. Plot of experimental melting temperatures vs. predicted melting temperatures for all 15 S-B and Z-P dinucleotides in DNA duplexes (data in Table 9 and 10). All $T_m$'s were calculated using a total oligonucleotide concentration of $1 \times 10^{-4}$ M.

The thermodynamics for 94 8-letter duplexes synthesized from the 8-letter GACTSBZP DNA alphabet were then measured. These were used to obtain, and obtained best fit 28 parameters to these using singular value decomposition. Because this number of measurements over-determines these unknowns by a factor of 3.3, we were able to test the applicability of the NN model and to use error propagation to derive standard deviations in the derived parameters. The NN parameters FIG. 3 shows a plot of experimental versus the predicted free-energy changes based on software that incorporates the calculated nearest-neighbor thermodynamic parameters; FIG. 4 shows the same for the experimental and predicted melting temperatures; FIG. 8, FIG. 10 and FIG. 12 show data for ZP 6 letter system, SB 6 letter system, and SBZP 8 letter. The first plot has an R2 correlation of 0.89; the second plot has an R2 of 0.87. On average, the Tm is predicted within 2.1° C. and the $\Delta G°$ 37 is predicted within 0.39 kcal/mol for the 94 GACTZPSB 8-letter DNA duplexes in this study (data in Tables 3, 6, and 8). These errors are similar to those observed for the nearest-neighbor parameters for standard DNA/DNA duplexes [M. M. Georgiadis, I., Singh, I., W. F. Kellett, S. Hoshika, S. A. Benner, N. G. J. Richards, J. Am. Chem. Soc. 137, 6947-6955 (2015)]. Thus, GACTZPSB 8-letter DNA reproduces, but in expanded form, the molecular recognition behavior of standard 4-letter DNA at the level of solution biophysics.

Figure 5:
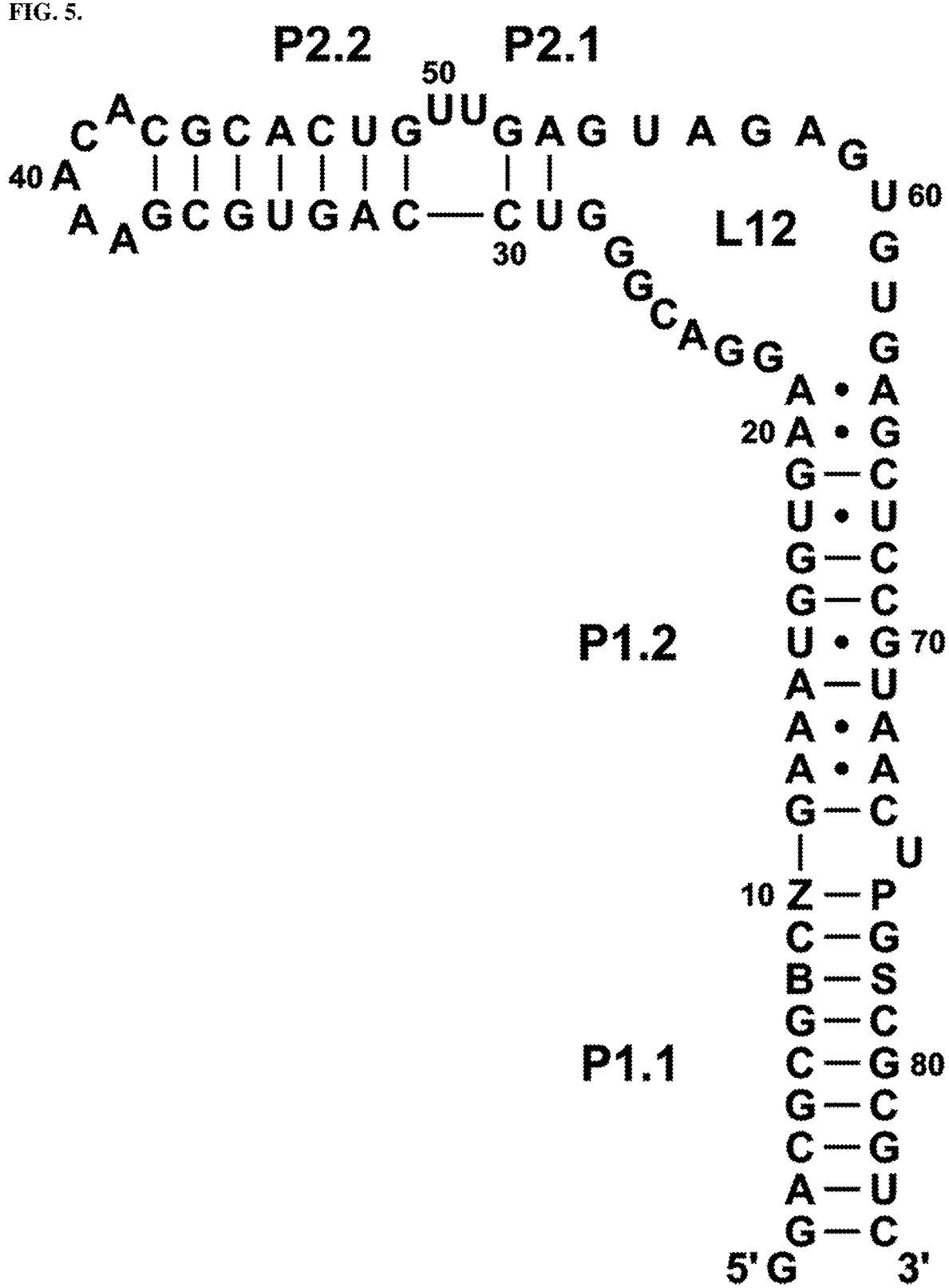
FIG. 5. Schematic showing an analog of a fluorescent aptamer known in the art as "spinach", with non-standard ribonucleotides Z, B, S, and P; SEQ ID NO 14.

Experiments described in Example 2 establish that DNA oligonucleotides containing (in addition to A, T, G, and C heterocycles) heterocycles that implement the S, B, Z, and P hydrogen bonding patterns can direct, by transcription, the synthesis of RNA transcript products that have (in addition to A, U, G, and C heterocycles) heterocycles that implement the B, S, P and Z hydrogen bonding patterns. DNA oligonucleotides containing a promoter for the T7 RNA polymerase containing one or more non-standard nucleotides were synthesized. These included templates that contained only one non-standard nucleotide components. Further, a longer template was synthesized that encoded the "spinach" fluorescent aptamer [X. J. Lu, W. K. Olson, Nucleic Acids Res. 31, 5108-5121 (2003)], an RNA molecule 84 nucleotides in length that folds and binds the fluor 3,5-difluoro-4-hydroxybenzylidene imidazolinone. Upon binding, the fluor fluoresces green. One of the designed 8-letter RNA aptamers is shown schematically in FIG. 5.

Procedures for the Transcription

To analyze the RNA transcripts, a set of analytical chemistry procedures were developed. These are described in Example 3. Central to these was "label shift" chemistry [J. S. Paige, K. Y. Wu, S. R. Jaffrey, Science 333, 642-646 (2010], which was adapted to allow analysis of 8-letter RNA. Here, one of four standard RNA triphosphates is introduced into a transcription mixture with an alpha-$^{32}$P label. This leads to a product with a bridging $^{32}$P-phosphate. Subsequent hydrolysis by ribonuclease T2 generates a mixture of nucleoside 3'-phosphates, where the 3'-nucleotide immediately preceding in the sequence carries a $^{32}$P-label. The mixture of nucleoside 3'-phosphates is then resolved by chromatography to determine the adjacency patters of the system.

To identify useful RNA polymerases, initial studies were done with DNA templates containing only one nonstandard nucleotide in the 8-letter system. These studies showed that wild-type T7 RNA polymerase readily incorporated riboZTP opposite template dP, riboPTP opposite template dZ, and riboBTP opposite template dS. However, riboSTP was not incorporated opposite template dB. Without wishing to be bound by theory, this might be attributed to the absence of electron density delivered to the minor groove by the aminopyridone heterocycle on S.

After substantial search, a T7 variant (H784A P266L Y639F) was discovered that was able to create RNA products that contain riboS, and RNA transcript products that contained all eight non-standard and standard nucleotides. This variant had been reported previously as able to accept modified 2'-ribose triphosphates without early termination or substantial infidelity, an unnatural structural difference different than the one proposed here [I. Hirao, T. Ohtsuki, T. Fujiwara, T. Mitsui, T. Yokogawa, T. Okuni, H. Nakagawa, K. Takio, T. Yabuki, T. Kigawa, K. Kodama, T. Yokogawa, K. Nishikawa, S. Yokoyama, Nature Biotechnol. 20, 177 (2002)]. Label shift experiments are described that specific incorporation of all four non-standard components of the 8-letter system into transcripts.

Figure 6:
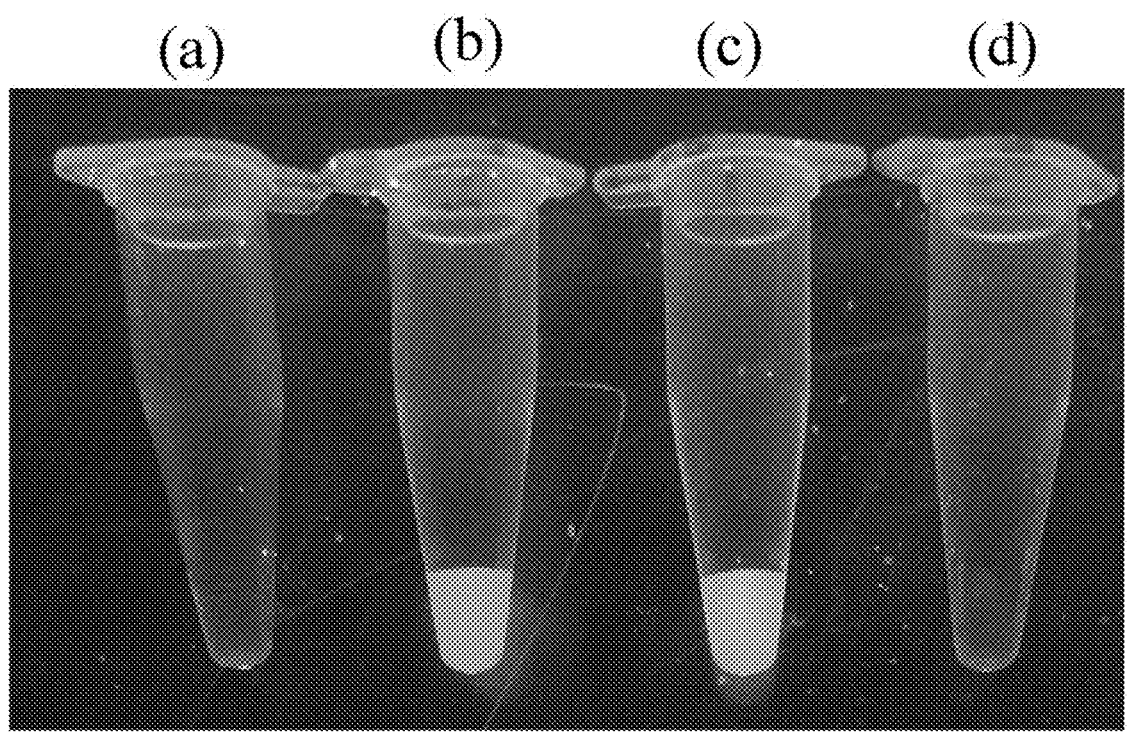
FIG. 6. Fluorescence of the 8-letter spinach construct. From left to right: (a) native spinach aptamer with fluor, (b) fluor and spinach aptamer containing Z at position 50, near the fluor, which binds in L12, (c) Control with fluor only, lacking RNA, and (d) full 8-letter spinach having the sequence shown in the left panel. Images are created under 400 nm light with an orange filter.

The full length 8-letter spinach variant was then prepared from the synthetic 8-letter DNA sequence placed behind a T7 promoter, isolated by gel electrophoresis, and studied. Notably, it fluoresced green when complexed to the fluor (FIG. 6). A number of variants of spinach lacking non-standard components of the 8-letter system were also prepared and studied. Of particular interest, placing 8-letter Z in the fold near the fluor quenched fluorescence, likely because Z's aminonitropyridone ring quenches fluorescence generally; analysis of the structure of native spinach suggested that the replacement did.

Figure 1:
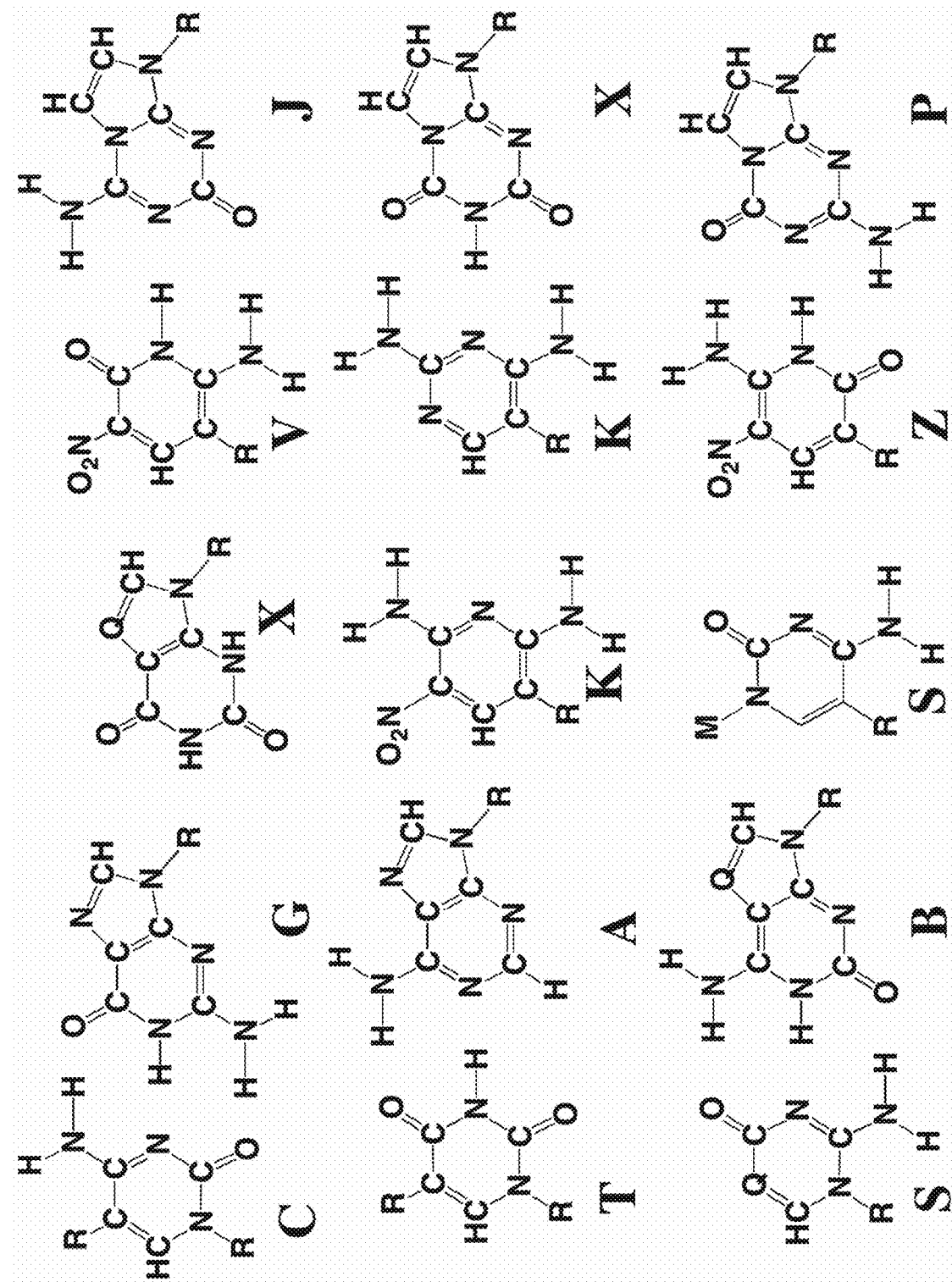
FIG. 1. Non-standard nucleotides of the instant invention. Where Q=C—H (carbon-hydrogen), or C-M (carbon-M), or N, where M is an alkyl, alkenyl, or alkynyl substituent, either simple or functionalized. Note how the four standard nucleotides (labeled G, A, C, and T) all deliver electron density to the minor groove from their purine N7 or the exocyclic oxygen of the purines. Note how the heterocycle of the non-standard pyrimidine analog labeled Z also does so, but that the pyrimidine analogs labeled S, K, and V do not, nor does the implementation of the X hydrogen bonding pattern with a "Q" at position 7.

This result shows that the FAL variant of T7 RNA polymerase can incorporate riboSTP, notwithstanding the fact that the heterocycle on riboSTP does not have a moiety that delivers electron density to the minor groove. It is thus taught that the FAL variant will also incorporate riboKTP (in two forms, shown in FIG. 1), riboVTP (FIG. 1), and two forms of riboXTP (FIG. 1, but only the structures with Q).

In addition to allowing the synthesis by transcription of RNA molecules containing S, this invention makes available, also for the first time, an informational system that is built from eight different building blocks. This system has substantially increased information density; while a duplex with 10 nucleobase pairs built from a 4-letter alphabet has only 1,048,576 ($=4^{10}$) different sequences, a duplex built from an 8-letter alphabet has 1,073,741,824 ($=8^{10}$) different sequences. In terms of computer science bits, this doubles the information density of a DNA-like biopolymer. Further, detailed biophysical analysis of duplex suggests that the 8-letter molecular system has regular thermodynamic properties, just as four-letter DNA Such greater information storage capacity may have application in bar-coding and combinatorial tagging, computer retrievable information storage, and self-assembling nano-structures. Further, the fact that the number of letters in DNA can be doubled using a design theory that incorporates both hydrogen bonding and size complementarity increases confidence that the non-abridged Watson-Crick model reflects reality. Last, 8-letter DNA may now serve as a platform for more demanding goals in synthetic biology. One of these seeks to use the added information density to encode more amino acids in ribosome-based transcription.

EXAMPLES

Example 1. Thermodynamic Parameters for an 8-Letter DNA-Like System ("8-Letter DNA")

Synthesis and purification of AEGIS oligonucleotides Standard phosphoramidites (Bz-dA, Ac-dC, dmf-dG, and dT) and dB (isoG) phosphoramidite and CPG having standard residues were obtained from Glen Research (Sterling, Va.). The phosphoramidites of dZ, dP and dS were obtained from Firebird Biomolecular Sciences LLC (Alachua, Fla.).

S was 3-methyl-6-amino-5-(1'-beta-D-2'-deoxyribofuranosyl)-pyrimidin-2-one

B was 6-amino-9-(1'-beta-D-2'-deoxyribofuranosyl)-4-hydroxy-5-(hydroxymethyl)-oxolan-2-yl]-1H-purin-2-one Z was 6-amino-3-(2'-deoxy)-D-ribofuranosyl)-5-nitro-1H-pyridin-2-one P was 2-amino-8-(beta-D-2'-deoxyribofuranosyl)-imidazo-[1,2a]-1,3,5-triazin-[8H]-4-one All oligonucleotides containing non-standard 8-letter components were synthesized on an ABI 394 DNA Synthesizer following standard phosphoramidite chemistry. The CPGs having oligonucleotides were treated with 2.0 mL of 1 M DBU in anhydrous acetonitrile at room temperature for 24 hours to deprotect the NPE group on the dZ nucleobase. Then the CPGs were filtered, dried, and treated with concentrated ammonium hydroxide at 55° C. for 16 hours. After removal of ammonium hydroxide, the AEGIS oligonucleotides were purified on ion-exchange HPLC, and then desalted using Sep-Pac® Plus C18 cartridges (Waters). These are collected in Table 1.

TABLE 1

Sequences of 6-letter and 8-letter DNA analogs used to obtain usefully predictive thermodynamic parameters. Non-standard components are represented as bold letters.

| Name | Sequence | Name | Sequence |
|---|---|---|---|
| a) 6-letter oligonucleotides containing S and B. | | | |
| SB-1 | 5'-GGS ATB CC | SB-20 | 5'-SAC TAG TB |
| SB-2 | 5'-GCB ATS GC | SB-21 | 5'-GAC BSG TC |
| SB-3 | 5'-GGS TAB CC | SB-22 | 5'-GAC SBG TC |
| SB-4 | 5'-GCB TAS GC | SB-23 | 5'-GTG BSC AC |
| SB-5 | 5'-GAS CGB TC | SB-24 | 5'-GTG SBC AC |
| SB-6 | 5'-GTS CGB AC | SB-25 | 5'-GCA BST GC |
| SB-7 | 5'-GAS ATB TC | SB-26 | 5'-GCT BSA GC |
| SB-8 | 5'-GAB ATS TC | SB-27 | 5'-GCA SBT GC |
| SB-9 | 5'-GAS TAB TC | SB-28 | 5'-GCT SBA GC |
| SB-10 | 5'-GTS ATB AC | SB-29 | 5'-GSS ATB BC |
| SB-11 | 5'-GBC ATG SC | SB-30 | 5'-GSS TAB BC |
| SB-12 | 5'-GSG ATC BC | SB-31 | 5'-CBB ATS SG |
| SB-13 | 5'-CSC ATG BG | SB-32 | 5'-GAS SBB TC |
| SB-14 | 5'-CST CGA BG | SB-33 | 5'-GTB BSS AC |
| SB-15 | 5'-CSA CGT BG | SB-34 | 5'-GGA SBT CC |
| SB-16 | 5'-CBG ATC SG | SB-35 | 5'-GSA CGT BC |
| SB-17 | 5'-BGC ATG CS | SB-36 | 5'-GGA BST CC |
| SB-18 | 5'-SGC ATG CB | SB-37 | 5'-GBT CGA SC |
| SB-19 | 5'-BAC TAG TS | | |
| b) 6-letter oligonucleotides containing Z and P. | | | |
| ZP-1 | 5'-GGZ ATP CC | ZP-22 | 5'-GAC ZPG TC |
| ZP-2 | 5'-GCP ATZ GC | ZP-23 | 5'-GTG PZC AC |
| ZP-3 | 5'-GGZ TAP CC | ZP-24 | 5'-GTG ZPC AC |
| ZP-4 | 5'-GCP TAZ GC | ZP-25 | 5'-GCA PZT GC |
| ZP-5 | 5'-GAZ CGP TC | ZP-26 | 5'-GCT PZA GC |
| ZP-6 | 5'-GTZ CGP AC | ZP-27 | 5'-GCA ZPT GC |
| ZP-7 | 5'-GAZ ATP TC | ZP-28 | 5'-GCT ZPA GC |
| ZP-8 | 5'-GAP ATZ TC | ZP-29 | 5'-GZZ ATP PC |
| ZP-9 | 5'-GAZ TAP TC | ZP-30 | 5'-GZZ TAP PC |
| ZP-10 | 5'-GTZ ATP AC | ZP-31 | 5'-CPP ATZ ZG |
| ZP-11 | 5'-GPC ATG ZC | ZP-32 | 5'-PGA CGT CZ |
| ZP-12 | 5'-GZG ATC PC | ZP-33 | 5'-GGA ZPT CC |
| ZP-13 | 5'-CZC ATG PG | ZP-34 | 5'-GPA CGT ZC |
| ZP-14 | 5'-CZT CGA PG | ZP-35 | 5'-GGA PZT CC |
| ZP-15 | 5'-CZA CGT PG | ZP-36 | 5'-GCC APT TAA |
| | | | 3'-CGG TZA ATT |

TABLE 1-continued

Sequences of 6-letter and 8-letter
DNA analogs used to obtain
usefully predictive thermodynamic
parameters. Non-standard components
are represented as bold letters.

| Name | Sequence | Name | Sequence |
|---|---|---|---|
| ZP-16 | 5'-CPG ATC ZG | ZP-37 | 5'-GCZ AGT TAA<br>3'-CGP TCA ATT |
| ZP-17 | 5'-PGC ATG CZ | ZP-38 | 5'-GZC AGT TAA<br>3'-CPG TCA ATT |
| ZP-18 | 5'-ZGC ATG CP | ZP-39 | 5'-GZZ AGT TAA<br>3'-CPP TCA ATT |
| ZP-19 | 5'-PAC TAG TZ | ZP-40 | 5'-GAZ ZPP TC |
| ZP-20 | 5'-ZAC TAG TP | ZP-41 | 5'-GTP PZZ AC |
| ZP-21 | 5'-GAC PZG TC | | | c) 8-letter oligonucleotides
containing S, B, Z and P.

| | | | |
|---|---|---|---|
| SBZP-1 | 5'-CSZ ATP BG | SBZP-9 | 5'-GSZ ATP BC |
| SBZP-2 | 5'-CSP ATZ BG | SBZP-10 | 5'-GSP ATZ BC |
| SBZP-3 | 5'-CZS ATB PG | SBZP-11 | 5'-GZS ATB PC |
| SBZP-4 | 5'-CZB ATS PG | SBZP-12 | 5'-GZB ATS PC |
| SBZP-5 | 5'-CSZ TAP BG | SBZP-13 | 5'-GAZ SBP TC |
| SBZP-6 | 5'-GSP TAZ BC | SBZP-14 | 5'-GTP BSZ AC |
| SBZP-7 | 5'-GZS TAB PC | SBZP-15 | 5'-CBZ ATP SG |
| SBZP-8 | 5'-CZB TAS PG | SBZP-16 | 5'-GBZ TAP SC |

Thermodynamics Methods

Thermodynamics were determined for duplexes containing S:B and Z:P base pairs by measuring UV absorbance versus temperature profiles over six different oligonucleotide concentrations in buffer containing 1M NaCl, 10 mM Na$_2$HPO$_4$, and 0.5 mM Na$_2$EDTA, pH 7.00 (referred to as "1M NaCl buffer"). These data were then processed using *Meltwin v.* 3.5 to obtain a full thermodynamic parameter set through two different methods: $T_m^{-1}$ vs. Ln(Ct) method and the Marquardt non-linear curve fit method (Table 4, Table 7, and Table 10). A duplex denaturation data set was considered to be two-state if the two methods yield ΔH° values that are within 15% of each other [H. T. Allawi, J. SantaLucia Jr, Biochemistry 36, 10581-10594 (1997)]. By this criterion, all duplexes except for one displayed two-state melting behavior. The remaining one duplex (from the tandem Z:P and S:B set in Table 10) that was not two-state was 5'-CSZTAPBG-3'. It showed no discernable transition at all in the melting curve. This was assigned as a synthesis error, as similar duplexes did melt in a two-state fashion.

Figure 9:
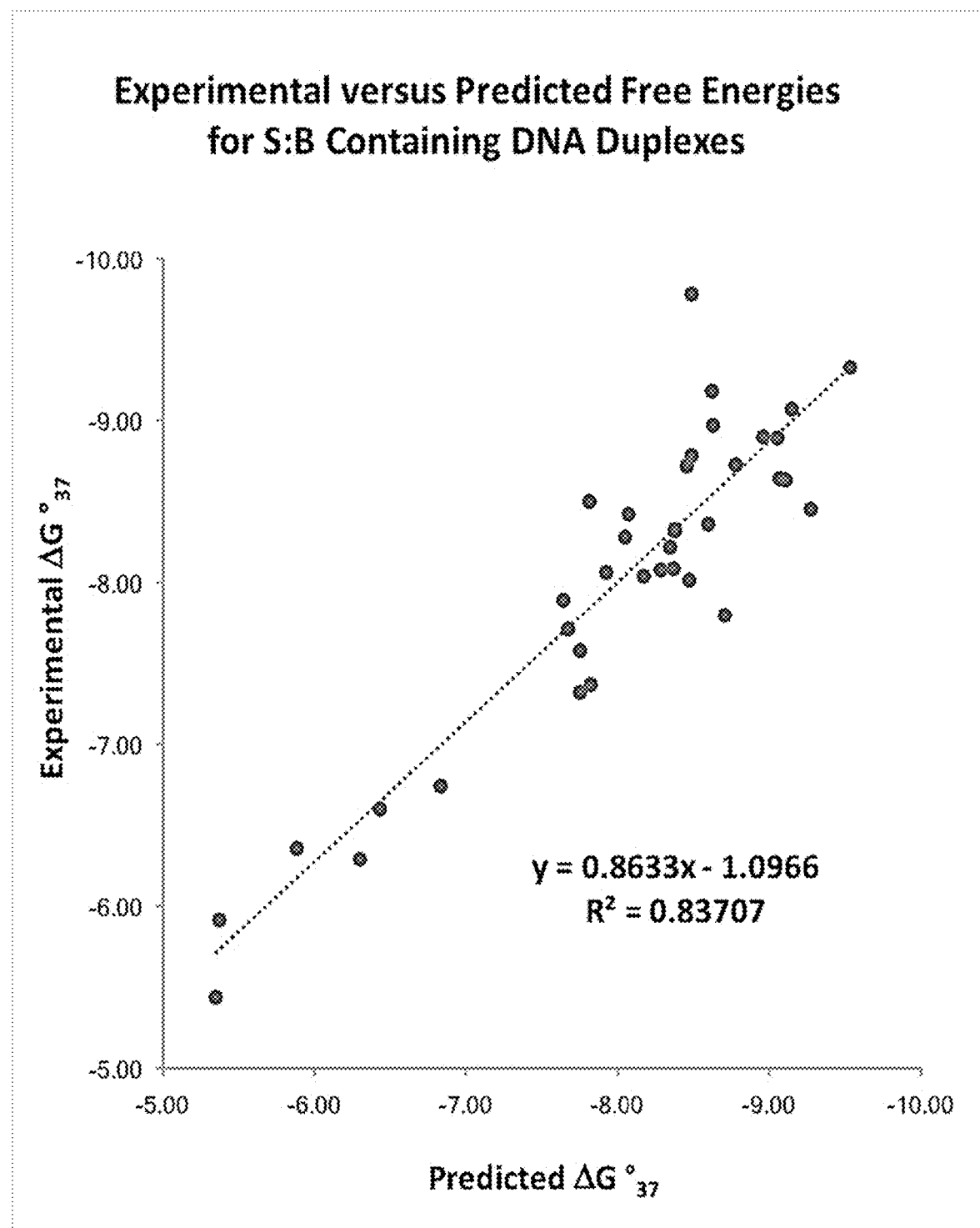
FIG. 9. Plot comparing the experimental free energy changes, $\Delta G°_{37}$, versus the predicted free energy changes for all 37 duplexes in this study (data in Table 6 and 7). NN parameters and standard errors, sigma, for S-B containing NN dimers were derived by SVD and standard error propagation.
Figure 11:
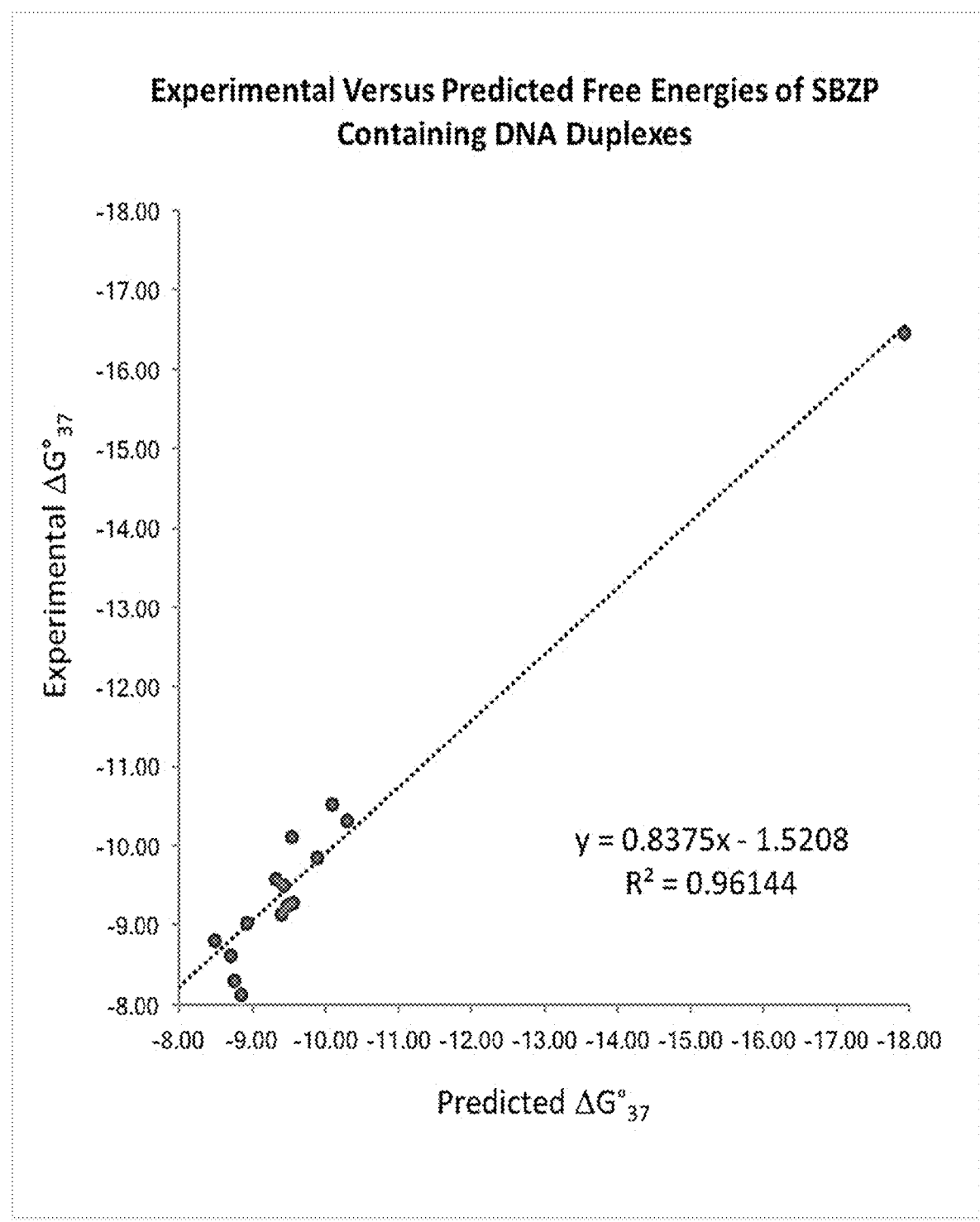
FIG. 11. Experimental vs. predicted free energies of SBZP-containing 8-letter DNA duplexes. Plotted are experimental free energy changes ($\Delta G°_{37}$) versus predicted free energy changes for all 15 duplexes in this study (data in Tables 9 and 10). Parameters for dinucleotide pairing affinity and standard errors, sigma, for dinucleotides containing P and Z dimers were derived by singular value decomposition and standard error propagation.

The error-weighted average of these two methods were then used as the "experimental values" in Table 3, Table 6, and Table 9, and plotted in FIG. 3, FIG. 4, and FIG. 7-12. These were used in singular value decomposition (SVD) to determine base pair dimer nearest-neighbor (BPD "NN") parameters shown in FIG. 7, FIG. 9, and FIG. 11. To perform SVD analysis, for each duplex the total ΔG°$_{37}$ the contributions were subtracted from the nearest-neighbors containing standard Watson-Crick pairs (A:T and G:C), the initiation parameter and the symmetry penalty using the nearest-neighbor parameters from SantaLucia [J. SantaLucia, Jr, Determination of nucleic acid thermodynamics by UV absorbance melting curves, in spectrophotometry and spectrofluorimetry: A practical approach (M. G. Gore, Ed.), Oxford U. Press (2000).]. This resulted in a set of equations in which for each sequence a total ΔG°$_{37}$ increment was equal to a sum of S:B and Z:P containing NN (i.e. unknowns). The SVD calculations were carried out as described in Allawi, H. T. & SantaLucia, J., Jr. [op cit.]. For the Z:P containing NN, a total of 41 equations were used to solve for 11 NN parameters plus a parameter for a terminal Z:P pair (FIG. 7). For the S:B containing NN, a total of 37 equations were used to solve for 11 NN parameters plus a parameter for a terminal S:B pair (FIG. 9). For the tandem Z:P and S:B containing NN, a total of 15 equations were used to solve for 4 NN parameters (FIG. 11). Similar calculations were also performed to determine the NN ΔH° parameters. Nearest-neighbor values for ΔS° may be calculated from the equation: ΔS°=(ΔH°−ΔG°$_{37}$)*1000/310.15. Note that while this study was performed with 1 M NaCl conditions, the NN presented can be used to make predictions at other salt conditions by using the salt extrapolations described in the literature [J. SantaLucia, Jr, Determination of nucleic acid thermodynamics by UV absorbance melting curves, in spectrophotometry and spectrofluorimetry: A practical approach (M. G. Gore, Ed.), Oxford U. Press (2000)].

Quality of the Z:P and S:B Nearest-Neighbor (NN) Parameters

The quality of the NN parameters can be assessed by three different methods: the level of over-determination of the parameters, the standard error values, and the quality of the predictions using the NN parameters. In this study, a total of 93 measurements (the 16mer duplex was omitted from the SVD determination because it is non-two-state) were used to solve for 28 unknowns (i.e. 3.3-fold over-determined). Experience in the SantaLucia lab for many different modified nucleotides has indicated that this level of over-determination is sufficient for accurate determination of NN parameters [J. SantaLucia, Jr, Determination of nucleic acid thermodynamics by UV absorbance melting curves, in spectrophotometry and spectrofluorimetry: A practical approach (M. G. Gore, Ed.), Oxford U. Press (2000)]. The standard error values for the NN parameters are shown in FIG. 7, FIG. 9, FIG. 11, Table 2, Table 5, and Table 8. Most of the NN ΔG°$_{37}$ parameters have errors of about 0.1 kcal/mol. This error level is essentially converged to the limit of what can be expected for the limits of the NN model itself. In principle, the errors could be lowered further by making more measurements, but that would provide only marginal improvement. For example, if the number of measurements in the study was expanded from 94 measurements to 188 (i.e. double the number of measurements), would reduce the standard errors by a factor of SQRT(2) to about 0.07 kcal/mol. In other words, negligible improvement would be obtained by further measurements. Lastly, the NN can be used to predict the duplex thermodynamics (FIG. 3, FIG. 4, Table 3, Table 6, and Table 9). On average, the duplex ΔG°$_{37}$ parameters are predicted within 0.41, 0.31, and 0.36 kcal/mol for duplexes with Z:P, S:B, and tandem Z:P and S:B pairs, respectively. The quality of predictions of the melting temperatures (T$_m$) is another metric of the quality of the NN parameters. On average, the duplex T$_m$'s are predicted within 2.6, 2.0, and 2.1° C. for duplexes with Z:P, S:B, and tandem Z:P and S:B pairs, respectively. We note that such quality of prediction is exceptional for such short 8-mer duplexes, which are highly demanding of the NN model. These error values are consistent with those observed for standard DNA/DNA duplex thermodynamic determinations in the literature from the SantaLucia Lab and for RNA duplexes from the Turner Lab. For typical oligonucleotides that would be used for PCR and other applications that are in the length range of 18-24 BP the T$_m$ prediction errors will likely be significantly smaller than 2.0° C. Compare this performance to the average error of 1.6° C. for a dataset of ~320 duplexes using the published DNA NN parameters for the usual 4-letter alphabet [J. SantaLucia, Proc. Natl Acad. Sci. USA 95, 1460-1465 (1998)]. Lastly, the plots of Experimental vs. Predicted ΔG°$_{37}$ (FIG. 3, FIG. 4, FIG. 7, FIG. 9, and FIG. 11) and T$_m$ shown in Table 3, Table 6, and Table 9 show the quality of the predictions with slopes near 1, intercepts near 0, and R$^2$>0.8 for all plots. Again, such high-quality plots for 8-mer sequences is impressive. For longer sequences (e.g. 18-24 BP) with larger ranges in $\Delta G°_{37}$ and $T_m$, the regression parameters for experiments vs. predictions would likely be even better.

Trends in NN Parameters

Table 2 compares the NN trends for NN containing a Z:P pair compared to the similar NN with C:G pair. For example, the NN AP/TZ (−1.66 kcal/mol) is compared to AC/TG (−1.28 kcal/mol), with a $\Delta\Delta G°_{37}$ of −0.38 kcal/mol. On average, an Z:P substitution is −0.17 kcal/mol more stable than the similar NN that has a C:G pair. This suggests that each C:G to Z:P substitution would make the duplex −0.34 kcal/mol more stable. However, the average masks the significant sequence dependence observed. Depending on the sequence context, a single C:G to Z:P substation would have $\Delta\Delta G°_{37}$ vary from +0.84 to −0.86 kcal/mol. This large range is likely due to the different dipole moment sizes and directions for Z:P compared to C:G, thus impacting the trends in dipole-dipole contributions to base pair stacking. Tandem Z:P NN also show a large sequence dependence that is different than that for tandem C-G NN (e.g. ZP/PZ vs. PZ/ZP differ by −1.27 kcal/mol, while CG/GC vs. GC/CG differ by +0.07 kcal/mol). This is further evidence for stacking differences of Z:P compared to C:G.

Table 5 compares the NN trends for NN containing a S:B pair compared to the similar NN with T:A pair. For example, the NN AB/TS (−1.24 kcal/mol) is compared to AA/TT (−1.00 kcal/mol), with a $\Delta\Delta G°_{37}$ of −0.24 kcal/mol. On average, an S:B substitution is −0.53 kcal/mol more stable than the similar NN that has a T:A pair. This suggests that each T:A to S:B substitution would make the duplex −1.06 kcal/mol more stable. However, the average masks the significant sequence dependence observed. Depending on the sequence context, a single T:A to S:B substitution has $\Delta\Delta G°_{37}$ vary from −0.32 to −1.58 kcal/mol. This large range is likely due to the different dipole moment sizes and directions for S:B compared to T:A, thus impacting the trends in dipole-dipole contributions to base pair stacking. Tandem S:B NN also show a small sequence dependence that is slightly different than that for tandem T:A NN (e.g. SB/BS vs. BS/SB differ by −0.01 kcal/mol, while TA/AT vs. AT/TA differ by +0.30 kcal/mol). This is further evidence for stacking differences of S:B compared to T:A.

Table 8 compares the NN trends for NN containing tandem S:B and Z:P pairs compared to the similar NN with C:G pairs. For example, the NN SZ/BP (−2.29 kcal/mol) is compared to CC/GG (−1.84 kcal/mol), with a $\Delta\Delta G°_{37}$ of −0.45 kcal/mol. On average, the tandem S:B, Z:P NN are −0.08 kcal/mol more stable than their C:G counterparts. Interestingly, the tandem S:B, Z:P NN show only a weak sequence dependence, with $\Delta G°_{37}$ values ranging from −1.85 to −2.29 kcal/mol.

TABLE 2

Comparison of Z-P to C-G NN Parameters

| | $\Delta G_{37}$ with Z-P | Error $\Delta G$ | $\Delta G_{37}$ with C-G | $\Delta\Delta G_{37}$ |
|---|---|---|---|---|
| Single Internal Z-P pairs: | | | | |
| AP/TZ | −1.66 | 0.10 | −1.28 | −0.38 |
| AZ/TP | −1.62 | 0.10 | −1.44 | −0.18 |
| CP/GZ | −2.32 | 0.10 | −2.17 | −0.15 |
| CZ/GP | −2.26 | 0.09 | −1.84 | −0.42 |
| GP/CZ | −2.10 | 0.11 | −1.84 | −0.26 |

TABLE 2-continued

Comparison of Z-P to C-G NN Parameters

| | $\Delta G_{37}$ with Z-P | Error $\Delta G$ | $\Delta G_{37}$ with C-G | $\Delta\Delta G_{37}$ |
|---|---|---|---|---|
| GZ/CP | −1.78 | 0.11 | −2.24 | +0.42 |
| TP/AZ | −1.40 | 0.08 | −1.45 | +0.05 |
| TZ/AP | −1.73 | 0.09 | −1.30 | −0.43 |
| Tandem Z-P pairs: | | | | |
| PP/ZZ | −2.28 | 0.23 | −1.84 | −0.44 |
| ZP/PZ | −2.88 | 0.22 | −2.17 | −0.71 |
| PZ/ZP | −1.61 | 0.08 | −2.24 | +0.63 |
| Average of Single Z-P substitutions | | | | −0.17 |

*All results are in kcal/mol
Parameters with C-G pairs are from (23).

TABLE 3

Experimental and predicted free energy changes and $T_m$'s for the 41 Z:P containing duplexes. The experimental values are the error-weighted average of thermodynamic values from curve fit and $T_m^{-1}$ methods of analysis (see Table 4). These are the data plotted in FIG. 3, FIG. 4, and FIG. 7.

| | Pred. $\Delta G°_{37}$ (kcal/mol) | Expt. $\Delta G°_{37}$ (kcal/mol) | Pred. Tm ($1e^{-4}$M) | Exp. Tm ($1e^{-4}$M) |
|---|---|---|---|---|
| Self-Complementary Duplex | | | | |
| GGZATPCC | −8.50 | −7.93 | 61.0 | 56.8 |
| GCPATZGC | −11.08 | −11.46 | 65.4 | 66.4 |
| GGZTAPCC | −8.72 | −8.38 | 62.9 | 62.0 |
| GCPTAZGC | −10.54 | −10.57 | 65.2 | 64.9 |
| GAZCGPTC | −9.81 | −9.92 | 63.5 | 64.3 |
| GTZCGPAC | −10.32 | −10.65 | 63.5 | 64.7 |
| GAZATPTC | −7.12 | −7.13 | 46.6 | 47.0 |
| GAPATZTC | −7.87 | −7.96 | 50.1 | 49.3 |
| GAZTAPTC | −7.34 | −7.23 | 48.1 | 47.9 |
| GTZATPAC | −7.63 | −7.78 | 48.6 | 49.6 |
| GPCATGZC | −9.12 | −8.59 | 65.0 | 61.8 |
| GZGATCPC | −10.20 | −10.39 | 70.0 | 66.2 |
| CZCATGPG | −10.09 | −9.87 | 64.9 | 64.6 |
| CZTCGAPG | −10.20 | −10.40 | 64.7 | 63.3 |
| CZACGTPG | −9.97 | −10.23 | 63.0 | 63.4 |
| CPGATCZG | −10.24 | −10.52 | 63.0 | 64.3 |
| PGCATGCZ | −9.38 | −8.61 | 61.8 | 58.5 |
| ZGCATGCP | −9.51 | −8.02 | 63.8 | 61.9 |
| PACTAGTZ | −6.10 | −6.40 | 39.7 | 41.2 |
| ZACTAGTP | −5.42 | −6.33 | 35.0 | 41.0 |
| GACPZGTC | −9.34 | −10.38 | 58.0 | 64.6 |
| GACZPGTC | −10.48 | −10.79 | 63.6 | 66.2 |
| GTGPZCAC | −9.19 | −10.28 | 59.4 | 63.2 |
| GTGZPCAC | −9.80 | −10.81 | 65.2 | 67.2 |
| GCAPZTGC | −9.91 | −10.48 | 63.4 | 64.4 |
| GCTPZAGC | −9.06 | −8.83 | 58.1 | 59.1 |
| GCAZPTGC | −11.10 | −10.99 | 67.6 | 65.3 |
| GCTZPAGC | −11.00 | −9.73 | 64.6 | 61.6 |
| GZZATPPC | −9.38 | −9.86 | 64.0 | 69.8 |
| GZZTAPPC | −9.60 | −9.90 | 65.6 | 68.5 |
| CPPATZZG | −11.16 | −12.07 | 64.3 | 67.6 |
| PGACGTCZ | −8.77 | −9.05 | 57.4 | 58.3 |
| GGAZPTCC | −10.00 | −9.66 | 62.9 | 61.3 |
| GPACGTZC | −10.32 | −9.51 | 63.4 | 60.5 |
| GGAPZTCC | −8.81 | −8.63 | 57.9 | 57.4 |
| GAZZPPTC | −10.88 | −11.87 | 64.9 | 68.7 |
| GTPPZZAC | −9.46 | −8.13 | 59.1 | 50.9 |
| non-self-complementary | | | | |
| GCCAPTTAA CGGTZAATT | −9.37 | −9.01 | 52.6 | 50.1 |
| GCZAGTTAA CGPTCAATT | −9.18 | −9.19 | 51.2 | 50.2 |
| GZCAGTTAA CPGTCAATT | −8.60 | −9.35 | 49.4 | 49.8 |

TABLE 3-continued

Experimental and predicted free energy changes and $T_m$'s for the 41 Z:P containing duplexes. The experimental values are the error-weighted average of thermodynamic values from curve fit and $T_m^{-1}$ methods of analysis (see Table 4). These are the data plotted in FIG. 3, FIG. 4, and FIG. 7.

| | Pred. $\Delta G°_{37}$ (kcal/mol) | Expt. $\Delta G°_{37}$ (kcal/mol) | Pred. Tm ($1e^{-4}$M) | Exp. Tm ($1e^{-4}$M) |
|---|---|---|---|---|
| GZZAGTTAA CPPTCAATT | −8.74 | −8.45 | 49.6 | 47.8 |

TABLE 4

Data from melts of duplexes containing Z:P nearest-neighbors in 1M NaCl, 10 mM $Na_2HPO_4$, and 0.5 mM $Na_2EDTA$, pH 7.00 buffer. All data were fit using the thermodynamic analysis software Meltwin v.3.5.

| | $T_m^{-1}$ Method | | | | Curve Fit Method | | |
|---|---|---|---|---|---|---|---|
| Duplex | $\Delta H°$ (kcal/mol) | $\Delta S°$ (cal/mol * K) | $\Delta G°_{37}$ (kcal/mol) | $T_m$ ($1e^{-4}$M) | $\Delta H°$ (kcal/mol) | $\Delta S°$ (cal/mol * K) | $\Delta G°_{37}$ (kcal/mol) |
| GGZATPCC | −34.1 ± 8.6 | −84.7 ± 26.8 | −7.79 ± 0.67 | 56.8 | −38.8 ± 5.0 | −99.4 ± 15.5 | −7.94 ± 0.20 |
| GCPATZGC | −67.7 ± 5.8 | −181.2 ± 17.6 | −11.52 ± 0.40 | 66.4 | −66.5 ± 3.3 | −177.5 ± 10.0 | −11.44 ± 0.22 |
| GGZTAPCC | −36.5 ± 12.1 | −90.7 ± 36.8 | −8.38 ± 1.38 | 62.0 | −36.2 ± 4.7 | −89.6 ± 14.0 | −8.38 ± 0.33 |
| GCPTAZGC | −58.6 ± 1.7 | −154.9 ± 5.0 | −10.53 ± 0.11 | 64.9 | −65.1 ± 5.4 | −174.5 ± 16.3 | −10.96 ± 0.36 |
| GAZCGPTC | −50.2 ± 5.0 | −130.4 ± 15.2 | −9.81 ± 0.28 | 64.3 | −54.6 ± 4.8 | −143.7 ± 14.5 | −10.04 ± 0.30 |
| GTZCGPAC | −60.3 ± 1.0 | −160.2 ± 3.2 | −10.64 ± 0.16 | 64.7 | −64.2 ± 3.5 | −172.0 ± 10.6 | −10.87 ± 0.24 |
| GAZATPTC | −44.3 ± 12.4 | −120.0 ± 39.3 | −7.11 ± 0.88 | 47.0 | −47.0 ± 4.6 | −128.4 ± 14.2 | −7.13 ± 0.18 |
| GAPATZTC | −59.4 ± 4.0 | −165.9 ± 12.7 | −7.96 ± 0.08 | 49.3 | −60.3 ± 6.3 | −168.8 ± 19.8 | −7.95 ± 0.15 |
| GAZTAPTC | −45.0 ± 5.3 | −121.8 ± 17.0 | −7.24 ± 0.17 | 47.9 | −47.0 ± 7.0 | −128.1 ± 22.6 | −7.23 ± 0.06 |
| GTZATPAC | −49.8 ± 3.9 | −135.5 ± 12.5 | −7.75 ± 0.17 | 49.6 | −55.6 ± 2.6 | −154.0 ± 8.3 | −7.81 ± 0.10 |
| GPCATGZC | −38.4 ± 6.7 | −96.3 ± 20.8 | −8.50 ± 0.47 | 61.8 | −40.9 ± 9.1 | −103.9 ± 27.9 | −8.68 ± 0.47 |
| GZGATCPC | −52.9 ± 5.7 | −137.5 ± 17.3 | −10.27 ± 0.34 | 66.2 | −59.9 ± 9.4 | −158.6 ± 28.5 | −10.71 ± 0.55 |
| CZCATGPG | −49.8 ± 6.8 | −129.1 ± 20.7 | −9.77 ± 0.46 | 64.6 | −52.3 ± 5.5 | −136.5 ± 16.5 | −9.93 ± 0.36 |
| CZTCGAPG | −57.6 ± 4.5 | −152.7 ± 13.8 | −10.25 ± 0.27 | 63.3 | −64.5 ± 5.3 | −173.5 ± 16.0 | −10.65 ± 0.34 |
| CZACGTPG | −55.1 ± 7.7 | −145.0 ± 23.4 | −10.08 ± 0.49 | 63.4 | −60.4 ± 7.1 | −161.2 ± 21.1 | −10.40 ± 0.51 |
| CPGATCZG | −58.6 ± 1.9 | −155.1 ± 5.7 | −10.45 ± 0.11 | 64.3 | −67.1 ± 4.4 | −181.1 ± 13.3 | −10.97 ± 0.29 |
| PGCATGCZ | −40.2 ± 1.8 | −101.9 ± 5.7 | −8.60 ± 0.06 | 58.5 | −45.3 ± 5.8 | −117.6 ± 17.8 | −8.81 ± 0.24 |
| ZGCATGCP | −30.0 ± 7.1 | −71.4 ± 22.0 | −7.87 ± 0.59 | 61.9 | −34.4 ± 9.9 | −84.8 ± 31.2 | −8.06 ± 0.31 |
| PACTAGTZ | −50.8 ± 9.9 | −143.0 ± 32.0 | −6.42 ± 0.26 | 41.2 | −53.6 ± 0.6 | −152.0 ± 2.1 | −6.40 ± 0.05 |
| ZACTAGTP | −52.7 ± 8.1 | −149.4 ± 26.5 | −6.32 ± 0.25 | 41.0 | −50.7 ± 3.5 | −142.9 ± 11.6 | −6.33 ± 0.10 |
| GACPZGTC | −56.7 ± 5.9 | −149.6 ± 17.9 | −10.32 ± 0.38 | 64.6 | −58.7 ± 6.4 | −155.4 ± 19.2 | −10.46 ± 0.41 |
| GACZPGTC | −53.0 ± 9.9 | −137.5 ± 29.6 | −10.36 ± 0.82 | 66.2 | −60.9 ± 4.6 | −161.3 ± 13.8 | −10.86 ± 0.33 |
| GTGPZCAC | −60.2 ± 3.0 | −160.7 ± 9.1 | −10.33 ± 0.17 | 63.2 | −58.1 ± 2.9 | −154.5 ± 8.7 | −10.22 ± 0.18 |
| GTGZPCAC | −56.1 ± 4.9 | −146.3 ± 14.9 | −10.69 ± 0.34 | 67.2 | −58.9 ± 4.0 | −154.9 ± 11.9 | −10.90 ± 0.30 |
| GCAPZTGC | −55.8 ± 6.4 | −146.6 ± 20.0 | −10.31 ± 0.40 | 64.4 | −64.5 ± 8.2 | −173.0 ± 24.4 | −10.86 ± 0.59 |
| GCTPZAGC | −42.9 ± 6.7 | −110.3 ± 20.9 | −8.68 ± 0.34 | 59.1 | −49.1 ± 4.1 | −129.7 ± 12.5 | −8.89 ± 0.21 |
| GCAZPTGC | −60.9 ± 4.7 | −161.5 ± 14.3 | −10.83 ± 0.30 | 65.3 | −68.2 ± 6.4 | −183.5 ± 19.4 | −11.31 ± 0.42 |
| GCTZPAGC | −52.7 ± 4.6 | −139.0 ± 14.2 | −9.62 ± 0.24 | 61.6 | −58.6 ± 5.5 | −157.0 ± 16.8 | −9.92 ± 0.32 |
| GZZATPPC | −44.5 ± 6.6 | −111.7 ± 19.8 | −9.90 ± 0.51 | 69.8 | −42.3 ± 8.7 | −104.6 ± 26.3 | −9.82 ± 0.56 |
| GZZTAPPC | −43.5 ± 7.4 | −108.9 ± 22.4 | −9.72 ± 0.57 | 68.5 | −49.8 ± 9.9 | −127.8 ± 29.6 | −10.17 ± 0.69 |
| CPPATZZG | −70.9 ± 4.5 | −189.6 ± 13.7 | −12.04 ± 0.31 | 67.6 | −71.5 ± 5.3 | −191.5 ± 15.9 | −12.11 ± 0.38 |
| PGACGTCZ | −51.0 ± 4.1 | −135.4 ± 12.6 | −8.99 ± 0.18 | 58.3 | −58.4 ± 7.9 | −158.3 ± 24.2 | −9.33 ± 0.38 |
| GGAZPTCC | −54.7 ± 6.1 | −145.4 ± 18.6 | −9.64 ± 0.34 | 61.3 | −55.2 ± 6.9 | −146.8 ± 21.0 | −9.69 ± 0.36 |
| GPACGTZC | −53.3 ± 1.9 | −141.4 ± 5.8 | −9.48 ± 0.08 | 60.5 | −61.3 ± 4.8 | −165.7 ± 14.5 | −9.85 ± 0.29 |
| GGAPZTCC | −42.4 ± 12.9 | −109.3 ± 40.4 | −8.49 ± 0.78 | 57.4 | −48.2 ± 3.5 | −127.5 ± 11.2 | −8.63 ± 0.07 |
| GCCAPTTAA | −54.3 ± 6.2 | −146.3 ± 19.5 | −8.91 ± 0.18 | 50.1 | −62.7 ± 3.0 | −173.1 ± 9.5 | −9.03 ± 0.09 |
| GCZAGTTAA | −60.3 ± 9.4 | −165.0 ± 29.9 | −9.10 ± 0.32 | 50.2 | −69.9 ± 9.0 | −195.6 ± 28.6 | −9.21 ± 0.17 |
| GZCAGTTAA | −70.9 ± 3.3 | −198.5 ± 10.5 | −9.34 ± 0.06 | 49.8 | −72.2 ± 2.1 | −202.5 ± 6.8 | −9.36 ± 0.05 |
| GZZAGTTAA | −55.5 ± 1.8 | −151.9 ± 5.7 | −8.40 ± 0.04 | 47.8 | −61.8 ± 3.0 | −171.8 ± 9.5 | −8.52 ± 0.05 |
| GAZZPPTC | −64.4 ± 6.0 | −169.9 ± 18.0 | −11.72 ± 0.48 | 68.7 | −67.5 ± 3.6 | −179.0 ± 10.7 | −11.94 ± 0.33 |
| GTPPZZAC | −53.9 ± 6.4 | −147.8 ± 20.2 | −8.06 ± 0.24 | 50.9 | −58.8 ± 4.7 | −163.2 ± 14.8 | −8.16 ± 0.17 |

TABLE 5

Comparison of S:B to T:A NN Parameters

| | $\Delta G_{37}$ with S-B | Error $\Delta G$ | $\Delta G_{37}$ with T-A | $\Delta\Delta G_{37}$ |
|---|---|---|---|---|
| Single Internal S-B pairs: | | | | |
| AB/TS | −1.24 | 0.09 | −1.00 | −0.24 |
| AS/TB | −1.30 | 0.09 | −0.88 | −0.42 |
| CB/GS | −1.92 | 0.09 | −1.45 | −0.47 |
| CS/GB | −1.44 | 0.09 | −1.28 | −0.16 |
| GB/CS | −1.70 | 0.10 | −1.30 | −0.40 |
| GS/CB | −1.78 | 0.10 | −1.44 | −0.34 |
| TB/AS | −1.37 | 0.08 | −0.58 | −0.79 |
| TS/AB | −1.36 | 0.08 | −1.00 | −0.36 |
| Tandem S-B pairs: | | | | |
| BB/SS | −1.79 | 0.08 | −1.00 | −0.79 |
| SB/BS | −1.68 | 0.20 | −0.58 | −1.10 |

TABLE 5-continued

Comparison of S:B to T:A NN Parameters

|  | $\Delta G_{37}$ with S-B | Error $\Delta G$ | $\Delta G_{37}$ with T-A | $\Delta\Delta G_{37}$ |
|---|---|---|---|---|
| BS/SB | −1.67 | 0.20 | −0.88 | −0.79 |
| Average of Single S:B substitutions |  |  |  | −0.53 |

*All results are in kcal/mol
Parameters with T:A pairs are from (23).

TABLE 6

The Experimental and Predicted Free Energy changes and $T_m$'s for the 37 S:B containing duplexes. Experimental values are the error-weighted average of thermodynamic values from curve fit and $T_m^{-1}$ methods of analysis (see Table 7). These are the data plotted in FIG. 9 and FIG. 10.

|  | Pred. $\Delta G°_{37}$ (kcal/mol) | Expt. $\Delta G°_{37}$ (kcal/mol) | Pred. $T_m$ (1e$^{-4}$M) | Exp. $T_m$ (1e$^{-4}$M) |
|---|---|---|---|---|
| Self-Complementary Duplex |  |  |  |  |
| GGSATBCC | −8.47 | −8.02 | 55.2 | 51.9 |
| GCBATSGC | −9.53 | −9.33 | 59.6 | 60.5 |
| GGSTABCC | −7.92 | −8.06 | 51.5 | 52.0 |
| GCBTASGC | −9.11 | −8.63 | 59.0 | 56.5 |
| GASCGBTC | −8.38 | −8.32 | 54.2 | 55.8 |
| GTSCGBAC | −8.78 | −8.73 | 54.9 | 53.5 |
| GASATBTC | −6.43 | −6.60 | 41.8 | 42.7 |
| GABATSTC | −6.30 | −6.29 | 40.6 | 40.7 |
| GASTABTC | −5.88 | −6.36 | 38.3 | 40.8 |
| GTSATBAC | −6.83 | −6.74 | 43.7 | 43.5 |
| GBCATGSC | −8.35 | −8.22 | 54.4 | 53.1 |
| GSGATCBC | −8.49 | −9.78 | 55.3 | 61.1 |
| CSCATGBG | −7.67 | −7.71 | 49.3 | 48.5 |
| CSTCGABG | −7.75 | −7.32 | 48.9 | 45.4 |
| CSACGTBG | −8.28 | −8.08 | 52.0 | 50.2 |
| CBGATCSG | −7.81 | −8.50 | 50.2 | 54.8 |
| BGCATGCS | −7.75 | −7.58 | 51.6 | 52.0 |
| SGCATGCB | −8.71 | −7.80 | 58.6 | 53.3 |
| BACTAGTS | −5.35 | −5.44 | 34.7 | 35.1 |
| SACTAGTB | −5.37 | −5.92 | 34.8 | 38.5 |
| GACBSGTC | −8.60 | −8.36 | 55.0 | 53.3 |
| GACSBGTC | −7.64 | −7.89 | 49.3 | 51.8 |
| GTGBSCAC | −8.46 | −8.72 | 54.1 | 56.4 |
| GTGSBCAC | −8.62 | −9.18 | 56.3 | 60.7 |
| GCABSTGC | −9.15 | −9.07 | 57.1 | 54.7 |
| GCTBSAGC | −9.07 | −8.64 | 57.1 | 55.2 |
| GCASBTGC | −9.27 | −8.45 | 60.4 | 55.9 |
| GCTSBAGC | −9.05 | −8.89 | 57.3 | 57.4 |
| GSSATBBC | −8.37 | −8.09 | 57.0 | 53.7 |
| GSSTABBC | −7.82 | −7.37 | 52.8 | 50.4 |
| CBBATSSG | −8.63 | −8.97 | 57.7 | 57.0 |
| GASSBBTC | −8.07 | −8.42 | 56.2 | 58.6 |
| GTBBSSAC | −8.49 | −8.78 | 56.6 | 59.9 |
| GGASBTCC | −8.17 | −8.04 | 54.3 | 50.2 |
| GSACGTBC | −8.96 | −8.90 | 56.8 | 57.7 |
| GGABSTCC | −8.05 | −8.28 | 51.6 | 51.6 |
| GBTCGASC | −8.38 | −8.33 | 54.2 | 54.1 |

TABLE 7

The raw data obtained for duplex melts containing S:B nearest-neighbors in 1M NaCl, 10 mM Na$_2$HPO$_4$, and 0.5 mM Na$_2$EDTA, pH 7.00 buffer. All data were fit using the thermodynamic analysis software Meltwin v.3.5.

| | $T_m^{-1}$ Method | | | | Curve Fit Method | | |
|---|---|---|---|---|---|---|---|
| Duplex | $\Delta H°$ (kcal/mol) | $\Delta S°$ (cal/mol * K) | $\Delta G°_{37}$ (kcal/mol) | $T_m$ (1e$^{-4}$M) | $\Delta H°$ (kcal/mol) | $\Delta S°$ (cal/mol * K) | $\Delta G°_{37}$ (kcal/mol) |
| GGSATBCC | −50.6 ± 1.1 | −137.4 ± 3.3 | −8.02 ± 0.02 | 51.9 | −55.9 ± 7.0 | −154.1 ± 22.3 | −8.06 ± 0.13 |
| GCBATSGC | −50.0 ± 7.2 | −131.5 ± 22.1 | −9.25 ± 0.43 | 60.5 | −52.4 ± 3.0 | −138.7 ± 8.9 | −9.35 ± 0.21 |
| GGSTABCC | −51.1 ± 7.8 | −138.8 ± 24.7 | −8.05 ± 0.34 | 52.0 | −52.9 ± 8.1 | −144.4 ± 25.6 | −8.06 ± 0.19 |
| GCBTASGC | −45.4 ± 5.9 | −118.9 ± 18.3 | −8.51 ± 0.31 | 56.5 | −50.7 ± 3.6 | −135.5 ± 10.9 | −8.69 ± 0.23 |
| GASCGBTC | −44.7 ± 5.8 | −117.3 ± 18.3 | −8.27 ± 0.23 | 55.8 | −48.2 ± 4.0 | −128.4 ± 12.7 | −8.33 ± 0.12 |
| GTSCGBAC | −59.2 ± 8.2 | −162.9 ± 25.8 | −8.71 ± 0.32 | 53.5 | −60.4 ± 6.8 | −166.6 ± 21.3 | −8.74 ± 0.21 |
| GASATBTC | −45.7 ± 3.6 | −125.9 ± 11.5 | −6.62 ± 0.08 | 42.7 | −50.6 ± 1.0 | −141.9 ± 3.1 | −6.58 ± 0.07 |
| GABATSTC | −44.5 ± 3.8 | −122.9 ± 12.6 | −6.36 ± 0.11 | 40.7 | −48.2 ± 1.9 | −135.2 ± 6.0 | −6.29 ± 0.03 |
| GASTABTC | −47.6 ± 4.6 | −132.9 ± 15.2 | −6.42 ± 0.15 | 40.8 | −52.3 ± 3.9 | −148.1 ± 12.4 | −6.35 ± 0.05 |
| GTSATBAC | −50.7 ± 3.7 | −141.7 ± 11.9 | −6.75 ± 0.05 | 43.5 | −56.8 ± 3.7 | −161.4 ± 12.0 | −6.73 ± 0.05 |
| GBCATGSC | −52.1 ± 1.9 | −141.4 ± 6.1 | −8.22 ± 0.04 | 53.1 | −52.7 ± 3.4 | −143.2 ± 10.7 | −8.24 ± 0.07 |
| GSGATCBC | −53.8 ± 6.0 | −142.4 ± 18.4 | −9.65 ± 0.35 | 61.1 | −58.1 ± 5.0 | −155.6 ± 15.2 | −9.89 ± 0.32 |
| CSCATGBG | −60.7 ± 9.5 | −170.6 ± 30.4 | −7.75 ± 0.27 | 48.5 | −56.9 ± 2.8 | −158.6 ± 9.0 | −7.70 ± 0.09 |
| CSTCGABG | −60.8 ± 9.9 | −172.4 ± 31.8 | −7.34 ± 0.33 | 45.4 | −62.2 ± 3.2 | −177.0 ± 10.3 | −7.32 ± 0.14 |
| CSACGTBG | −58.6 ± 6.8 | −163.0 ± 21.5 | −8.07 ± 0.19 | 50.2 | −57.0 ± 8.6 | −157.8 ± 27.4 | −8.09 ± 0.13 |
| CBGATCSG | −49.8 ± 6.0 | −133.3 ± 18.7 | −8.46 ± 0.24 | 54.8 | −52.2 ± 2.5 | −141.0 ± 8.0 | −8.51 ± 0.09 |
| BGCATGCS | −40.2 ± 3.2 | −105.2 ± 10.2 | −7.57 ± 0.10 | 52.0 | −43.4 ± 3.4 | −115.3 ± 10.8 | −7.60 ± 0.11 |
| SGCATGCB | −39.8 ± 4.0 | −103.3 ± 12.6 | −7.76 ± 0.13 | 53.3 | −43.2 ± 1.9 | −114.1 ± 6.0 | −7.82 ± 0.15 |
| BACTAGTS | −46.2 ± 4.1 | −131.3 ± 13.7 | −5.52 ± 0.16 | 35.1 | −49.6 ± 1.5 | −142.5 ± 4.7 | −5.42 ± 0.07 |
| SACTAGTB | −47.4 ± 9.3 | −133.7 ± 30.5 | −5.91 ± 0.40 | 38.5 | −47.9 ± 4.6 | −135.4 ± 15.1 | −5.92 ± 0.10 |
| GACBSGTC | −47.7 ± 11.6 | −117.0 ± 36.6 | −8.33 ± 0.58 | 53.3 | −55.8 ± 1.1 | −121.4 ± 3.5 | −8.36 ± 0.06 |
| GACSBGTC | −49.2 ± 4.0 | −133.1 ± 12.8 | −7.89 ± 0.12 | 51.8 | −49.2 ± 1.6 | −133.1 ± 4.8 | −7.89 ± 0.09 |
| GTGBSCAC | −47.4 ± 8.3 | −125.3 ± 25.8 | −8.57 ± 0.30 | 56.4 | −52.3 ± 3.4 | −140.6 ± 10.9 | −8.73 ± 0.13 |
| GTGSBCAC | −47.6 ± 2.1 | −124.0 ± 6.6 | −9.14 ± 0.10 | 60.7 | −52.7 ± 3.7 | −139.7 ± 11.3 | −9.38 ± 0.21 |
| GCABSTGC | −59.1 ± 9.8 | −161.6 ± 30.6 | −9.00 ± 0.42 | 54.7 | −62.1 ± 5.2 | −171.2 ± 16.2 | −9.09 ± 0.21 |
| GCTBSAGC | −46.5 ± 14.3 | −122.5 ± 44.6 | −8.48 ± 0.80 | 55.2 | −53.2 ± 4.1 | −143.8 ± 12.9 | −8.64 ± 0.10 |
| GCASBTGC | −46.2 ± 3.7 | −122.1 ± 11.4 | −8.37 ± 0.14 | 55.9 | −49.3 ± 2.1 | −131.7 ± 6.7 | −8.48 ± 0.09 |
| GCTSBAGC | −52.0 ± 4.8 | −139.1 ± 15.0 | −8.89 ± 0.22 | 57.4 | −52.0 ± 3.7 | −139.0 ± 11.2 | −8.90 ± 0.24 |
| GSSATBBC | −41.7 ± 9.3 | −108.8 ± 29.1 | −7.94 ± 0.55 | 53.7 | −48.6 ± 4.9 | −130.4 ± 15.1 | −8.12 ± 0.25 |

TABLE 7-continued

The raw data obtained for duplex melts containing S:B nearest-neighbors in 1M NaCl, 10 mM $Na_2HPO_4$, and 0.5 mM $Na_2EDTA$, pH 7.00 buffer. All data were fit using the thermodynamic analysis software Meltwin v.3.5.

| | $T_m^{-1}$ Method | | | | Curve Fit Method | | |
|---|---|---|---|---|---|---|---|
| Duplex | ΔH° (kcal/mol) | ΔS° (cal/mol * K) | ΔG°$_{37}$ (kcal/mol) | $T_m$ ($1e^{-4}$M) | ΔH° (kcal/mol) | ΔS° (cal/mol * K) | ΔG°$_{37}$ (kcal/mol) |
| GSSTABBC | −38.7 ± 13.0 | −101.0 ± 41.2 | −7.35 ± 1.08 | 50.4 | −40.4 ± 5.1 | −106.6 ± 15.9 | −7.37 ± 0.13 |
| CBBATSSG | −52.5 ± 4.5 | −140.7 ± 13.9 | −8.90 ± 0.20 | 57.0 | −56.1 ± 5.5 | −151.6 ± 17.0 | −9.07 ± 0.24 |
| GASSBBTC | −37.5 ± 9.1 | −94.3 ± 28.3 | −8.27 ± 0.52 | 58.6 | −42.4 ± 1.8 | −109.5 ± 5.5 | −8.43 ± 0.14 |
| GTBBSSAC | −42.3 ± 2.4 | −108.2 ± 7.5 | −8.73 ± 0.11 | 59.9 | −48.3 ± 3.7 | −126.8 ± 11.1 | −9.01 ± 0.23 |
| GGASBTCC | −55.6 ± 4.9 | −153.6 ± 15.6 | −8.01 ± 0.15 | 50.2 | −59.0 ± 4.5 | −164.1 ± 14.1 | −8.07 ± 0.14 |
| GSACGTBC | −46.8 ± 11.3 | −122.8 ± 34.9 | −8.75 ± 0.72 | 57.7 | −51.7 ± 2.3 | −138.0 ± 7.1 | −8.91 ± 0.13 |
| GGABSTCC | −55.3 ± 4.5 | −151.9 ± 14.2 | −8.22 ± 0.12 | 51.6 | −62.1 ± 4.8 | −173.3 ± 15.3 | −8.34 ± 0.13 |
| GBTCGASC | −45.1 ± 6.7 | −119.1 ± 21.0 | −8.19 ± 0.34 | 54.1 | −51.2 ± 2.2 | −138.2 ± 6.9 | −8.35 ± 0.13 |

TABLE 8

Comparison of tandem S:B, Z:P NN to C:G NN Parameters

| | ΔG$_{37}$ with S:B Z:P | Error ΔG | ΔG$_{37}$ with C:G | ΔΔG37 |
|---|---|---|---|---|
| Tandem S:B-Z:P pairs: | | | | |
| SZ/BP | −2.29 | 0.11 | −1.84 | −0.45 |
| ZS/PB | −1.86 | 0.09 | −1.84 | −0.02 |
| SP/BZ | −2.28 | 0.08 | −2.17 | −0.11 |
| PS/ZB | −1.90 | 0.12 | −2.17 | +0.27 |
| Average of S:B, Z:P to C:G substitutions | | | | −0.08 |

*All results are in kcal/mol
Parameters with C:G pairs are from (23).

TABLE 9

The Experimental and Predicted Free Energy changes and $T_m$'s for the 16 tandem S:B, Z:P containing duplexes used in the plots shown in FIG. 11 and FIG. 12. The experimental values are the error-weighted average of thermodynamic values from curve fit and $T_m$-1 methods of analysis (see Table 10).

| | Pred. ΔG°$_{37}$ (kcal/mol) | Expt. ΔG°$_{37}$ (kcal/mol) | Pred. $T_m$ ($1e^{-4}$M) | Exp. $T_m$ ($1e^{-4}$M) |
|---|---|---|---|---|
| Self-Complementary Duplex | | | | |
| CSZATPBG | −8.75 | −8.30 | 57.6 | 56.9 |
| CSPATZBG | −9.40 | −9.14 | 57.5 | 57.2 |
| CZSATBPG | −9.47 | −9.24 | 61.2 | 62.4 |
| CZBATSPG | −10.30 | −10.32 | 63.1 | 62.7 |
| GSPTAZBC | −9.56 | −9.27 | 61.8 | 61.6 |
| GZSTABPC | −7.93 | −8.58 | 50.9 | 57.6 |
| CZBTASPG | −9.88 | −9.85 | 63.0 | 62.3 |
| GSZATPBC | −9.43 | −9.50 | 63.4 | 60.2 |
| GSPATZBC | −10.08 | −10.51 | 62.2 | 63.7 |
| GZSATBPC | −8.48 | −8.81 | 60.0 | 61.9 |
| GZBATSPC | −9.32 | −9.57 | 62.7 | 62.4 |
| GAZSBPTC | −8.85 | −8.13 | 59.4 | 49.1 |
| GTPBSZAC | −9.54 | −10.12 | 62.6 | 65.5 |
| CBZATPSG | −8.93 | −9.03 | 63.2 | 62.8 |
| GBZTAPSC | −8.71 | −8.61 | 61.5 | 61.7 |
| CTTATPPSBZZATAAG* SEQ ID NO 2 | −17.93 | −16.46 | 77.0 | 81.3 |

* This 16mer duplex is non-two-state due to competing hairpin formation, slow kinetics, and limited high-temperature baseline. It is presented for validation purposes, but was not used to derive NN parameters.

TABLE 10

The raw data obtained for duplex melts containing S-B, Z-P nearest-neighbors in 1M NaCl, 10 mM $Na_2HPO_4$, and 0.5 mM $Na_2EDTA$, pH 7.00 buffer. All data were fit using the thermodynamic analysis software Meltwin v.3.5.

| | $T_m^{-1}$ Method | | | | Curve Fit Method | | |
|---|---|---|---|---|---|---|---|
| Duplex | ΔH° (kcal/mol) | ΔS° (cal/mol * K) | ΔG°$_{37}$ (kcal/mol) | $T_m$ ($1e^{-4}$M) | ΔH° (kcal/mol) | ΔS° (cal/mol * K) | ΔG°$_{37}$ (kcal/mol) |
| CSZATPBG | −41.5 ± 10.1 | −107.4 ± 31.3 | −8.20 ± 0.69 | 56.7 | −44.2 ± 6.1 | −115.7 ± 18.7 | −8.32 ± 0.34 |
| CSPATZBG | −50.8 ± 14.1 | −135.1 ± 43.0 | −8.87 ± 1.11 | 57.1 | −57.8 ± 6.2 | −156.9 ± 18.9 | −9.18 ± 0.42 |
| CZSATBPG | −44.6 ± 4.6 | −114.3 ± 14.0 | −9.12 ± 0.23 | 62.2 | −50.2 ± 5.1 | −131.7 ± 15.4 | −9.41 ± 0.27 |
| CZBATSPG | −60.3 ± 4.7 | −161.2 ± 14.4 | −10.29 ± 0.27 | 62.7 | −61.0 ± 4.6 | −163.3 ± 13.9 | −10.35 ± 0.30 |
| CSZTAPBG* | NTS | | | NTS | | | NTS |
| GSPTAZBC | −43.9 ± 16.1 | −112.3 ± 49.3 | −9.07 ± 1.23 | 61.6 | −48.9 ± 1.8 | −127.8 ± 5.5 | −9.27 ± 0.10 |
| GZSTABPC | −46.2 ± 5.8 | −121.4 ± 18.1 | −8.58 ± 0.30 | 57.8 | −46.6 ± 2.8 | −122.5 ± 9.1 | −8.58 ± 0.10 |
| CZBTASPG | −53.8 ± 5.9 | −142.2 ± 18.1 | −9.75 ± 0.36 | 61.9 | −58.2 ± 8.1 | −155.4 ± 24.7 | −10.02 ± 0.47 |
| GSZATPBC | −51.9 ± 14.7 | −137.4 ± 44.6 | −9.33 ± 1.24 | 60.0 | −56.0 ± 9.3 | −149.8 ± 28.2 | −9.53 ± 0.55 |
| GSPATZBC | −59.9 ± 3.4 | −159.6 ± 10.2 | −10.45 ± 0.20 | 63.6 | −63.1 ± 4.8 | −169.1 ± 14.4 | −10.65 ± 0.29 |
| GZSATBPC | −40.2 ± 5.3 | −101.6 ± 16.4 | −8.72 ± 0.28 | 61.4 | −42.9 ± 3.2 | −110.0 ± 9.9 | −8.84 ± 0.17 |

TABLE 10-continued

The raw data obtained for duplex melts containing S-B, Z-P nearest-neighbors in 1M NaCl, 10 mM Na$_2$HPO$_4$, and 0.5 mM Na$_2$EDTA, pH 7.00 buffer. All data were fit using the thermodynamic analysis software Meltwin v.3.5.

| | $T_m^{-1}$ Method | | | | Curve Fit Method | | |
|---|---|---|---|---|---|---|---|
| Duplex | ΔH° (kcal/mol) | ΔS° (cal/mol * K) | ΔG°$_{37}$ (kcal/mol) | T$_m$ (1e$^{-4}$M) | ΔH° (kcal/mol) | ΔS° (cal/mol * K) | ΔG°$_{37}$ (kcal/mol) |
| GZBATSPC | −47.1 ± 4.5 | −121.5 ± 14.0 | −9.40 ± 0.24 | 61.9 | −53.7 ± 3.3 | −141.9 ± 9.9 | −9.71 ± 0.22 |
| GAZSBPTC | −64.8 ± 5.4 | −182.8 ± 17.2 | −8.12 ± 0.12 | 61.9 | −65.1 ± 1.7 | −183.7 ± 5.3 | −8.13 ± 0.06 |
| GTPBSZAC | −52.3 ± 2.6 | −136.1 ± 7.9 | −10.10 ± 0.14 | 61.9 | −54.4 ± 4.9 | −142.4 ± 14.9 | −10.23 ± 0.33 |
| CBZATPSG | −41.6 ± 14.2 | −105.8 ± 42.9 | −8.59 ± 1.16 | 61.9 | −44.2 ± 7.5 | −113.2 ± 22.5 | −9.11 ± 0.49 |
| GBZTAPSC | −39.6 ± 1.3 | −99.9 ± 3.8 | −8.60 ± 0.06 | 61.9 | −41.6 ± 3.2 | −106.0 ± 9.8 | −8.71 ± 0.16 |
| CTTATPPSB ZZATAAG** SEQ ID NO 2 | −83.9 ± 9.3 | −218.1 ± 27.0 | −16.22 ± 0.96 | 81.3 | −83.6 ± 1.4 | −225.2 ± 44.1 | −16.46 ± 0.13 |

*The 8mer did not give a discernable melting transition and thus is listed as NTS = non-two-state.
**This 16mer duplex is non-two-state due to competing hairpin formation, slow kinetics, and limited high-temperature baseline. It is presented for validation purposes, but was not used to derive NN parameter.

Example 2. Transcribing 8-Letter DNA

8-Letter Transcription and Purification

The sense and antisense DNA analog strands were made by solid phase synthesis, as with the oligonucleotide analogs used in melting temperature. Templates were annealed by independently mixing equimolar ratios of top and bottom strands in 20 mM NaCl, 40 mM Tris pH 7.8, 6 mM MgCl2, 2 mM spermidine, 10 mM dithiothreitol, heating to 90° C. for 1 min followed by cooling to room temperature at 0.1° C./sec.

Transcriptions contained 0.2 μM template, 40 mM Tris (pH 7.8), 20 mM NaCl, 2 mM spermidine, 10 mM dithiothreitol, 2 mM each of appropriate rNTPs, 0.2 μCi/μL alpha labeled triphosphate (α$^{32}$P-CTP or α$^{32}$P-GTP) and either 16 mM (standard transcription with rGTP, rATP, rCTP, UTP), 18 mM (control transcriptions with one AEGIS ribotriphosphate and rGTP, rATP, rCTP, UTP) or 24 mM MgCl$_2$ (8-letter transcriptions with rGTP, rATP, rCTP, UTP, rPTP, rZTP, rBTP, and rSTP). Transcriptions were initiated with the addition of T7 RNA polymerase (0.175 μg/μL). After incubation (37° C., 16 hours), samples were processed with phenol: chloroform:isoamyl alcohol (24:24:1) to remove proteins followed by ethanol precipitation and polyacrylamide gel purification (7 M urea). RNA was extracted in 0.3 M sodium acetate, recovered by ethanol precipitation, quantified by UV spectroscopy and used in subsequent analysis. T7 RNA polymerase variants and control and aptamer sequences are outlined in Table 11 and Table 12, respectively.

Model T2-templates (T2N) that have only one non-standard nucleotide (N) and Am was 2'O methyl riboA, or alternatively, 2'-methoxy deoxyriboadenosine.

T2S:
SEQ ID NO 3
5'-GGC GTA ATA CGA CTC ACT ATA GGG AGT GTT GTA TT T GGS CAA T T T

SEQ ID NO 4
3'-CCG CAT TAT GCT GAG TGA TAT CCC TCA CAA CAT AA A CCB GTT Am Am A

T2B
SEQ ID NO 5
5'-GGC GTA ATA CGA CTC ACT ATA GGG AGT GTT GTA TT T GGB CAA T T T

SEQ ID NO 6
3'-CCG CAT TAT GCT GAG TGA TAT CCC TCA CAA CAT AA A CCS GTT Am Am A

T2Z
SEQ ID NO 7
5'-GGC GTA ATA CGA CTC ACT ATA GGG AGT GTT GTA TT T GGZ CAA T T T

SEQ ID NO 8
3'-CCG CAT TAT GCT GAG TGA TAT CCC TCA CAA CAT AA A CCP GTT Am Am A

T2P
SEQ ID NO 9
5'-GGC GTA ATA CGA CTC ACT ATA GGG AGT GTT GTA TT T GGP CAA T T T

SEQ ID NO 10
3'-CCG CAT TAT GCT GAG TGA TAT CCC TCA CAA CAT AA A CCZ GTT Am Am A

T7 RNA Polymerase Variant Development

The following variants of T7 RNA polymerase were examined.

TABLE 11

T7 RNA Polymerases Examined in this Research

| Amino acid replacements relative to native T7 RNA polymerase | name |
|---|---|
| None | wild type, native |
| Y639F | F variant |
| Y639F P266L | FL variant |
| Y639F H784A | FA variant |
| Y639F H784A P266L | FAL variant |
| G542V H772R H784S | VRS variant |

Oligonucleotides Containing a Single Non-Standard 8-Letter Component for Polymerase Screen To identify T7 RNA polymerases able to incorporate 8-letter ribonucleotides by transcription of 8-letter DNA, a series of template-promoter sequences were designed having a single 8-letter non-standard component, followed by a unique cytidine. In each, transcription with alpha $^{32}$P-labeled CTP would create an RNA product with a bridging $^{32}$P-labeled phosphate. Upon digestion with ribonuclease T2, this phosphate would end up bonded at the 3'-OH of the 8-letter nucleoside-3'-phosphate

TABLE 12

RNA generated by T7 RNA polymerase

T2P: Incorporating a single 8-letter P
    SEQ ID NO 11
5'-GGG AGU GUU GUA UUU GGP CAA UUU
Transcription with a32P-CTP then digestion with
RNase T2 yields labeled P-3'-phosphate.

T2Z: Incorporating a single 8-letter Z
    SEQ ID NO 12
5'-GGG AGU GUU GUA UUU GGZ CAA UUU
Transcription with a32P-CTP then digestion with
RNase T2 yields labeled Z-3'-phosphate.

T2B: Incorporating a single 8-letter B
    SEQ ID NO 13
5'-GGG AGU GUU GUA UUU GGB CAA UUU
Transcription with a32P-CTP then digestion with
RNase T2 yields labeled B-3'-phosphate.

T2S: Incorporating a single 8-letter S
    SEQ ID NO 1
5'-GGG AGU GUU GUA UUU GGS CAA UUU
Transcription with a32P-CTP then digestion with
RNase T2 yields labeled S-3'-phosphate.

Spinach aptamer with four non-standard 8-letter
components
    SEQ ID NO 14
5'-GGA CGC GBC ZGA AAU GGU GAA GGA CGG GUC CAG
UGC GAA ACA CGC ACU GUU GAG UAG AGU GUG AGC UCC
GUA ACU PGS CGC GUC-3'

Preliminary Run-Off Experiments with T7 RNA Polymerase Variants

Figure 13:
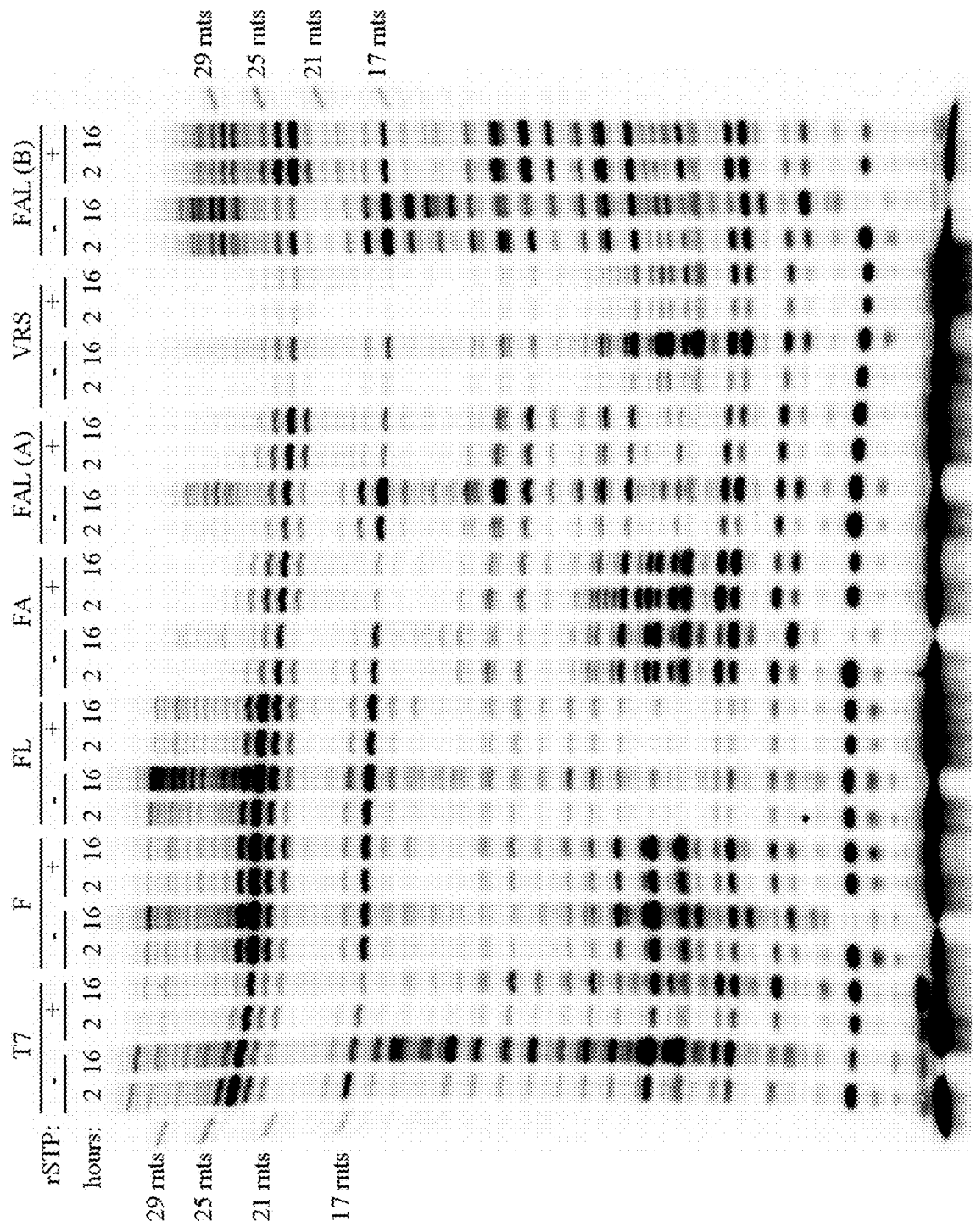
FIG. 13. PAGE (20%) showing transcription products with internal labeling. Wild type and mutant T7 RNA polymerases were tested in the absence and presence of rSTP for their ability to generate the RNA product T2S; they show different levels of pausing and rescue. Full length product is a 24mer, S is at position 18; pausing is most prominent at position 17. T7, the FA variant (with Y639F and H784A replacements, the "FL variant") and the FAL variant (with Y639F, H784A, and P266L replacements, the "FAL variant") show pausing in the absence of riboSTP and various levels of rescue in the presence of riboSTP. The experimental data are collected in clusters of four sequences with the top cluster being the variant of T7 RNA polymerase (native, F, FL, FA, FAL (A), VRS, and FAL (B), the last at lower concentration), each having two lanes without riboSTP, and two lanes with riboSTP, with incubation times of 2 and 16 hours. The variants are defined as Y639F, Y639F P266L, FIG. 14 A-FIG. 14 C. HPLC (ammonium bicarbonate, 0 to 200 mM) traces of the rN-3'-monophosphates recovered by RNase T2 digestion of the RNA made by attempts with different RNA polymerase variants to make 8-letter spinach. (A) Trace from RNA made via transcription using wild-type T7 RNA polymerase. Note absence of S-3'-P. (B) Trace from RNA made via transcription using the FAL variant of T7 RNA polymerase. Note detectable presence of S-3'-P, notwithstanding its low extinction coefficient and its expected presence in the transcript as only one exemplar. (C) Trace from RNA made via transcription using the FAL variant T7 RNA polymerase, with co-injection of the authentic rS-3'-monophosphate made by chemical synthesis. The expected 8-letter transcript is.

Wild-type T7 RNA polymerase did not readily incorporate STP opposite template dB, even though it accepted the other non-standard components. Therefore, we engaged in an extensive research program to identify variants of T7 RNA polymerase that did. The results of screening of several of these for their ability to incorporate STP opposite template dB are shown in FIG. 13.

Here, internal P32 labeling was done so that we could observe all of the failure sequences. While many of the variants had improved ability to incorporate STP opposite template dB, the triple mutant Y639F H784A P266L (FAL) stood out. It shows no detectable deficit in fidelity and only modestly slower rate. However, it is thermostable and accepts 2'-O-methyl ribonucleoside triphosphates (34). Essentially all experiments were done with this variant.

The T7 duplex was prepared by mixing equimolar ratios of top strand (T2-templateS) and bottom strand (T2-templateS-comp) in 1× transcription buffer (20 mM NaCl, 40 mM Tris pH 7.8, 6 mM $MgCl_2$, 2 mM spermidine, and 10 mM DTT), heating to 90° C., and then slowly cooling to room temperature.

The transcription reaction mixtures contained a final concentration of 1 µM annealed template duplex, 1× transcription buffer (20 mM NaCl, 40 mM Tris pH 7.8, 18 mM $MgCl_2$, 2 mM spermidine, and 10 mM DTT), 2 mM of each rNTP (in minus assays rSTP was omitted), 0.5 µCi/µL $\alpha^{32}$P-GTP and T7 RNA polymerase (0.025 µg/µL or 0.175 µg/µL of the FAL variant). Reaction mixtures were incubated at 37° C. for 2 hours and overnight. Reactions were quenched with 3× formamide quench buffer and samples were resolved on a 20% PAGE.

PAGE (20%) was used to resolve transcription products using internal labeling. Wild type and mutant T7 RNA polymerases were tested in the absence and presence of rSTP to show pausing and rescue. Full length product is a 24mer, S is at position 18 with pausing most prominent at position 17, depending on the variant. Specifically, the T7, FA and FAL mutants show pausing in the absence of rSTP and various levels of rescue in the presence of rSTP.

Variants of T7 RNA polymerase produce full length product (24mer) in the absence and presence of rSTP. A prominent "failure" band appears in the absence of rSTP with these variants, suggesting that the polymerase has difficulty further extending a primer with a mismatched end, where one of the standard nucleotides is mismatched against template dB. This pausing is rescued in the presence of rSTP. As seen in FIG. 13, the failure band is most prominent at position 17, one base before the AEGIS site where S is called for; rescue increases with wild type, FA and FAL mutants.

Sample Preparation for Fluorescence of Spinach

Purified RNA was refolded in folding buffer containing 10 mM Tris (pH 7.5), 100 mM $K^+$ and 5 mM $Mg^{2+}$ (the RNA sample was heated at 90° C. for one minute in water followed by incubation on ice for 3 minutes and at room temperature for 5 minutes, then diluted into folding buffer and heated at 55° C. for 30 minutes followed by incubation on ice for 5 minutes). Two equivalents of the Spinach fluorophore, DFHBI ((5Z)-5-[(3,5-difluoro-4-hydroxyphenyl)methylene]-3,5-dihydro-2,3-dimethyl-4H-Imidazol-4-one, (Z)-4-(3,5-Difluoro-4-hydroxybenzylidene)-1,2-dimethyl-1H-imidazol-5(4H)-one) was added and the mixture was incubated at 37° C. for 30 min.

Fluorescence Spectroscopy of Spinach Variants

Fluorescence emission was measured using a Fluorolog-3 spectrofluorometer equipped with a thermo-controller (Horiba Inc.) at an excitation wavelength of 468 nm and emission range of 490-520 nm with a slit width of 5 nm; reported results are the average of three consecutive independent measurements, and each measurement was performed in triplicate (the data points represent the average of these triplicate measurements). Experiments were performed at 25° C. Data were normalized and plotted in Microsoft Excel. The concentrations of RNA and fluorophore were 5 µM and 20 µM, respectively.

Example 3. Analytical Chemistry of 8-Letter RNA

HPLC analysis of RNA transcripts containing riboS (FIG. 2).

The ability of the FAL variant to incorporate STP opposite template dB was shown first using HPLC analysis. Here, product RNA was treated with RNase T2, which does near total degradation to give nucleoside 3'-phosphates. These were separated by ion exchange HPLC using ammonium bicarbonate gradients (aqueous, from 0 to 200 mM).

Figure 14:
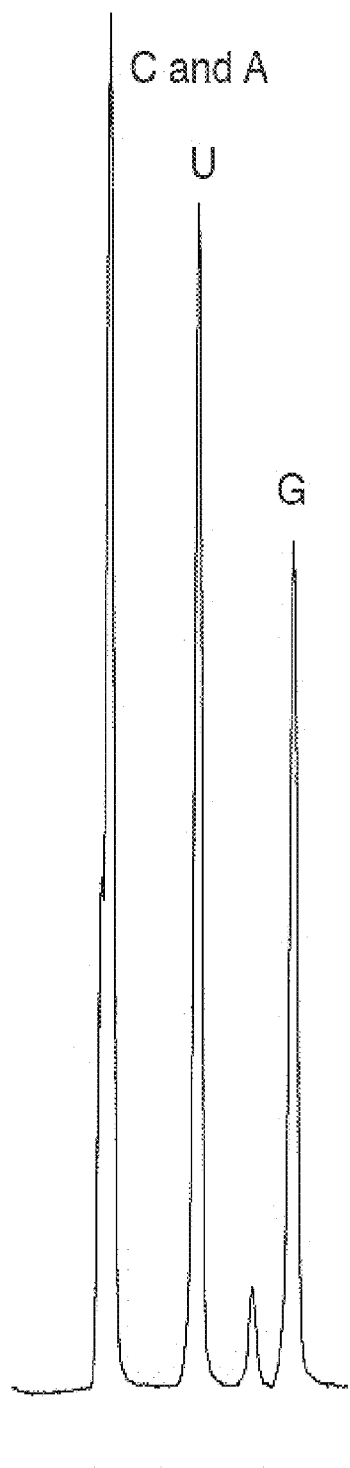
Figure 14:
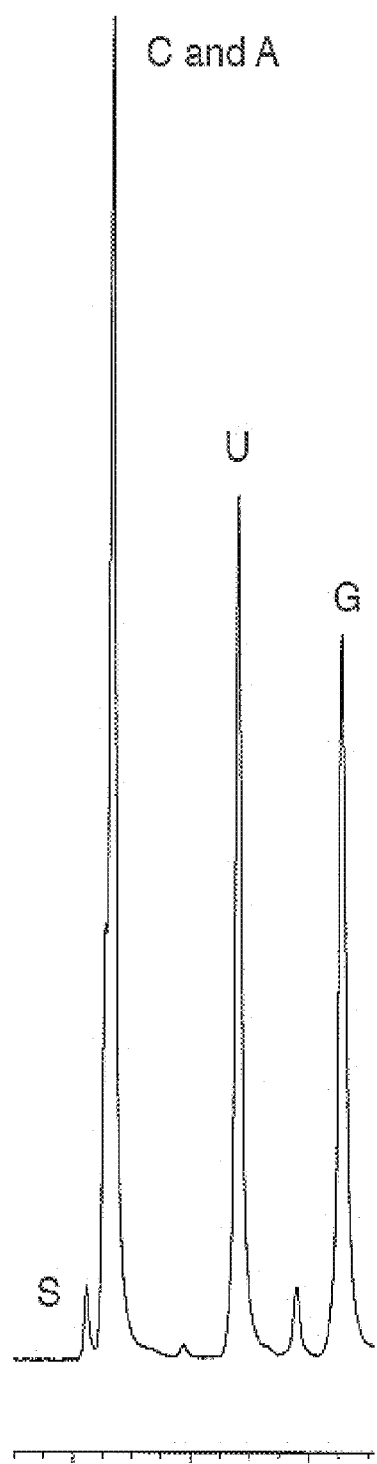
Figure 14:
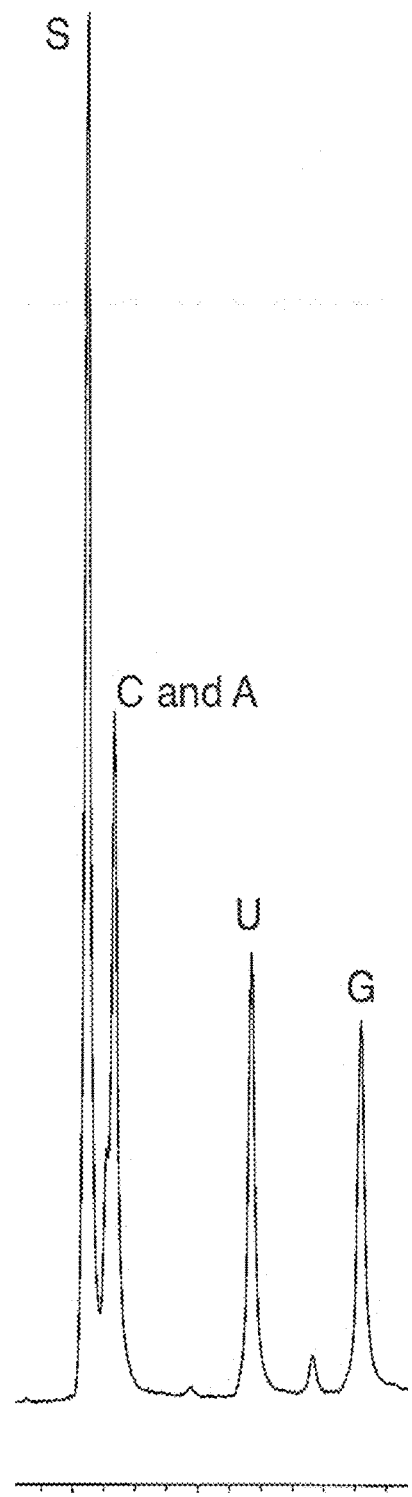

FIG. 14 shows the HPLC traces of the rN-3'-monophosphates recovered by RNase digestion of products made with wild type T7 RNA polymerase and its FAL variant (respectively). The expected transcript is:

GGG ΔGU GUU GUA UUU GGS CAA UUU SEQ ID NO 1 (also in Description)

The following extinction coefficients at 260 nm were used to quantitate the nucleoside 3'-phosphates from the HPLC trace, estimated at pH 7.0.

15400, A-3'-phosphate (4 exemplars in the 8-letter transcript), relative absorbance 62600

11700, G-3'-phosphate (8 exemplars in the 8-letter transcript), relative absorbance 93600

7300, C-3'-phosphate (1 exemplars in the 8-letter transcript), relative absorbance 7300

8800, U-3'-phosphate (10 exemplars in the 8-letter transcript), relative absorbance 88000

6300, S-3'-phosphate (1 exemplar in the 8-letter transcript), relative absorbance 6300

The reference peaks show significant variance, of course. However, the average using C+A, U, and G as three independent internal standards indicates that 1.2±0.4 equivalents of S are incorporated per transcript prepared by the FAL variant of T7 RNA polymerase; no S was detectable by HPLC using the wild-type T7 RNA polymerase. This indicates the value of protein engineering to create 8-letter transcripts.

TABLE 13

| Peak | Expected | Expected ratio (S = 1) | Observed peak | Observed ratio | Amount of S calculated using the index peak as reference |
|---|---|---|---|---|---|
| C + A | 69900 | 11 | 0.065 | 16 | 0.68 |
| G | 93600 | 15 | 0.037 | 9 | 1.7 |
| U | 88000 | 14 | 0.043 | 11 | 1.3 |
| average | | | | | 1.2 ± 0.4 equivalents of S per transcript |

The increased intensity of the U peak relative to the others in the left trace (made with wild-type T7 RNA polymerase) is consistent with a model whereby wild-type T7 RNA polymerase incorporates U opposite template dB, due to the presence of a minor tautomer of dB that is Watson-Crick complementary to U. This would generate a transcript with 11 U's instead of 10 U's. The peak at 11.5 min is unassigned, HPLC Analysis of 8-Letter Spinach Containing S, B, Z and P.

Notwithstanding the overlapping of peaks, HPLC proved to be a useful way to identify 8-letter Z-3-phosphate in RNase T2 digests. FIG. 15 shows an HPLC analysis of 8-letter spinach RNA transcripts containing 8-letter S-3'-phosphate, P-3'-phosphate, B-3'-phosphate, and Z-3'-phosphate. Possibly because Z has a nitro group, it comes late in the ion exchange HPLC (ammonium bicarbonate gradient, as before).

The Z-3'-phosphate comes late, as confirmed by its co-elution with authentic material made by synthesis. Even though it represents only one nucleotide out of 86, its large extinction coefficient due to its nitro group makes its signal strong.

In contrast, at 260 nm, B-3'-phosphate gives a relatively weak signal; its $\lambda_{max}$ is at 290 nm; 260 nm is close to an absorbance minimum. Of course, B can affirmatively identified in this digest because of this unusual UV absorbance property, as well as its co-elution with authentic B-3'-phosphate made by chemical synthesis. S-3'-phosphate and P-3'-phosphate co-elute by HPLC (as do A-3'-phosphate and C-3'-phosphate). Thus, the digestion product mixture shows all eight 8-letter nucleotides in the transcript made by the FAL variant of T7 RNA polymerase. However, the presence of A or C and S or P remains incompletely established, due to co-elution in the HPLC. This required us to develop alternative tools to do analysis of 8-letter RNA (see next section).

Label Shift Analysis

Classical two dimensional thin layer chromatography (2D-TLC) was adapted to allow analysis of 8-letter RNA. In these assays, one of four standard RNA triphosphates is introduced into a transcription mixture with an alpha-$^{32}$P label. This leads to a product with a bridging $^{32}$P phosphate. Subsequent hydrolysis by RNase T2 generates a mixture of nucleoside 3'-phosphates, where the 3'-nucleotide immediately preceding in the sequence carries a $^{32}$P-label. The mixture of nucleoside 3'-phosphates is then resolved by chromatography to determine the adjacency patterns of the system.

Thus, in the various model products, incorporation of alpha-$^{32}$P labeled CTP will generate only a labeled S-3'-$^{32}$P product, only Z-3'-$^{32}$P product, only P-3'-$^{32}$P product, or only B-3'-$^{32}$P product, depending on the template. These are resolved by chromatography.

Following incubation with T7 RNA polymerase, transcripts were PAGE purified, digested with T2 ribonuclease (100 units) (Worthington Biochemical Corporation) by incubation at 37° C. for 16 hours in 15 mM sodium acetate buffer pH 4.5. For each sample, approximately 1500 cpm was spotted on polyethyleneimine plates (PEI: 20 cm×20 cm plates) (Sorbent Technologies), dried under flowing air, and run in the first dimension with first dimension buffer. The plate was then dried, turned 90°, and then run in the second dimension buffer. The plates were dried, exposed to a phosphorimager screen and analyzed with a Biorad Personal Molecular Imager (PMI) System.

Primary Solvent System for Two Dimensional Thin Layer Chromatography

The solvent system for the first dimension was: isobutyric acid-ammonia-water (66:1:33 v/v/v) and the solvent system for the second dimension was: 2-propanol-HCl-water (70:15:15 v/v/v).

Secondary Solvent System for Two Dimensional Thin Layer Chromatography

A new solvent system was developed to get better separation of the nucleoside 3'-phosphates obtained by digestion by T2 ribonuclease of the products of transcription of 8-letter DNA. Here, the first dimension was: isobutyric acid-ammonia-water (66:1:33 v/v/v) and the second dimension was: aqueous saturated NH$_4$SO$_4$ (~140 g) with NH$_4$HSO$_4$ (~0.8 g) in 200 mL, pH 3.2.

In this solvent system shown in FIG. 17, Z co-migrates with G instead of with U. Further, with wild-type T7 RNA polymerase, instead of a spot corresponding to S-$^{32}$P in the SBZP sample, U appears to be labeled when wild-type T7 RNA polymerase is used. This is consistent with earlier results showing that wild-type T7 RNA polymerase incorporates STP only poorly opposite template dB [Switzer, C. Y., Moroney, S. E., Benner, S. A. (1993) *Biochemistry* 32, 10489-10496]; as in other systems, U is the preferred mismatch for B in the absence of S, presumably because of the minor tautomer of B.

Incorporation of STP Opposite B by the FAL Variant of T7 RNA Polymerase

The solvent system for the first dimension was: isobutyric acid-ammonia-water (66:1:33 v/v/v) and the solvent system for the second dimension was: 2-propanol-HCl-water (70:15:15 v/v/v).

The first dimension was: isobutyric acid-ammonia-water (66:1:33 v/v/v) and the second dimension was: aqueous saturated NH$_4$SO$_4$ (~140 g) with NH$_4$HSO$_4$ (~0.8 g) in 200 mL, pH 3.2.

Example 4: Synthesis of Authentic Non-Standard 3'-Phosphates riboB-3'-Phosphate as Authentic Standard (FIG. 2)

Synthesis of 3'AMP N Oxide

To a solution of 3'-AMP (5 μmol) and saturated NaHCO$_3$ aqueous solution (12.5 μL), 1.2 M mCPBA/MeOH (25 μL) was added. The reaction mixture was stirred for 6 h at room temperature, and H$_2$O (125 µL) was added. After 10 min at 0° C., precipitates were removed by filtration through a syringe filter. The filtrate was purified by DNA-pak ion exchange HPLC (eluted by a linear gradient of 0-0.5M ammonium bicarbonate buffer) to yield the fractions containing the desired nucleoside 3'-monophosphate N oxide. The fractions were collected and concentrated in vacuo. Product obtained 3'AMP N oxide (45 mg, 123 µmol from 144 µmol of 3'-AMP)

Synthesis of 3'-Isoguanosine Monophosphate (B-3'-P) from 3'-AMP N oxide

N-oxide of 3'AMP (123 µmol, 45 mg) was dissolved in water (2 mL) and the solution was placed in a quartz cuvette. The mixture was irradiated for 16 h (loss of absorbance at 232 nm indicated completion of reaction). The solution was filtered through a 0.45 micron filter and the material was purified by HPLC (DNA-pak ion-exchange column). The product was eluted by a linear gradient of 0-0.5M ammonium bicarbonate buffer to yield the fractions containing the desired IsoG nucleoside 3'-monophosphate. The product was 3'-isoGMP (3.5 mg, 9.6 µmol from 123 µmol of 3'AMP N oxide).
riboS-3'-phosphate as Authentic Standard (FIG. 2)

Protected N-dimethylformamidyl 5'-DMT 2'-TBDMS rS phosphoramidite (0.1 mmol) was treated with 3-hydroxy-propionitrile (0.2 mmol) in presence of 5-ethylthio-1H-tetrazole (0.2 mmol) in acetonitrile (0.8 mL) for 3 hours. The reaction mixture was evaporated and then 6 mL of 0.02 M Iodine in THF/pyridine/water was added. After 10 minutes, 1.0 mL of 5% aq. Na$_2$SO$_3$ was added and then the reaction mixture was evaporated. After the residue was co-evaporated with toluene twice, 80% AcOH was added and stirred for 20 min. The reaction mixture was evaporated and co-evaporated with toluene three times. To the residue, conc. NH$_4$OH:EtOH (3:1) was added and stirred at 55° C. overnight. After evaporation, 0.3 mL of DMSO and 0.3 mL of TEA.3HF were added and stirred at 55° C. for 3 hours. The reaction mixture was evaporated and then dissolved in water. The solution was washed with EtOAc.
riboZ-3'-phosphate as Authentic Standard (FIG. 2)

Protected O-NPE N-acetyl 5'-DMT 2'-thiocarbamoylpyrrolidine sulfone rZ phosphoramidite (0.1 mmol) was treated with 3-hydroxypropionitrile (0.2 mmol) in presence of 5-ethylthio-1H-tetrazole (0.2 mmol) in acetonitrile (0.8 mL) for 3 hours. The reaction mixture was evaporated and then 6 mL of 0.02 M Iodine in THF/pyridine/water was added. After 10 minutes, 1.0 mL of 5% aq. Na$_2$SO$_3$ was added and then the reaction mixture was evaporated. After the residue was co-evaporated with toluene twice, 80% AcOH was added and stirred for 20 min. The reaction mixtures were evaporated and co-evaporated with toluene three times. The residue was treated with 1.0 M DBU in acetonitrile (2 mL) overnight. After evaporation, the residue was treated with 2.0 mL of ethylenediamine for 2 hours. The reaction mixture was evaporated and then dissolved in water. The solution was washed with EtOAc.
riboP-3'-phosphate as Authentic Standard (FIG. 2)

Protected N-dibutylformamidine 2'-thiocarbamoylpyrrolidine sulfone rP phosphoramidite (0.1 mmol) was treated with 3-hydroxypropionitrile (0.2 mmol) in presence of 5-ethylthio-1H-tetrazole (0.2 mmol) in acetonitrile (0.8 mL) for 3 hours. The reaction mixture was evaporated and then 6 mL of 0.02 M Iodine in THF/pyridine/water was added. After 10 minutes, 1.0 mL of 5% aq. Na$_2$SO$_3$ was added and then the reaction mixture was evaporated. After the residue was co-evaporated with toluene twice, 80% AcOH was added and stirred for 20 min. The reaction mixtures were evaporated and co-evaporated with toluene three times. The residue was treated with 2.0 mL of ethylenediamine for 2 hours. The reaction mixture was evaporated and then dissolved in water. The solution was washed with EtOAc.

What is claimed is:

1. A process for synthesizing RNA containing one or more non-standard nucleotides, wherein said process comprises contacting in aqueous solution
   (a) a variant of T7 RNA polymerase that can accept non-standard nucleoside triphosphates that do not present electron density to the minor groove with
   (b) a DNA template comprising a promoter for said variant, and
   (c) nucleoside triphosphates that
comprise one or more independently selected heterocycles selected from the group consisting of

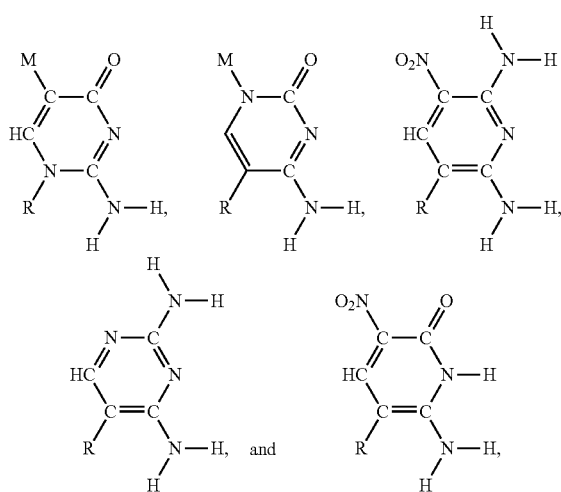

wherein M is an alkyl, alkenyl, or alkynyl substituent, either simple or functionalized, and R is the point of attachment of said heterocycle(s) to the ribose ring of said nucleoside triphosphate(s).

2. The process of claim 1, wherein said variant to T7 RNA polymerase has amino acids replaced at individual sites in its polypeptide sequence, wherein said replacements comprise a replacement of tyrosine at position 639 by phenylalanine, a replacement of histidine at position 784 by alanine, and a replacement of proline at position 266 by leucine.

3. The process of claim 1, wherein said nucleoside triphosphates comprise one or more independently selected heterocycles selected from the group consisting of

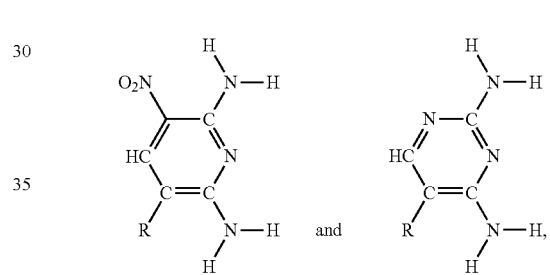

and M is an alkyl, alkenyl, or alkynyl substituent, either simple or functionalized, and R is the point of attachment of said heterocycle(s) to the ribose ring of said nucleoside triphosphate(s).

4. The process of claim 3, wherein M is methyl.

5. The process of claim 1, wherein said nucleoside triphosphates comprise one or more independently selected heterocycles selected from the group consisting of

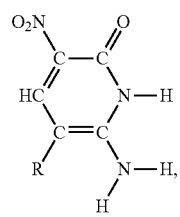

and R is the point of attachment of said heterocycle(s) to the ribose ring of said nucleoside triphosphate(s).

6. The process of claim 1, wherein said nucleoside triphosphate(s) comprise(s) the heterocycle

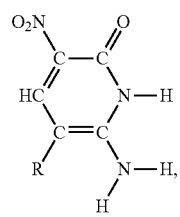

wherein R is the point of attachment of said heterocycle(s) to the ribose ring of said nucleoside triphosphate(s).

* * * * *

SEQUENCE LISTING

```
<160> NUMBER OF SEQ ID NOS: 14

<210> SEQ ID NO 1
<211> LENGTH: 24
<212> TYPE: RNA
<213> ORGANISM: Artificial Sequence
<220> FEATURE:
<223> OTHER INFORMATION: synthetic
<220> FEATURE:
<221> NAME/KEY: misc_feature
<222> LOCATION: (18)..(18)
<223> OTHER INFORMATION: 3-methyl-6-amino-5-(1'-beta-D-ribofuranosyl)-
      pyrimidin-2-one

<400> SEQUENCE: 1
gggaguguug uauuuggnca auuu                                          24

<210> SEQ ID NO 2
<211> LENGTH: 16
<212> TYPE: DNA
<213> ORGANISM: Artificial Sequence
<220> FEATURE:
<223> OTHER INFORMATION: synthetic
<220> FEATURE:
<221> NAME/KEY: misc_feature
<222> LOCATION: (6)..(7)
<223> OTHER INFORMATION: 2-amino-8-(beta-D-2'-deoxyribofuranosyl)-
      imidazo-[1,2a]-1,3,5-triazin-[8H]-4-one
<220> FEATURE:
```

```
<221> NAME/KEY: misc_feature
<222> LOCATION: (8)..(8)
<223> OTHER INFORMATION: 3-methyl-6-amino-5-(1'-beta-D-2'-
      deoxyribofuranosyl)-pyrimidin-2-one
<220> FEATURE:
<221> NAME/KEY: misc_feature
<222> LOCATION: (9)..(9)
<223> OTHER INFORMATION: 6-amino-9-(1'-beta-D-2'-deoxyribofuranosyl)4-
      hydroxy-5-(hydroxymethyl)oxolan-2-yl]-1H-purin-2-one
<220> FEATURE:
<221> NAME/KEY: misc_feature
<222> LOCATION: (10)..(11)
<223> OTHER INFORMATION: 6-amino-3-(2'-deoxy)-D-ribofuranosyl)-5-nitro-
      1H-pyridin-2-one

<400> SEQUENCE: 2
cttatnnnnn nataag                                               16

<210> SEQ ID NO 3
<211> LENGTH: 45
<212> TYPE: DNA
<213> ORGANISM: Artificial Sequence
<220> FEATURE:
<223> OTHER INFORMATION: synthetic
<220> FEATURE:
<221> NAME/KEY: misc_feature
<222> LOCATION: (39)..(39)
<223> OTHER INFORMATION: 3-methyl-6-amino-5-(1'-beta-D-2'-
      deoxyribofuranosyl)-pyrimidin-2-one

<400> SEQUENCE: 3
ggcgtaatac gactcactat agggagtgtt gtatttggnc aattt               45

<210> SEQ ID NO 4
<211> LENGTH: 45
<212> TYPE: DNA
<213> ORGANISM: Artificial Sequence
<220> FEATURE:
<223> OTHER INFORMATION: synthetic
<220> FEATURE:
<221> NAME/KEY: misc_feature
<222> LOCATION: (7)..(7)
<223> OTHER INFORMATION: 6-amino-9-(1'-beta-D-2'-deoxyribofuranosyl)4-
      hydroxy-5-(hydroxymethyl)oxolan-2-yl]-1H-purin-2-one

<400> SEQUENCE: 4
aaattgncca aatacaacac tccctatagt gagtcgtatt acgcc               45

<210> SEQ ID NO 5
<211> LENGTH: 45
<212> TYPE: DNA
<213> ORGANISM: Artificial Sequence
<220> FEATURE:
<223> OTHER INFORMATION: synthetic
<220> FEATURE:
<221> NAME/KEY: misc_feature
<222> LOCATION: (39)..(39)
<223> OTHER INFORMATION: 6-amino-9-(1'-beta-D-2'-deoxyribofuranosyl)4-
      hydroxy-5-(hydroxymethyl)oxolan-2-yl]-1H-purin-2-one

<400> SEQUENCE: 5
ggcgtaatac gactcactat agggagtgtt gtatttggnc aattt               45

<210> SEQ ID NO 6
<211> LENGTH: 45
<212> TYPE: DNA
<213> ORGANISM: Artificial Sequence
<220> FEATURE:
<223> OTHER INFORMATION: synthetic
<220> FEATURE:
<221> NAME/KEY: misc_feature
```

```
<222> LOCATION: (7)..(7)
<223> OTHER INFORMATION: 3-methyl-6-amino-5-(1'-beta-D-2'-
      deoxyribofuranosyl)-pyrimidin-2-one

<400> SEQUENCE: 6
aaattgncca aatacaacac tccctatagt gagtcgtatt acgcc              45

<210> SEQ ID NO 7
<211> LENGTH: 45
<212> TYPE: DNA
<213> ORGANISM: Artificial Sequence
<220> FEATURE:
<223> OTHER INFORMATION: synthetic
<220> FEATURE:
<221> NAME/KEY: misc_feature
<222> LOCATION: (39)..(39)
<223> OTHER INFORMATION: 6-amino-3-(2'-deoxy)-D-ribofuranosyl)-5-nitro-
      1H-pyridin-2-one

<400> SEQUENCE: 7
ggcgtaatac gactcactat agggagtgtt gtatttggnc aattt              45

<210> SEQ ID NO 8
<211> LENGTH: 45
<212> TYPE: DNA
<213> ORGANISM: Artificial Sequence
<220> FEATURE:
<223> OTHER INFORMATION: synthetic
<220> FEATURE:
<221> NAME/KEY: misc_feature
<222> LOCATION: (7)..(7)
<223> OTHER INFORMATION: 2-amino-8-(beta-D-2'-deoxyribofuranosyl)-
      imidazo-[1,2a]-1,3,5-triazin-[8H]-4-one

<400> SEQUENCE: 8
aaattgncca aatacaacac tccctatagt gagtcgtatt acgcc              45

<210> SEQ ID NO 9
<211> LENGTH: 45
<212> TYPE: DNA
<213> ORGANISM: Artificial Sequence
<220> FEATURE:
<223> OTHER INFORMATION: synthetic
<220> FEATURE:
<221> NAME/KEY: misc_feature
<222> LOCATION: (39)..(39)
<223> OTHER INFORMATION: 2-amino-8-(beta-D-2'-deoxyribofuranosyl)-
      imidazo-[1,2a]-1,3,5-triazin-[8H]-4-one

<400> SEQUENCE: 9
ggcgtaatac gactcactat agggagtgtt gtatttggnc aattt              45

<210> SEQ ID NO 10
<211> LENGTH: 45
<212> TYPE: DNA
<213> ORGANISM: Artificial Sequence
<220> FEATURE:
<223> OTHER INFORMATION: synthetic
<220> FEATURE:
<221> NAME/KEY: misc_feature
<222> LOCATION: (7)..(7)
<223> OTHER INFORMATION: 6-amino-3-(2'-deoxy)-D-ribofuranosyl)-5-nitro-
      1H-pyridin-2-one

<400> SEQUENCE: 10
aaattgncca aatacaacac tccctatagt gagtcgtatt acgcc              45

<210> SEQ ID NO 11
<211> LENGTH: 24
```

```
<212> TYPE: RNA
<213> ORGANISM: Artificial Sequence
<220> FEATURE:
<223> OTHER INFORMATION: synthetic
<220> FEATURE:
<221> NAME/KEY: misc_feature
<222> LOCATION: (18)..(18)
<223> OTHER INFORMATION: 2-amino-8-(beta-D-ribofuranosyl)-imidazo-
     [1,2a]-1,3,5-triazin-[8H]-4-one

<400> SEQUENCE: 11
gggaguguug uauuuggnca auuu                                              24

<210> SEQ ID NO 12
<211> LENGTH: 24
<212> TYPE: RNA
<213> ORGANISM: Artificial Sequence
<220> FEATURE:
<223> OTHER INFORMATION: synthetic
<220> FEATURE:
<221> NAME/KEY: misc_feature
<222> LOCATION: (18)..(18)
<223> OTHER INFORMATION: 6-amino-3-(D-ribofuranosyl)-5-nitro-1H-pyridin-
     2-one

<400> SEQUENCE: 12
gggaguguug uauuuggnca auuu                                              24

<210> SEQ ID NO 13
<211> LENGTH: 24
<212> TYPE: RNA
<213> ORGANISM: Artificial Sequence
<220> FEATURE:
<223> OTHER INFORMATION: synthetic
<220> FEATURE:
<221> NAME/KEY: misc_feature
<222> LOCATION: (18)..(18)
<223> OTHER INFORMATION: 6-amino-9-(1'-beta-D-ribofuranosyl)4-hydroxy-5-
     (hydroxymethyl)oxolan-2-yl]-1H-purin-2-one

<400> SEQUENCE: 13
gggaguguug uauuuggnca auuu                                              24

<210> SEQ ID NO 14
<211> LENGTH: 84
<212> TYPE: RNA
<213> ORGANISM: Artificial Sequence
<220> FEATURE:
<223> OTHER INFORMATION: synthetic
<220> FEATURE:
<221> NAME/KEY: misc_feature
<222> LOCATION: (8)..(8)
<223> OTHER INFORMATION: 6-amino-9-(1'-beta-D-ribofuranosyl)4-hydroxy-5-
     (hydroxymethyl)oxolan-2-yl]-1H-purin-2-one
<220> FEATURE:
<221> NAME/KEY: misc_feature
<222> LOCATION: (10)..(10)
<223> OTHER INFORMATION: 6-amino-3-(D-ribofuranosyl)-5-nitro-1H-pyridin-
     2-one
<220> FEATURE:
<221> NAME/KEY: misc_feature
<222> LOCATION: (76)..(76)
<223> OTHER INFORMATION: 2-amino-8-(beta-D-ribofuranosyl)-imidazo-
     [1,2a]-1,3,5-triazin-[8H]-4-one
<220> FEATURE:
<221> NAME/KEY: misc_feature
<222> LOCATION: (78)..(78)
<223> OTHER INFORMATION: 3-methyl-6-amino-5-(1'-beta-D-ribofuranosyl)-
     pyrimidin-2-one
```

```
<400> SEQUENCE: 14
ggacgcgncn gaaaugguga aggacggguc cagugcgaaa cacgcacugu ugaguagagu        60
gugagcuccg uaacungncg cguc                                               84
```